(12) United States Patent
Bonvini et al.

(10) Patent No.: US 11,098,119 B2
(45) Date of Patent: *Aug. 24, 2021

(54) COVALENTLY BONDED DIABODIES HAVING IMMUNOREACTIVITY WITH PD-1 AND LAG-3, AND METHODS OF USE THEREOF

(71) Applicant: MacroGenics, Inc., Rockville, MD (US)

(72) Inventors: Ezio Bonvini, Potomac, MD (US); Leslie S. Johnson, Darnestown, MD (US); Kalpana Shah, Boyds, MD (US); Ross La Motte-Mohs, Boyds, MD (US); Paul A. Moore, North Potomac, MD (US); Scott Koenig, Rockville, MD (US)

(73) Assignee: MacroGenics, Inc., Rockville, MD (US)

( * ) Notice: Subject to any disclaimer, the term of this patent is extended or adjusted under 35 U.S.C. 154(b) by 283 days.

This patent is subject to a terminal disclaimer.

(21) Appl. No.: 16/189,071

(22) Filed: Nov. 13, 2018

(65) Prior Publication Data

US 2019/0169292 A1    Jun. 6, 2019

Related U.S. Application Data

(63) Continuation of application No. 15/321,279, filed as application No. PCT/US2015/036634 on Jun. 19, 2015, now Pat. No. 10,160,806.

(60) Provisional application No. 62/017,467, filed on Jun. 26, 2014.

(51) Int. Cl.
*C07K 16/28* (2006.01)
*C07K 16/46* (2006.01)

(52) U.S. Cl.
CPC ...... *C07K 16/2803* (2013.01); *C07K 16/2818* (2013.01); *C07K 16/468* (2013.01); *C07K 2317/31* (2013.01); *C07K 2317/626* (2013.01); *C07K 2317/74* (2013.01)

(58) Field of Classification Search
CPC .............. C07K 16/468; C07K 2317/31; C07K 2317/626; C07K 16/2803
See application file for complete search history.

(56) References Cited

U.S. PATENT DOCUMENTS

| 4,526,938 | A | 7/1985 | Churchill et al. |
|---|---|---|---|
| 4,816,567 | A | 3/1989 | Cabilly et al. |
| 4,880,078 | A | 11/1989 | Inoue et al. |
| 4,980,286 | A | 12/1990 | Morgan et al. |
| 5,128,326 | A | 7/1992 | Leshchiner et al. |
| 5,290,540 | A | 3/1994 | Prince et al. |
| 5,565,332 | A | 10/1996 | Baier et al. |
| 5,580,717 | A | 12/1996 | Dower et al. |
| 5,679,377 | A | 10/1997 | Bernstein et al. |
| 5,733,743 | A | 3/1998 | Winter et al. |
| 5,807,715 | A | 9/1998 | Morrison et al. |
| 5,855,913 | A | 1/1999 | Hanes et al. |
| 5,866,692 | A | 2/1999 | Shitara et al. |
| 5,874,064 | A | 2/1999 | Hanes et al. |
| 5,888,533 | A | 3/1999 | Dunn |
| 5,912,015 | A | 6/1999 | Bernstein et al. |
| 5,916,597 | A | 6/1999 | Lee et al. |
| 5,934,272 | A | 8/1999 | Lloyd et al. |
| 5,945,155 | A | 8/1999 | Grill et al. |

(Continued)

FOREIGN PATENT DOCUMENTS

| EP | 2158221 | 3/2010 |
|---|---|---|
| EP | 2376109 | 10/2011 |

(Continued)

OTHER PUBLICATIONS

Agarwal, A. et al. (2008) "*The Role of Positive Costimulatory Molecules in Transplantation and Tolerance,*" Curr. Opin. Organ Transplant. 13:366-372.

Agata, T. et al. (1996) "*Expression of the PD-1 Antigen on the Surface of Stimulated Mouse T and B Lymphocytes,*" Int. Immunol. 8(5):765-772.

Antonia, S.J. et al. (2014) "*Immuno-oncology Combinations: A Review of Clinical Experience and Future Prospects,*" Clin. Cancer Res. 20(24):6258-6268.

Aruffo, A. et al. (1987) "*Molecular Cloning of a CD28 cDNA by a High-Efficiency COS Cell Expression System,*" Proc. Natl. Acad. Sci. (U.S.A.) 84:8573-8577.

Asano et al. (2004) "*A Diabody for Cancer Immunotherapy and Its Functional Enhancement by Fusion of Human Fc Domain,*" Abstract 3P-683, J. Biochem. 76(8):992.

(Continued)

*Primary Examiner* — Jessica H Roark
(74) *Attorney, Agent, or Firm* — William C. Schrot; AuerbachSchrot LLC

(57) ABSTRACT

The present invention is directed to bi-specific diabodies that comprise two or more polypeptide chains and which possess at least one Epitope-Binding Site that is immunospecific for an epitope of PD-1 and at least one Epitope-Binding Site that is immunospecific for an epitope of LAG-3 (i.e., a "PD-1× LAG-3 bi-specific diabody"). More preferably, the present invention is directed to bi-specific diabodies that comprise four polypeptide chains and which possess two Epitope-Binding Sites that are immunospecific for one (or two) epitope(s) of PD-1 and two Epitope-Binding Site that are immunospecific for one (or two) epitope(s) of LAG-3 (i.e., a "PD-1×LAG-3 bi-specific, tetra-valent diabody"). The present invention also is directed to such diabodies that additionally comprise an immunoglobulin Fc Domain ("bi-specific Fc diabodies and bi-specific, tetra-valent, Fc diabodies"). The diabodies of the present invention are capable of simultaneously binding to PD-1 and to LAG-3, particularly as such molecules are arrayed on the surfaces of human cells. The invention is directed to pharmaceutical compositions that contain such diabodies, and to methods involving the use of such diabodies in the treatment of cancer and other diseases and conditions.

14 Claims, 8 Drawing Sheets

Specification includes a Sequence Listing.

(56) References Cited

U.S. PATENT DOCUMENTS

| | | |
|---|---|---|
| 5,985,320 A | 11/1999 | Edwards |
| 5,989,309 A | 11/1999 | Wang et al. |
| 5,989,463 A | 11/1999 | Tracy et al. |
| 6,019,968 A | 2/2000 | Foster et al. |
| 6,265,150 B1 | 7/2001 | Logtenberg et al. |
| 6,331,415 B1 | 12/2001 | Cabilly et al. |
| 6,803,192 B1 | 10/2004 | Chen |
| 6,808,710 B1 | 10/2004 | Wood et al. |
| 7,101,550 B2 | 9/2006 | Wood et al. |
| 7,122,646 B2 | 10/2006 | Malmqvist et al. |
| 7,488,802 B2 | 2/2009 | Collins et al. |
| 7,521,051 B2 | 4/2009 | Collins et al. |
| 7,563,869 B2 | 7/2009 | Honjo et al. |
| 7,585,952 B2 | 9/2009 | Piccoli et al. |
| 7,595,048 B2 | 9/2009 | Honjo et al. |
| 7,635,757 B2 | 12/2009 | Freeman et al. |
| 7,638,492 B2 | 12/2009 | Wood et al. |
| 7,695,936 B2 | 4/2010 | Carter et al. |
| 7,722,868 B2 | 5/2010 | Freeman et al. |
| 7,794,710 B2 | 9/2010 | Chen et al. |
| 7,858,746 B2 | 12/2010 | Honjo et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,062,852 B2 | 11/2011 | Mozaffarian et al. |
| 8,087,074 B2 | 12/2011 | Popp et al. |
| 8,088,905 B2 | 1/2012 | Collins et al. |
| 8,227,585 B2 | 7/2012 | Piccoli et al. |
| 8,354,509 B2 | 1/2013 | Carven et al. |
| 8,460,886 B2 | 6/2013 | Shibayama et al. |
| 8,552,154 B2 | 10/2013 | Freeman et al. |
| 8,609,089 B2 | 12/2013 | Langermann et al. |
| 8,709,416 B2 | 4/2014 | Langermann et al. |
| 8,728,474 B2 | 5/2014 | Honjo et al. |
| 8,735,553 B1 | 5/2014 | Li et al. |
| 8,779,105 B2 | 7/2014 | Korman et al. |
| 8,900,587 B2 | 12/2014 | Carven et al. |
| 8,952,136 B2 | 2/2015 | Carven et al. |
| 9,005,629 B2 | 4/2015 | Pardoll et al. |
| 9,062,112 B2 | 6/2015 | Chen |
| 9,067,999 B1 | 6/2015 | Honjo et al. |
| 9,073,994 B2 | 7/2015 | Honjo et al. |
| 9,084,776 B2 | 7/2015 | Korman et al. |
| 9,163,087 B2 | 10/2015 | Kuchroo et al. |
| 9,205,148 B2 | 12/2015 | Langermann et al. |
| 9,217,034 B2 | 12/2015 | Li et al. |
| 9,220,776 B2 | 12/2015 | Sharma et al. |
| 9,284,375 B2 | 3/2016 | Johnson et al. |
| 9,358,289 B2 | 6/2016 | Korman et al. |
| 9,387,247 B2 | 7/2016 | Korman et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,889,197 B2 | 2/2018 | Johnson et al. |
| 10,160,806 B2 * | 12/2018 | Bonvini .......... A61P 35/00 |
| 2004/0220388 A1 | 11/2004 | Mertens et al. |
| 2004/0241745 A1 | 12/2004 | Honjo et al. |
| 2005/0059051 A1 | 3/2005 | Chen |
| 2007/0036783 A1 | 2/2007 | Humeau et al. |
| 2007/0041982 A1 | 2/2007 | Ponath et al. |
| 2007/0048301 A1 | 3/2007 | Bodary-Winter |
| 2007/0087006 A1 | 4/2007 | Frantz et al. |
| 2007/0092504 A1 | 4/2007 | Wyeth |
| 2007/0166281 A1 | 7/2007 | Kosak |
| 2007/0196363 A1 | 8/2007 | Carter et al. |
| 2008/0311117 A1 | 12/2008 | Collins et al. |
| 2009/0060910 A1 | 3/2009 | Johnson et al. |
| 2010/0040614 A1 | 2/2010 | Ahmed |
| 2013/0017199 A1 | 1/2013 | Langermann |
| 2013/0109843 A1 | 5/2013 | Carven et al. |
| 2013/0230514 A1 | 9/2013 | Langermann et al. |
| 2013/0295121 A1 | 11/2013 | Johnson et al. |
| 2014/0234296 A1 | 8/2014 | Sharma et al. |
| 2014/0348743 A1 | 11/2014 | Korman et al. |
| 2015/0079109 A1 | 3/2015 | Li et al. |
| 2015/0307620 A1 | 10/2015 | Vella et al. |

FOREIGN PATENT DOCUMENTS

| | | |
|---|---|---|
| EP | 2714079 | 9/2016 |
| EP | 2601216 | 1/2018 |
| WO | WO 1991/003493 | 3/1991 |
| WO | WO 1991/005548 | 5/1991 |
| WO | WO 1991/010682 | 7/1991 |
| WO | WO 1992/019244 | 11/1992 |
| WO | WO 1992/022583 | 12/1992 |
| WO | WO 1995/020605 | 8/1995 |
| WO | WO 1995/030750 | 11/1995 |
| WO | WO 1996/020698 | 7/1996 |
| WO | WO 1997/032572 | 9/1997 |
| WO | WO 1997/044013 | 11/1997 |
| WO | WO 1998/002463 | 1/1998 |
| WO | WO 1998/023741 | 6/1998 |
| WO | WO 1998/031346 | 7/1998 |
| WO | WO 1998/058059 | 12/1998 |
| WO | WO 1999/015154 | 4/1999 |
| WO | WO 1999/020253 | 4/1999 |
| WO | WO 1999/066903 | 12/1999 |
| WO | WO 2000/008363 | 2/2000 |
| WO | WO 2001/014557 | 3/2001 |
| WO | WO 2001/039722 | 6/2001 |
| WO | WO 2001/045557 | 6/2001 |
| WO | WO 2002/002781 | 1/2002 |
| WO | WO 2002/086083 | 10/2002 |
| WO | WO 2003/011911 | 2/2003 |
| WO | WO 2003/012069 | 2/2003 |
| WO | WO 2003/025018 | 3/2003 |
| WO | WO 2003/042402 | 5/2003 |
| WO | WO 2003/099196 | 12/2003 |
| WO | WO 2004/004771 | 1/2004 |
| WO | WO 2004/056875 | 7/2004 |
| WO | WO 2004/072286 | 8/2004 |
| WO | WO 2004/078928 | 9/2004 |
| WO | WO 2005/019258 | 3/2005 |
| WO | WO 2005/061547 | 7/2005 |
| WO | WO 2005/077415 | 8/2005 |
| WO | WO 2006/021955 | 3/2006 |
| WO | WO 2006/113665 | 10/2006 |
| WO | WO 2006/121168 | 11/2006 |
| WO | WO 2006/133396 | 12/2006 |
| WO | WO 2008/156712 | 12/2006 |
| WO | WO 2007/005874 | 1/2007 |
| WO | WO 2007/075270 | 7/2007 |
| WO | WO 2007/146968 | 12/2007 |
| WO | WO 2008/003103 | 1/2008 |
| WO | WO 2008/003116 | 1/2008 |
| WO | WO 2008/027236 | 3/2008 |
| WO | WO 2008/083174 | 7/2008 |
| WO | WO 2008/132601 | 11/2008 |
| WO | WO 2008/157379 | 12/2008 |
| WO | WO 2009/014708 | 1/2009 |
| WO | WO 2009/073533 | 6/2009 |
| WO | WO 2009/101611 | 8/2009 |
| WO | WO 2009/132876 | 11/2009 |
| WO | WO 2010/019570 | 2/2010 |
| WO | WO 2010/028795 | 3/2010 |
| WO | WO 2010/028796 | 3/2010 |
| WO | WO 2010/028797 | 3/2010 |
| WO | WO 2010/036959 | 4/2010 |
| WO | WO 2010/080538 | 7/2010 |
| WO | WO 2010/089411 | 8/2010 |
| WO | WO 2010/108127 | 9/2010 |
| WO | WO 2010/136172 | 12/2010 |
| WO | WO 2011/066342 | 6/2011 |
| WO | WO 2011/086091 | 7/2011 |
| WO | WO 2011/110604 | 9/2011 |
| WO | WO 2011/133886 | 10/2011 |
| WO | WO 2011/159877 | 12/2011 |
| WO | WO 2012/018687 | 2/2012 |
| WO | WO 2012/135408 | 10/2012 |
| WO | WO 2012/145493 | 10/2012 |
| WO | WO 2012/145549 | 10/2012 |

(56) References Cited

FOREIGN PATENT DOCUMENTS

| | | |
|---|---|---|
| WO | WO 2012/156430 | 11/2012 |
| WO | WO 2012/162068 | 11/2012 |
| WO | WO 2012/162583 | 11/2012 |
| WO | WO 2013/003652 | 1/2013 |
| WO | WO 2013/003761 | 1/2013 |
| WO | WO 2013/006544 | 1/2013 |
| WO | WO 2013/014668 | 1/2013 |
| WO | WO 2013/119903 | 8/2013 |
| WO | WO 2013/163427 | 10/2013 |
| WO | WO 2013/173223 | 11/2013 |
| WO | WO 2013/174873 | 11/2013 |
| WO | WO 2014/008218 | 1/2014 |
| WO | WO 2014/012479 | 1/2014 |
| WO | WO 2014/022540 | 2/2014 |
| WO | WO 2014/022758 | 2/2014 |
| WO | WO 2014/028502 | 2/2014 |
| WO | WO 2014/043708 | 3/2014 |
| WO | WO 2014/055648 | 4/2014 |
| WO | WO 2014/059251 | 4/2014 |
| WO | WO 2014/066532 | 5/2014 |
| WO | WO 2014/066834 | 5/2014 |
| WO | WO 2014/140180 | 9/2014 |
| WO | WO 2014/179664 | 11/2014 |
| WO | WO 2014/194302 | 12/2014 |
| WO | WO 2014/209804 | 12/2014 |
| WO | WO 2015/026684 | 2/2015 |
| WO | WO 2015/026894 | 2/2015 |
| WO | WO 2015/036394 | 3/2015 |
| WO | WO 2015/042246 | 3/2015 |
| WO | WO 2015/048312 | 4/2015 |
| WO | WO 2015/103072 | 7/2015 |
| WO | WO 2015/112534 | 7/2015 |
| WO | WO 2015/112800 | 7/2015 |
| WO | WO 2015/116539 | 8/2015 |
| WO | WO 2015/138920 | 9/2015 |
| WO | WO 2015/176033 | 11/2015 |
| WO | WO 2015/195163 | 12/2015 |
| WO | WO 2015/200828 | 12/2015 |
| WO | WO 2016/014688 | 1/2016 |
| WO | WO 2016/015685 | 2/2016 |
| WO | WO 2016/020856 | 2/2016 |
| WO | WO 2016/022630 | 2/2016 |
| WO | WO 2016/028672 | 2/2016 |
| WO | WO 2016/068801 | 5/2016 |
| WO | WO 2016/077397 | 5/2016 |
| WO | WO 2016/092419 | 6/2016 |
| WO | WO 2016/106159 | 6/2016 |
| WO | WO 2016/127179 | 8/2016 |
| WO | WO 2016/168716 | 10/2016 |
| WO | WO 2017/079112 | 5/2017 |

OTHER PUBLICATIONS

Atwell et al. (1997) "Stable Heterodimers From Remodeling the Domain Interface of a Homodimer Using a Phage Display Library," J. Mol. Biol. 270: 26-35.
Baeuerle, P et al. (2008) "BiTE: A New Class of Antibodies That Recruit T-Cells," Drugs of the Future 33: 137-147.
Baeuerle, P.A. et al. (2009) "Bispecific T-Cell Engaging Antibodies for Cancer Therapy," Cancer Res. 69(12):4941-4944.
Bargou, et al. (2008) "Tumor Regression in Cancer Patients by Very Low Doses of a T-Cell-Engaging Antibody," Science 321: 974-977.
Bennett F, et al., (2003) "Program Death-1 Engagement Upon TCR Activation Has Distinct Effects on Costimulation and and Cytokine-Driven Proliferation: Attenuation of ICOS, IL-4, and IL-21, but Not CD28, IL-7, IL-15 Responses" J Immunol 170:711-718.
Berger, R. et al. (2008) "Phase I Safety and Pharmacokinetic Study of CT-011, A Humanized Antibody Interacting With PD-1, In Patients With Advanced Hematologic Malignancies," Clin. Cancer Res. 14(10):3044-3051.
Bird et al. (1988) "Single-Chain Antigen-Binding Proteins," Science 242:423-426.
Blank, C. et al. (Epub Dec. 29, 2006) "Contribution of the PD-L1/PD-1 Pathway to T-Cell Exhaustion: An Update on Implications for Chronic Infections and Tumor Evasion Cancer," Immunol. Immunother. 56(5):739-745.
Brahmer JR, et al., (2010) "Phase I Study of Single-Agent Anti—Programmed Death-1 (MDX-1106) in Refractory Solid Tumors: Safety, Clinical Activity, Pharmacodynamics, and Immunologic Correlates" J Clin Oncol 28:3167-75.
Brown, J.A. et al. (2003) "Blockade of Programmed Death-1 Ligands on Dendritic Cells Enhances T-Cell Activation and Cytokine Production," J. Immunol. 170:1257-1266.
Buchwald et al. (1980) "Long-Term, Continuous Intravenous Heparin Administration by an Implantable Infusion Pump in Ambulatory Patients With Recurrent Venous Thrombosis," Surgery 88:507-516.
Butler, N.S. et al. (2012) "Therapeutic Blockade of PD-L1 and LAG-3 Rapidly Clears Established Blood-Stage Plasmodium Infection," Nature Immunol. 13(2):188-195.
Cao et al. (2003) "Bispecific Antibody Conjugates in Therapeutics," Adv. Drug. Deliv. Rev. 55:171-197.
Capece, D. et al. (2012) "Targeting Costimulatory Molecules to Improve Antitumor Immunity," J. Biomed. Biotech. 2012:926321.
Carter, L. et al. (2002) "PD-1:PD-L inhibitory pathway affects both CD4(+) and CD8(+) T-cells and is overcome by IL-2," Eur. J. Immunol. 32(3):634-643.
Chan, A.C. et al. (2010) "Therapeutic Antibodies for Autoimmunity and Inflammation," Nat. Rev. 10:301-316.
Chan, C.E. et al. (2009) "The Use of Antibodies in the Treatment of Infectious Diseases," Singapore Med. J. 50(7):663-666.
Chen L. et al. (2013) "Molecular Mechanisms of T-Cell Co-Stimulation and Co-Inhibition," Nature Reviews Immunology 13(4):227-242.
Chen, Y. et al. (2005) "Expression of B7-H1 in Inflammatory Renal Tubular Epithelial Cells," Nephron. Exp. Nephrol. 102:e81-e92.
Collins, M. et al. (2005) "The B7 Family of Immune-Regulatory Ligands," Genome Biol. 6:223.1-223.7.
Coyle, A.J. et al. (2001) "The Expanding B7 Superfamily: Increasing Complexity in Costimulatory Signals Regulating T-Cell Function," Nature Immunol. 2(3):203-209.
Creelan, B.C. (2014) "Update on Immune Checkpoint Inhibitors in Lung Cancer," Cancer Control 21(1):80-89.
De Haij, S. et al. (2005) "Renal Tubular Epithelial Cells Modulate T-Cell Responses Via ICOS-L and B7-H1" Kidney Int. 68:2091-2102.
Dong, C. et al. (2003) "Immune Regulation by Novel Costimulatory Molecules," Immunolog. Res. 28(1):39-48.
Dong, H. (2003) "B7-H1 Pathway and Its Role in the Evasion of Tumor Immunity," J. Mol. Med. 81:281-287.
Dorfman DM, et al., (2006) "Programmed Death-1 (PD-1) is a Marker of Germinal Center-assoicated T Cells and Angioimmunoblastic T-Cell Lymphoma" Am J Surg Pathol 30:802-10.
During et al. (1989) "Controlled Release of Dopamine From a Polymeric Brain Implant: In Vivo Characterization," Ann. Neurol. 25:351-356.
Eppihimer MJ, et al., (2009) "Expression and Regulation of the PD-L1 Immunoinhibitory Molecule on Microvascular Endothelial Cells" Microcirculation 9: 133-145".
Fitzgerald et al. (1997) "Improved Tumour Targeting by Disulphide Stabilized Diabodies Expressed in Pichia pastoris," Protein Eng. 10:1221.
Flajnik, M.F. et al. (2012) "Evolution of the B7 Family: Co-Evolution of B7H6 and Nkp30, Identification of a New B7 Family Member, B7H7, and of B7's Historical Relationship With the MHC," Immunogenetics epub doi.org/10.1007/s00251-012-0616-2.
Flies, D.B. et al. (2007) "The New B7s: Playing a Pivotal Role in Tumor Immunity," J. Immunother. 30(3):251-260.
Freeman, G.J. et al. (2000) "Engagement of the PD-1 Immunoinhibitory Receptor by a Novel B7 Family Member Leads to Negative Regulation of Lymphocyte Activation," J. Exp. Med. 192:1-9.
Ganesan, A. (2006) "Solid-Phase Synthesis in the Twenty-First Century," Mini Rev. Med. Chem. 6(1):3-10.
Greenwald, R.J. et al. (2005) "The B7 Family Revisited," Ann. Rev. Immunol. 23:515-548.

(56) References Cited

OTHER PUBLICATIONS

Gross, J., et al. (1992) "*Identification and Distribution of the Costimulatory Receptor CD28 in the Mouse,*" J. Immunol. 149:380-388.

Grosso, J.F. et al. (2007) "*LAG-3 Regulates CD8+ T-Cell Accumulation and Effector Function During Self and Tumor Tolerance,*" J. Clin. Invest. 117:3383-3392.

Grosso, J.F. et al. (2009) "*Functionally Distinct LAG-3 and PD-1 Subsets on Activated and Chronically Stimulated CD8 T-Cells,*" J. Immunol. 182(11):6659-6669.

Hamid O, et al., (2013) "*Safety and tumor responses with lambrolizumab (anti-PD-1) in melanoma*" N Engl J Med 369:134-44.

Hannier, S. et al. (1998) "*CD3/TCR Complex-Associated Lymphocyte Activation Gene-3 Molecules Inhibit CD3/TCR Signaling,*" J. Immunol. 161:4058-4065.

Hardy B, et al., (1994) "*A Monoclonal Antibody against a Human B Lymphoblastoid Cell Line Induces Tumor Regression in Mice*" Cancer Res 54:5793-5796.

Hardy B, et al., (1997) "*A lymphocyte-activating monoclonal antibody induces regression of human tumors in severe combined immunodeficient mice*" PNAS 94:5756-5760.

Holliger et al. (1993) "*'Diabodies': Small Bivalent and Bispecific Antibody Fragments,*" Proc. Natl. Acad. Sci. (U.S.A.) 90:6444-6448.

Holliger et al. (1996) "*Specific Killing of Lymphoma Cells by Cytotoxic T-Cells Mediated by a Bispecific Diabody,*" Protein Eng. 9:299-305.

Holliger et al. (1999) "*Carcinoembryonic Antigen (CEA)-Specific T-cell Activation in Colon Carcinoma Induced by Anti-CD3 x Anti-CEA Bispecific Diabodies and B7 x Anti-CEA Bispecific Fusion Proteins,*" Cancer Res. 59:2909-2916.

Houghten, R.A. (1985) "*General Method for the Rapid Solid-Phase Synthesis of Large Numbers of Peptides: Specificity of Antigen-Antibody Interaction at the Level of Individual Amino Acids,*" Proc. Natl. Acad. Sci. (U.S.A.) 82(15):5131-5135.

Howard et al. (1989) "*Intracerebral Drug Delivery in Rats With Lesion Induced Memory Deficits,*" J. Neurosurg. 7(1):105-112.

Huang, C.T. et al. (2004) "*Role of LAG-3 in Regulatory T-Cells,*" Immunity 21:503-513.

Huard, B. et al. (1994) "*Cellular Expression and Tissue Distribution of the Human LAG-3-Encoded Protein, An MHC Class II Ligand,*" Immunogenetics 39:213-217.

Huard, B. et al. (1994) "*Lymphocyte-Activation Gene 3/Major Histocompatibility Complex Class II Interaction Modulates the Antigenic Response of CD4+ T Lymphocytes,*" Eur. J. Immunol. 24:3216-3221.

Huard, B. et al. (1995) "*CD4/Major Histocompatibility Complex Class II Interaction Analyzed With CD4- and Lymphocyte Activation Gene-3 (LAG-3)-Ig Fusion Proteins,*" Eur. J. Immunol. 25:2718-2721.

International Search Report PCT/US2015/036634 (WO 2015/200119) (dated 2015) (5 pages).

Ishida, Y. et al. (1992) "*Induced Expression of PD-1, A Novel Member of the Immunoglobulin Gene Superfamily, Upon Programmed Cell Death,*" EMBO J. 11:3887-3895.

Johnson, S. et al. (2010) "*Effector Cell Recruitment With Novel Fv-Based Dual-Affinity Re-Targeting Protein Leads to Potent Tumor Cytolysis and in vivo B-Cell Depletion,*" J. Mol. Biol. 399(3):436-449.

Joliot et al. (1991) "*Antennapedia Homeobox Peptide Regulates Neural Morphogenesis,*" Proc. Natl. Acad. Sci. (U.S.A.) 88:1864-1868.

Kohler, G. et al. (1975) "*Continuous Cultures of Fused Cells Secreting Antibody of Predefined Specificity,*" Nature 256:495-497.

Korman, A.J. et al. (2007) "*Checkpoint Blockade in Cancer Immunotherapy,*" Adv. Immunol. 90:297-339.

Kulpa, D.A. et al. (2013) "*PD-1 Coinhibitory Signals: The Link Between Pathogenesis and Protection,*" Semin Immunol. 25(3):1-20.

Langer (1990) "*New Methods of Drug Delivery,*" Science 249:1527-1533.

Latchman, Y. et al. (2001) "*PD-L2 is a Second Ligand for PD-1 and Inhibits T-Cell Activation,*" Nat. Immunol 2:261-268.

Latchman, Y.E. et al. (2004) "*PD-L1-Deficient Mice Show That PD-L1 on T-Cells, Antigen-Presenting Cells, and Host Tissues Negatively Regulates T-Cells.*" Proc. Natl. Acad. Sci. (U.S.A.) 101(29):10691-10696.

Lenschow, D.J. et al. (1996) "*CD28/B7 System of T-Cell Costimulation,*" Ann. Rev. Immunol. 14:233-258.

Lepenies, B. et al. (2008) "*The Role of Negative Costimulators During Parasitic Infections,*" Endocrine, Metabolic & Immune Disorders—Drug Targets 8:279-288.

Levy et al. (1985) "*Inhibition of Calcification of Bioprosthetic Heart Valves by Local Controlled-Release Diphosphonate,*" Science 228:190-192.

Lindley, P.S. et al. (2009) "*The Clinical Utility of Inhibiting CD28-Mediated Costimulation,*" Immunol. Rev. 229:307-321.

Linsley, P. et al. (1996) "*Intracellular Trafficking of CTLA4 and Focal Localization Towards Sites of TCR Engagement,*" Immunity 4:535-543.

Loke, P. et al. (2004) "*Emerging Mechanisms of Immune Regulation: The Extended B7 Family and Regulatory T-Cells.*" Arthritis Res. Ther. 6:208-214.

Lonberg, N. et al. (1995) "*Human Antibodies From Transgenic Mice,*" Int. Rev. Immunol 13:65-93.

Lu, D. et al. (2005) "*A Fully Human Recombinant IgG-Like Bispecific Antibody to Both the Epidermal Growth Factor Receptor and the Insulin-Like Growth Factor Receptor for Enhanced Antitumor Activity,*" J. Biol. Chem. 280(20):19665-19672.

MacroGenics R&D Day, Oct. 13, 2015.

Mahoney, K.M. et al. (2015) "*The Next Immune-Checkpoint Inhibitors: PD-1/PD-L1 Blockade in Melanoma,*" Clinical Therapeutics 37(4):764-782.

Martin-Orozco, N. et al. (2007) "*Inhibitory Costimulation and Anti-Tumor Immunity,*" Semin. Cancer Biol. 17(4):288-298.

Marvin et al. (2005) "*Recombinant Approaches to IgG-Like Bispecific Antibodies,*" Acta Pharmacol. Sin. 26:649-658.

Matsuzaki, J. et al. (2010) "*Tumor-Infiltrating NY-ESO-1-Specific CD8+ T-Cells Are Negatively Regulated by LAG-3 and PD-1 in Human Ovarian Cancer,*" Proc. Natl. Acad. Sci. (U.S.A.) 107(17):7875-7880.

Mazanet, M.M. et al. (2002) "*B7-H1 is Expressed by Human Endothelial Cells and Suppresses T-Cell Cytokine Synthesis,*" J. Immunol. 169:3581-3588.

Melero, I. et al. (2013) "*Agonist Antibodies to TNFR Molecules That Costimulate T and NK Cells,*" Clin. Cancer Res. 19(5):1044-1053.

Merrifield, B. (1986) "*Solid Phase Synthesis,*" Science 232(4748):341-347.

MGD013, a Bispecific PD-1 x LAG-3 Dual-Affinity Re-Targeting (DART®) Protein with T-cell Immunomodulatory Activity for Cancer Treatment American Association for Cancer Research Annual Meeting (AACR) Apr. 16-20, 2016, New Orleans, LA.

Moore, P. "DART Molecules for Immunomodulatory Therapeutic Strategies" 8th GTC Immunotherapeutics and Immunomonitoring Conference, Jan. 25, 2016, San Diego, CA.

Moore, P.A. et al. (2011) "*Application of Dual Affinity Retargeting Molecules to Achieve Optimal Redirected T-Cell Killing of B-Cell Lymphoma,*" Blood 117(17):4542-4551.

Ning et al. (1996) "*Intratumoral Radioimmunotherapy of a Human Colon Cancer Xenograft Using a Sustained Release Gel,*" Radiotherapy & Oncology 39:179 189.

Nishimura, H. et al. (2000) "*Facilitation of Beta Selection and Modification of Positive Selection in the Thymus of PD-1-Deficient Mice,*" J. Exp. Med. 191:891-898.

Okazaki, T. et al. (2011) "*PD-1 and LAG-3 inhibitor Coreceptors Act Synergistically to Prevent Autoimmunity in Mice,*" J. Exp. Med. 208(2):395-407.

Olafsen et al. (2004) "*Covalent Disulfide-Linked Anti-CEA Diabody Allows Site-Specific Conjugation and Radiolabeling for Tumor Targeting Applications,*" Prot. Engr. Des. Sel. 17:21-27.

(56) References Cited

OTHER PUBLICATIONS

Peeters et al. (2001) "*Production of Antibodies and Antibody Fragments in Plants*," Vaccine 19:2756.
Petroff, M.G. et al. (2002) "*B7 Family Molecules: Novel Immunomodulators at the Maternal-Fetal Interface*," Placenta 23:S95-S101.
Pollock et al. (1999) "*Transgenic Milk as a Method for the Production of Recombinant Antibodies*," J. Immunol Methods 231:147-157.
Ridgway et al. (1996) "'*Knobs-Into-Holes' Engineering of Antibody CH3 Domains for Heavy Chain Heterodimerization*," Protein Engr. 9:617-621.
Saudek et al. (1989) "*A Preliminary Trial of the Programmable Implantable Medication System for Insulin Delivery*," N. Engl. J. Med. 321:574-579.
Sefton, (1987) "*Implantable Pumps*," CRC Crit. Rev. Biomed. Eng. 14:201-240 (Abstract Only).
Sharpe, A.H. et al. (2002) "*The B7-CD28 Superfamily*," Nature Rev. Immunol. 2:116-126.
Song et al. (1995) "*Antibody Mediated Lung Targeting of Long Circulating Emulsions*," PDA Journal of Pharmaceutical Science & Technology 50:372 397.
Staerz et al. (1985) "*Hybrid Antibodies Can Target Sites for Attack by T-Cells*," Nature 314:628-631.
Stavenhagen, J.B. et al. (2007) "*Fc Optimization of Therapeutic Antibodies Enhances Their Ability to Kill Tumor Cells In Vitro and Controls Tumor Expansion In Vivo Via Low Affinity Activating Fcgamma Receptors*," Cancer Res. 57(18):8882-8890.
Stephan, J. et al. (1999) "*Selective Cloning of Cell Surface Proteins Involved in Organ Development: Epithelial Glycoprotein is Involved in Normal Epithelial Differentiation*," Endocrinol. 140:5841-5854.
Subudhi, S.K. et al. (2005) "*The Balance of Immune Responses: Costimulation Verse Coinhibition*," J. Molec. Med. 83:193-202.
Takemura, S. et al. (2000) "*Construction of a Diabody (Small Recombinant Bispecific Antibody) Using a Refolding System*," Protein Eng. 13(8):583-588.
Topalian SL, et al. (2012) "*Safety, activity, and immune correlates of anti-PD-1 antibody in cancer*" N Engl J Med 366:2443-54.
Turnis M, et al., (2012) "*Combinatorial immunotherapy PD-1 may not be LAG-ing behind any more*" OncoImmunology 1:7, 1172-1174.
Turnis, M.E. et al. (2012) "*Combinatorial Immunotherapy*," OncoImmunology 1(7):1172-1174.
Veri, M.C. et al. (2010) "*Therapeutic Control of B Cell Activation Via Recruitment of Fcgamma Receptor IIb (CD32B) Inhibitory Function With a Novel Bispecific Antibody Scaffold*," Arthritis Rheum. 62(7):1933-1943.
Viglietta, V. et al. (2007) "*Modulating Co-Stimulation*," Neurotherapeutics 4:666-675.
Wang, L. et al. (Mar. 7, 2011) "*VISTA, A Novel Mouse Ig Superfamily Ligand That Negatively Regulates T-Cell Responses*," J. Exp. Med. 10.1084/jem.20100619:1-16.
Wang, S. et al. (2004) "*Co-Signaling Molecules of the B7-CD28 Family in Positive and Negative Regulation of T Lymphocyte Responses*," Microbes Infect. 6:759-766.
Wang, W. et al. (2008) "*PD-L1/PD-1 Signal Deficiency Promotes Allogeneic Immune Responses and Accelerates Heart Allograft Rejection*," Transplantation 86(6):836-44.
Winter, G. et al. (1994) "*Making Antibodies by Phage Display Technology*," Annu. Rev. Immunol. 12.433-455.
Woo, S.R. et al. (2011) "*Immune Inhibitory Molecules LAG-3 and PD-1 Synergistically Regulate T-Cell Function to Promote Tumoral Immune Escape*," Cancer Res. 72(4):917-927.
Workman C.J., et al. (2004) "*Lymphocyte Activation Gene-3 (CD223) Regulates the Size of the Expanding T-Cell Population Following Antigen Activation in vivo*," J. Immunol. 172:5450-5455.
Workman, C.J. (2005) "*Negative Regulation of T-Cell Homeostasis by Lymphocyte Activation Gene-3 (CD223)*," J. Immunol. 174:688-695.
Workman, C.J. et al. (2002) "*Cutting Edge: Molecular Analysis of the Negative Regulatory Function of Lymphocyte Activation Gene-3*," J. Immunol. 169:5392-5395.
Workman, C.J. et al. (2002) "*Phenotypic Analysis of the Murine CD4-Related Glycoprotein, CD223 (LAG-3),* " Eur. J. Immunol. 32:2255-2263.
Workman, C.J. et al. (2003) "*The CD4-Related Molecule, LAG-3 (CD223), Regulates the Expansion of Activated T-Cells*," Eur. J. Immunol. 33:970-979.
Workman, C.J. et al. (2009) "*LAG-3 Regulates Plasmacytoid Dendritic Cell Homeostasis*," J. Immunol. 182(4): 1885-1891.
Written Opinion of the International Searching Authority PCT/US2015/036634 (WO 2015/200119) (dated 2015) (9 pages).
Wu et al. (1987) "*Receptor-Mediated in Vitro Gene Transformation by a Soluble DNA Carrier System*," J. Biol. Chem. 262:4429-4432.
Wu, A. et al. (2001) "*Multimerization of a Chimeric Anti-CD20 Single Chain Fv-Fv Fusion Protein is Mediated Through Variable Domain Exchange*," Protein Engineering 14(2): 1025-1033.
Xie et al. (2005) "*A New Format of Bispecific Antibody: Highly Efficient Heterodimerization, Expression and Tumor Cell Lysis*," J. Immunol. Methods 296:95-101.
Yamazaki, T. et al. (2002) "*Expression of Programmed Death 1 Ligands by Murine T-Cells and APC*," J. Immunol. 169:5538-5545.
Poirier, N., et al. (2011), "*Antibody-mediated Depletion of Lymphocyte-Activation Gene-3 (LAG-3+)-Activated T lymphocytes Prevents Delayed-type Hypersensitivity in Non-human Primates*", Clinical and Experimental Immunology, 2011, 164: 265-274.
La Motte-Mohs et al., *Preclinical Characterization of MGD013, a PD-1 x LAG-3 Bispecific DART® Molecule*, SITC 32nd Annual Meeting, Nov. 8-12, 2017, National Harbor, Maryland.
Luke et al., *A phase I, first-in-human, open-label, dose-escalation study of MGD013, a bispecific DART molecule binding PD-1 and LAG-3, in patients with unresectable or metastatic neoplasms*, J Clin Oncol 38, No. 15, Suppl, May 20, 2020, 3004, Abstract.

* cited by examiner

SEQUENCE LISTING

<160> NUMBER OF SEQ ID NOS: 32

<210> SEQ ID NO 1
<211> LENGTH: 288
<212> TYPE: PRT
<213> ORGANISM: Homo sapiens
<220> FEATURE:
<221> NAME/KEY: misc
<222> LOCATION: (1)..(288)
<223> OTHER INFORMATION: human PD-1 including signal sequence

<400> SEQUENCE: 1

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 2
<211> LENGTH: 113
<212> TYPE: PRT
<213> ORGANISM: Homo sapiens
<220> FEATURE:
<221> NAME/KEY: MISC_FEATURE
<222> LOCATION: (1)..(113)
<223> OTHER INFORMATION: Anti-PD-1 Antibody mAb 1 Heavy Chain Variable
      Region

```
<400> SEQUENCE: 2

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 3
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Anti-PD-1 Antibody mAb 1 Light Chain Variable
      Region

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 4
<211> LENGTH: 120
<212> TYPE: PRT
<213> ORGANISM: Artificial Sequence
<220> FEATURE:
<223> OTHER INFORMATION: Humanized Anti-PD-1 Antibody mAb 2 Heavy Chain
      Variable Region

<400> SEQUENCE: 4

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45
```

```
Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser
            115                 120
```

<210> SEQ ID NO 5
<211> LENGTH: 111
<212> TYPE: PRT
<213> ORGANISM: Artificial Sequence
<220> FEATURE:
<223> OTHER INFORMATION: Humanized Anti-PD-1 Antibody mAb 2 Light Chain
      Variable Region

<400> SEQUENCE: 5

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Lys Gly Val Ser Thr Ser
                 20                  25                  30

Gly Tyr Ser Tyr Leu His Trp Tyr Gln Gln Lys Pro Gly Gln Ala Pro
             35                  40                  45

Arg Leu Leu Ile Tyr Leu Ala Ser Tyr Leu Glu Ser Gly Val Pro Ala
         50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys
                100                 105                 110
```

<210> SEQ ID NO 6
<211> LENGTH: 121
<212> TYPE: PRT
<213> ORGANISM: Mus musculus

<400> SEQUENCE: 6

```
Gln Val Gln Leu Gln Gln Ser Gly Ala Glu Leu Ala Lys Pro Gly Ala
  1               5                  10                  15

Ser Val Gln Met Ser Cys Lys Ala Ser Gly Tyr Ser Phe Thr Ser Ser
                 20                  25                  30

Trp Ile His Trp Val Lys Gln Arg Pro Gly Gln Gly Leu Glu Trp Ile
             35                  40                  45

Gly Tyr Ile Tyr Pro Ser Thr Gly Phe Thr Glu Tyr Asn Gln Lys Phe
         50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Trp Arg Asp Ser Ser Gly Tyr His Ala Met Asp Tyr Trp Gly
                100                 105                 110

Gln Gly Thr Ser Val Thr Val Ser Ser
            115                 120
```

<210> SEQ ID NO 7
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: Anti-PD-1 Antibody mAb 3 Light Chain Variable
      Region

<400> SEQUENCE: 7

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Lys Phe Gly Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

<210> SEQ ID NO 8
<211> LENGTH: 117
<212> TYPE: PRT
<213> ORGANISM: Artificial Sequence
<220> FEATURE:
<223> OTHER INFORMATION: Humanized Anti-PD-1 Antibody mAb 4 Heavy Chain
      Variable Region

<400> SEQUENCE: 8

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115

<210> SEQ ID NO 9
<211> LENGTH: 106
<212> TYPE: PRT
<213> ORGANISM: Artificial Sequence
<220> FEATURE:
<223> OTHER INFORMATION: Humanized Anti-PD-1 Antibody mAb 4 Light Chain
      Variable Region

<400> SEQUENCE: 9

```
Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65              70                  75                  80

Asp Phe Ala Thr Tyr Tyr Cys Gln Gln Arg Ser Ser Pro Leu Thr
                85                  90                  95

Phe Gly Gly Gly Thr Lys Leu Glu Ile Lys
            100                 105
```

<210> SEQ ID NO 10
<211> LENGTH: 525
<212> TYPE: PRT
<213> ORGANISM: Homo sapiens
<220> FEATURE:
<221> NAME/KEY: MISC_FEATURE
<222> LOCATION: (1)..(525)
<223> OTHER INFORMATION: human LAG3 (CD223) protein including signal
      sequence

<400> SEQUENCE: 10

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65              70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145             150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225             230                 235                 240
```

-continued

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525

<210> SEQ ID NO 11
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Anti-LAG-3 Antibody mAb 1 Heavy Chain Variable
      Region

<400> SEQUENCE: 11

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

```
Ser Arg Val Thr Leu Ser Leu Asp Thr Ser Lys Asn Gln Phe Ser Leu
 65                  70                  75                  80

Lys Leu Arg Ser Val Thr Ala Ala Asp Thr Ala Val Tyr Tyr Cys Ala
                 85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 12
<211> LENGTH: 107
<212> TYPE: PRT
<213> ORGANISM: Homo sapiens
<220> FEATURE:
<221> NAME/KEY: MOD_RES
<222> LOCATION: (1)..(107)
<223> OTHER INFORMATION: Anti-LAG-3 Antibody mAb 1 Light Chain Variable
      Region

<400> SEQUENCE: 12

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gln Gly Thr Asn Leu Glu Ile Lys
            100                 105

<210> SEQ ID NO 13
<211> LENGTH: 8
<212> TYPE: PRT
<213> ORGANISM: Artificial Sequence
<220> FEATURE:
<223> OTHER INFORMATION: Linker 1

<400> SEQUENCE: 13

Gly Gly Gly Ser Gly Gly Gly Gly
 1               5

<210> SEQ ID NO 14
<211> LENGTH: 28
<212> TYPE: PRT
<213> ORGANISM: Artificial Sequence
<220> FEATURE:
<223> OTHER INFORMATION: E-Coil Heterodimer-Promoting Domain

<400> SEQUENCE: 14

Glu Val Ala Ala Leu Glu Lys Glu Val Ala Ala Leu Glu Lys Glu Val
 1               5                  10                  15

Ala Ala Leu Glu Lys Glu Val Ala Ala Leu Glu Lys
             20                  25

<210> SEQ ID NO 15
<211> LENGTH: 28
```

-continued

```
<212> TYPE: PRT
<213> ORGANISM: Artificial Sequence
<220> FEATURE:
<223> OTHER INFORMATION: K-Coil Heterodimer-Promoting Domain

<400> SEQUENCE: 15

Lys Val Ala Ala Leu Lys Glu Lys Val Ala Ala Leu Lys Glu Lys Val
1               5                   10                  15
Ala Ala Leu Lys Glu Lys Val Ala Ala Leu Lys Glu
            20                  25

<210> SEQ ID NO 16
<211> LENGTH: 28
<212> TYPE: PRT
<213> ORGANISM: Artificial Sequence
<220> FEATURE:
<223> OTHER INFORMATION: Cysteine-Containing E-Coil Heterodimer-
      Promoting Domain

<400> SEQUENCE: 16

Glu Val Ala Ala Cys Glu Lys Glu Val Ala Ala Leu Glu Lys Glu Val
1               5                   10                  15
Ala Ala Leu Glu Lys Glu Val Ala Ala Leu Glu Lys
            20                  25

<210> SEQ ID NO 17
<211> LENGTH: 28
<212> TYPE: PRT
<213> ORGANISM: Artificial Sequence
<220> FEATURE:
<223> OTHER INFORMATION: Cysteine-Containing K-Coil Heterodimer-
      Promoting Domain

<400> SEQUENCE: 17

Lys Val Ala Ala Cys Lys Glu Lys Val Ala Ala Leu Lys Glu Lys Val
1               5                   10                  15
Ala Ala Leu Lys Glu Lys Val Ala Ala Leu Lys Glu
            20                  25

<210> SEQ ID NO 18
<211> LENGTH: 6
<212> TYPE: PRT
<213> ORGANISM: Artificial Sequence
<220> FEATURE:
<223> OTHER INFORMATION: Cysteine-Containing Spacer Peptide

<400> SEQUENCE: 18

Gly Gly Cys Gly Gly Gly
1               5

<210> SEQ ID NO 19
<211> LENGTH: 10
<212> TYPE: PRT
<213> ORGANISM: Artificial Sequence
<220> FEATURE:
<223> OTHER INFORMATION: Cysteine-Containing Linker Peptide

<400> SEQUENCE: 19

Asp Lys Thr His Thr Cys Pro Pro Cys Pro
1               5                   10

<210> SEQ ID NO 20
<211> LENGTH: 15
<212> TYPE: PRT
<213> ORGANISM: Artificial Sequence
<220> FEATURE:
```

<223> OTHER INFORMATION: Alternative Cysteine-Containing Linker Peptide

<400> SEQUENCE: 20

```
Leu Glu Pro Lys Ser Ala Asp Lys Thr His Thr Cys Pro Pro Cys
1               5                   10                  15
```

<210> SEQ ID NO 21
<211> LENGTH: 218
<212> TYPE: PRT
<213> ORGANISM: Homo sapiens
<220> FEATURE:
<221> NAME/KEY: MISC_FEATURE
<222> LOCATION: (1)..(218)
<223> OTHER INFORMATION: IgG1 Fc Region

<400> SEQUENCE: 21

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
                20                  25                  30

Val Val Val Asp Val Ser His Glu Asp Pro Glu Val Lys Phe Asn Trp
            35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
                100                 105                 110

Gln Pro Arg Glu Pro Gln Val Tyr Thr Leu Pro Pro Ser Arg Glu Glu
            115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
                180                 185                 190

Val Phe Ser Cys Ser Val Met His Glu Ala Leu His Asn His Tyr Thr
            195                 200                 205

Gln Lys Ser Leu Ser Leu Ser Pro Gly Lys
    210                 215
```

<210> SEQ ID NO 22
<211> LENGTH: 218
<212> TYPE: PRT
<213> ORGANISM: Artificial Sequence
<220> FEATURE:
<223> OTHER INFORMATION: "Knob-Bearing" IgG1 CH2-CH3 Domain

<400> SEQUENCE: 22

```
Pro Ala Pro Glu Ala Ala Gly Gly Pro Ser Val Phe Leu Phe Pro Pro
1               5                   10                  15

Lys Pro Lys Asp Thr Leu Met Ile Ser Arg Thr Pro Glu Val Thr Cys
                20                  25                  30

Val Val Val Asp Val Ser His Glu Asp Pro Glu Val Lys Phe Asn Trp
            35                  40                  45
```

Tyr Val Asp Gly Val Glu Val His Asn Ala Lys Thr Lys Pro Arg Glu
            50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Trp Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 23
<211> LENGTH: 218
<212> TYPE: PRT
<213> ORGANISM: Artificial Sequence
<220> FEATURE:
<223> OTHER INFORMATION: "Hole-Bearing" IgG1 CH2-CH3 Domain

<400> SEQUENCE: 23

Pro Ala Pro Glu Ala Ala Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Ser Cys Ala Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Val Ser Lys Leu Thr Val Asp Lys Ser Arg Trp Gln Gln Gly Asn
            180                 185                 190

Val Phe Ser Cys Ser Val Met His Glu Ala Leu His Asn Arg Tyr Thr
            195                 200                 205

Gln Lys Ser Leu Ser Leu Ser Pro Gly Lys
    210                 215

<210> SEQ ID NO 24
<211> LENGTH: 217
<212> TYPE: PRT
<213> ORGANISM: Artificial Sequence
<220> FEATURE:
<223> OTHER INFORMATION: IgG1 Fc Region L234A/L235A Variant

<400> SEQUENCE: 24

Pro Ala Pro Glu Ala Ala Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly
    210                 215

<210> SEQ ID NO 25
<211> LENGTH: 494
<212> TYPE: PRT
<213> ORGANISM: Artificial Sequence
<220> FEATURE:
<223> OTHER INFORMATION: First and Third Polypeptide Chains of the
      Exemplary PD-1 x LAG-3 Fc-DART-1 diabody

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

```
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Leu
                 85                  90                  95
Thr Phe Gly Gln Gly Thr Asn Leu Glu Ile Lys Gly Gly Gly Ser Gly
            100                 105                 110
Gly Gly Gly Gln Val Gln Leu Val Glu Ser Gly Gly Val Val Gln
            115                 120                 125
Pro Gly Arg Ser Leu Arg Leu Asp Cys Lys Ala Ser Gly Ile Thr Phe
        130                 135                 140
Ser Asn Ser Gly Met His Trp Val Arg Gln Ala Pro Gly Lys Gly Leu
145                 150                 155                 160
Glu Trp Val Ala Val Ile Trp Tyr Asp Gly Ser Lys Arg Tyr Tyr Ala
                165                 170                 175
Asp Ser Val Lys Gly Arg Phe Thr Ile Ser Arg Asp Asn Ser Lys Asn
            180                 185                 190
Thr Leu Phe Leu Gln Met Asn Ser Leu Arg Ala Glu Asp Thr Ala Val
        195                 200                 205
Tyr Tyr Cys Ala Thr Asn Asp Asp Tyr Trp Gly Gln Gly Thr Leu Val
210                 215                 220
Thr Val Ser Ser Gly Gly Cys Gly Gly Gly Glu Val Ala Ala Cys Glu
225                 230                 235                 240
Lys Glu Val Ala Ala Leu Glu Lys Glu Val Ala Ala Leu Glu Lys Glu
                245                 250                 255
Val Ala Ala Leu Glu Lys Leu Glu Pro Lys Ser Ala Asp Lys Thr His
            260                 265                 270
Thr Cys Pro Pro Cys Pro Ala Pro Glu Ala Ala Gly Gly Pro Ser Val
        275                 280                 285
Phe Leu Phe Pro Pro Lys Pro Lys Asp Thr Leu Tyr Ile Thr Arg Glu
290                 295                 300
Pro Glu Val Thr Cys Val Val Val Asp Val Ser His Glu Asp Pro Glu
305                 310                 315                 320
Val Lys Phe Asn Trp Tyr Val Asp Gly Val Glu Val His Asn Ala Lys
                325                 330                 335
Thr Lys Pro Arg Glu Glu Gln Tyr Asn Ser Thr Tyr Arg Val Val Ser
            340                 345                 350
Val Leu Thr Val Leu His Gln Asp Trp Leu Asn Gly Lys Glu Tyr Lys
        355                 360                 365
Cys Lys Val Ser Asn Lys Ala Leu Pro Ala Pro Ile Glu Lys Thr Ile
370                 375                 380
Ser Lys Ala Lys Gly Gln Pro Arg Glu Pro Gln Val Tyr Thr Leu Pro
385                 390                 395                 400
Pro Ser Arg Glu Glu Met Thr Lys Asn Gln Val Ser Leu Thr Cys Leu
                405                 410                 415
Val Lys Gly Phe Tyr Pro Ser Asp Ile Ala Val Glu Trp Glu Ser Asn
            420                 425                 430
Gly Gln Pro Glu Asn Asn Tyr Lys Thr Thr Pro Pro Val Leu Asp Ser
        435                 440                 445
Asp Gly Ser Phe Phe Leu Tyr Ser Lys Leu Thr Val Asp Lys Ser Arg
450                 455                 460
Trp Gln Gln Gly Asn Val Phe Ser Cys Ser Val Met His Glu Ala Leu
```

His Asn His Tyr Thr Gln Lys Ser Leu Ser Leu Ser Pro Gly
                485                 490

<210> SEQ ID NO 26
<211> LENGTH: 1482
<212> TYPE: DNA
<213> ORGANISM: Artificial Sequence
<220> FEATURE:
<223> OTHER INFORMATION: Polynucleotide Encoding the First and Third
      Polypeptide Chains of the Exemplary PD-1 x LAG-3 Fc-DART-1 diabody

<400> SEQUENCE: 26

```
gaaattgtcc tgacacagtc tcccgcaacc ctgagtttga gtcctgggga gcgagcaact        60
ctctcctgcc gagcctccca gagtatctcc tcctacctcg cctggtacca acagaagcca       120
gggcaggctc caaggctgct tatctatgac gcctctaacc gcgcaactgg gattcccgca       180
cgcttctccg gctctggttc cggcacagac tttacactta ctatctctag cctggagcca       240
gaagactttg ccgtgtacta ttgtcagcaa cgttccaatt ggccccttac ctttgggcag       300
ggcactaact tggaaatcaa aggtggcgga tccggcggcg gaggccaggt tcagctggtc       360
gagagtggtg gcgcgttgt gcaacctggg cgttccctcc gattggactg taaagcttcc       420
ggcattactt tctcaaattc cggcatgcat tgggtgaggc aagcccctgg aaaagggctc       480
gaatgggtgg ctgtgatttg gtacgatggc agcaaacggt actacgccga ttctgttaag       540
ggccgcttta ccatctcccg cgataactca agaacacac tgtttctgca aatgaatagt       600
cttagagccg aggacaccgc cgtgtactac tgtgccacaa atgacgatta ttggggcag       660
ggcacattgg tcacagtgtc ttccggagga tgtggcggtg agaagtggc cgcatgtgag       720
aaagaggttg ctgctttgga aaggaggtc gctgcacttg aaaaggaggt cgcagccctg       780
gagaaactgg agcccaaatc tgctgacaaa actcacacat gcccaccgtg cccagcacct       840
gaagccgcgg gggaccgtc agtcttcctc ttccccccaa acccaaggga caccctctat       900
atcacccggg agcctgaggt cacatgcgtg gtggtggacg tgagccacga agaccctgag       960
gtcaagttca actggtacgt ggacggcgtg gaggtgcata atgccaagac aaagccgcgg      1020
gaggagcagt acaacagcac gtaccgtgtg gtcagcgtcc tcaccgtcct gcaccaggac      1080
tggctgaatg gcaaggagta caagtgcaag gtctccaaca aagccctccc agcccccatc      1140
gagaaaacca tctccaaagc caaagggcag ccccgagaac acaggtgta caccctgccc      1200
ccatcccggg aggagatgac caagaaccag gtcagcctga cctgcctggt caaaggcttc      1260
tatcccagcg acatcgccgt ggagtgggag agcaatgggc agccggagaa caactacaag      1320
accacgcctc ccgtgctgga ctccgacggc tccttcttcc tctacagcaa gctcaccgtg      1380
gacaagagca ggtggcagca ggggaacgtc ttctcatgct ccgtgatgca tgaggctctg      1440
cacaaccact acacgcagaa gagcctctcc ctgtctccgg gt                         1482
```

<210> SEQ ID NO 27
<211> LENGTH: 269
<212> TYPE: PRT
<213> ORGANISM: Artificial Sequence
<220> FEATURE:
<223> OTHER INFORMATION: Second and Fourth Polypeptide Chains of the
      Exemplary PD-1 x LAG-3 Fc-DART-1 diabody

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Gly Gly Gly Ser Gly
            100                 105                 110

Gly Gly Gly Gln Val Gln Leu Gln Gln Trp Gly Ala Gly Leu Leu Lys
        115                 120                 125

Pro Ser Glu Thr Leu Ser Leu Thr Cys Ala Val Tyr Gly Gly Ser Phe
    130                 135                 140

Ser Asp Tyr Tyr Trp Asn Trp Ile Arg Gln Pro Pro Gly Lys Gly Leu
145                 150                 155                 160

Glu Trp Ile Gly Glu Ile Asn His Asn Gly Asn Thr Asn Ser Asn Pro
                165                 170                 175

Ser Leu Lys Ser Arg Val Thr Leu Ser Leu Asp Thr Ser Lys Asn Gln
            180                 185                 190

Phe Ser Leu Lys Leu Arg Ser Val Thr Ala Ala Asp Thr Ala Val Tyr
        195                 200                 205

Tyr Cys Ala Phe Gly Tyr Ser Asp Tyr Glu Tyr Asn Trp Phe Asp Pro
    210                 215                 220

Trp Gly Gln Gly Thr Leu Val Thr Val Ser Ser Gly Gly Cys Gly Gly
225                 230                 235                 240

Gly Lys Val Ala Ala Cys Lys Glu Lys Val Ala Ala Leu Lys Glu Lys
            245                 250                 255

Val Ala Ala Leu Lys Glu Lys Val Ala Ala Leu Lys Glu
            260                 265

<210> SEQ ID NO 28
<211> LENGTH: 807
<212> TYPE: DNA
<213> ORGANISM: Artificial Sequence
<220> FEATURE:
<223> OTHER INFORMATION: Polynucleotide Encoding the Second and Fourth
      Polypeptide Chains of the Exemplary PD-1 x LAG-3 Fc-DART-1 diabody

<400> SEQUENCE: 28
gagatcgtac ttacccagtc tcccgccacc ctttccctga gtcctggtga gcgggccact      60
ctttcctgtc gcgcaagcca atcagtttct agctacctcg catggtatca gcagaagcca     120
gggcaggcac ccaggcttct catctatgac gccagtaacc gcgcaaccgg gatacctgct     180
agattttccg gcagtggatc tgggaccgat ttcacactga caatttcatc cttggaacca     240
gaagatttcg cagtctacta ctgccagcaa tcttccaact ggccaagaac tttcggacag     300
gggaccaaag tggaaattaa aggtggcgga tccggcggcg gaggcaggt ccagctccag      360 caatggggag ccgggctgct gaaaccctct gaaacactga gtctcacatg tgccgtttat     420
ggaggttcct tctccgatta ttactggaac tggattcgtc agcctcccgg caagggcctg     480
gagtggatcg gtgagattaa ccacaatggc aataccaata gcaatcctag tttgaaatct     540
cgcgtcactc tttccctcga tacaagcaaa aaccagtttt ctttgaaatt gcgatctgta     600

```
actgctgctg atactgccgt gtattactgc gcattcggct actccgacta tgaatataat    660
tggttcgatc cttggggaca gggaacattg gtaaccgtgt catccggagg atgtggcggt    720
ggaaaagtgg ccgcatgtaa ggagaaagtt gctgctttga agagaaaggt cgccgcactt    780
aaggaaaagg tcgcagccct gaaagag                                        807
```

<210> SEQ ID NO 29
<211> LENGTH: 501
<212> TYPE: PRT
<213> ORGANISM: Artificial Sequence
<220> FEATURE:
<223> OTHER INFORMATION: First and Third Polypeptide Chains of the
      Exemplary PD-1 x LAG-3 Fc-DART-2 diabody

<400> SEQUENCE: 29

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Gly Gly Gly Ser Gly
            100                 105                 110

Gly Gly Gly Gln Val Gln Leu Gln Gln Trp Gly Ala Gly Leu Leu Lys
        115                 120                 125

Pro Ser Glu Thr Leu Ser Leu Thr Cys Ala Val Tyr Gly Gly Ser Phe
    130                 135                 140

Ser Asp Tyr Tyr Trp Asn Trp Ile Arg Gln Pro Pro Gly Lys Gly Leu
145                 150                 155                 160

Glu Trp Ile Gly Glu Ile Asn His Asn Gly Asn Thr Asn Ser Asn Pro
                165                 170                 175

Ser Leu Lys Ser Arg Val Thr Leu Ser Leu Asp Thr Ser Lys Asn Gln
            180                 185                 190

Phe Ser Leu Lys Leu Arg Ser Val Thr Ala Ala Asp Thr Ala Val Tyr
        195                 200                 205

Tyr Cys Ala Phe Gly Tyr Ser Asp Tyr Glu Tyr Asn Trp Phe Asp Pro
    210                 215                 220

Trp Gly Gln Gly Thr Leu Val Thr Val Ser Ser Gly Gly Cys Gly Gly
225                 230                 235                 240

Gly Glu Val Ala Ala Cys Glu Lys Glu Val Ala Ala Leu Glu Lys Glu
                245                 250                 255

Val Ala Ala Leu Glu Lys Glu Val Ala Ala Leu Glu Lys Leu Glu Pro
            260                 265                 270

Lys Ser Ala Asp Lys Thr His Thr Cys Pro Pro Cys Pro Ala Pro Glu
        275                 280                 285

Ala Ala Gly Gly Pro Ser Val Phe Leu Phe Pro Pro Lys Pro Lys Asp
    290                 295                 300

Thr Leu Tyr Ile Thr Arg Glu Pro Glu Val Thr Cys Val Val Val Asp
305                 310                 315                 320
```

```
Val Ser His Glu Asp Pro Glu Val Lys Phe Asn Trp Tyr Val Asp Gly
            325                 330                 335

Val Glu Val His Asn Ala Lys Thr Lys Pro Arg Glu Glu Gln Tyr Asn
        340                 345                 350

Ser Thr Tyr Arg Val Val Ser Val Leu Thr Val Leu His Gln Asp Trp
    355                 360                 365

Leu Asn Gly Lys Glu Tyr Lys Cys Lys Val Ser Asn Lys Ala Leu Pro
370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly
            500

<210> SEQ ID NO 30
<211> LENGTH: 1503
<212> TYPE: DNA
<213> ORGANISM: Artificial Sequence
<220> FEATURE:
<223> OTHER INFORMATION: Polynucleotide Encoding the First and Third
      Polypeptide Chains of the Exemplary PD-1 x LAG-3 Fc-DART-2 diabody

<400> SEQUENCE: 30
gagatcgtac ttacccagtc tcccgccacc ctttccctga gtcctggtga gcgggccact      60
ctttcctgtc gcgcaagcca atcagttttc agctacctcg catggtatca gcagaagcca     120
gggcaggcac ccaggcttct catctatgac gccagtaacc gcgcaaccgg gatacctgct     180
agattttccg gcagtggatc tgggaccgat ttcacactga caatttcatc cttggaacca     240
gaagatttcg cagtctacta ctgccagcaa tcttccaact ggccaagaac tttcggacag     300
gggaccaaag tggaaattaa aggtggcgga tccggcggcg gaggccaggt ccagctccag     360
caatggggag ccgggctgct gaaaccctct gaaacactga gtctcacatg tgccgtttat     420
ggaggttcct tctccgatta ttactggaac tggattcgtc agcctccggg caagggcctg     480
gagtggatcg gtgagattaa ccacaatggc aataccaata gcaatcctag tttgaaatct     540
cgcgtcactc tttccctcga tacaagcaaa accagttttt ctttgaaatt gcgatctgta     600
actgctgctg atactgccgt gtattactgc gcattcggct actccgacta tgaatataat     660
tggttcgatc cttggggaca gggaacattg gtaaccgtgt catccggagg atgtggcggt     720
ggagaagtgg ccgcatgtga aaagaggtt gctgctttgg agaaggaggt cgctgcactt     780
gaaaaggagg tcgcagccct ggagaaactg agcccaaat ctgctgacaa aactcacaca     840
tgcccaccgt gcccagcacc tgaagccgcg ggggaccgt cagtcttcct cttccccca      900 aaacccaagg acaccctcta tatcacccgg gagcctgagg tcacatgcgt ggtggtggac     960
```

```
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggagt acaagtgcaa ggtctccaac    1140
aaagccctcc cagcccccat cgagaaaacc atctccaaag ccaagggca gccccgagaa     1200 ccacaggtgt acaccctgcc cccatcccgg gaggagatga ccaagaacca ggtcagcctg    1260
acctgcctgg tcaaaggctt ctatcccagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggt                                                                  1503
```

<210> SEQ ID NO 31
<211> LENGTH: 262
<212> TYPE: PRT
<213> ORGANISM: Artificial Sequence
<220> FEATURE:
<223> OTHER INFORMATION: Second and Fourth Polypeptide Chains of the
      Exemplary PD-1 x LAG-3 Fc-DART-2 diabody

<400> SEQUENCE: 31

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Asp Cys Lys Ala Ser Gly Ile Thr Phe
    130                 135                 140

Ser Asn Ser Gly Met His Trp Val Arg Gln Ala Pro Gly Lys Gly Leu
145                 150                 155                 160

Glu Trp Val Ala Val Ile Trp Tyr Asp Gly Ser Lys Arg Tyr Tyr Ala
                165                 170                 175

Asp Ser Val Lys Gly Arg Phe Thr Ile Ser Arg Asp Asn Ser Lys Asn
            180                 185                 190

Thr Leu Phe Leu Gln Met Asn Ser Leu Arg Ala Glu Asp Thr Ala Val
        195                 200                 205

Tyr Tyr Cys Ala Thr Asn Asp Asp Tyr Trp Gly Gln Gly Thr Leu Val
    210                 215                 220

Thr Val Ser Ser Gly Gly Cys Gly Gly Gly Lys Val Ala Ala Cys Lys
225                 230                 235                 240

Glu Lys Val Ala Ala Leu Lys Glu Lys Val Ala Ala Leu Lys Glu Lys
                245                 250                 255
```

Val Ala Ala Leu Lys Glu
            260

<210> SEQ ID NO 32
<211> LENGTH: 786
<212> TYPE: DNA
<213> ORGANISM: Artificial Sequence
<220> FEATURE:
<223> OTHER INFORMATION: Polynucleotide Encoding the Second and Fourth
      Polypeptide Chains of the Exemplary PD-1 x LAG-3 Fc-DART-2 diabody

<400> SEQUENCE: 32
gaaattgtcc tgacacagtc tcccgcaacc ctgagtttga gtcctgggga gcgagcaact      60
ctctcctgcc gagcctccca gagtatctcc tcctacctcg cctggtacca acagaagcca     120
gggcaggctc caaggctgct tatctatgac gcctctaacc gcgcaactgg gattcccgca     180
cgcttctccg gctctggttc cggcacagac tttacactta ctatctctag cctggagcca     240
gaagactttg ccgtgtacta ttgtcagcaa cgttccaatt ggccccttac ctttgggcag     300
ggcactaact tggaaatcaa aggtggcgga tccggcggcg gaggccaggt tcagctggtc     360
gagagtggtg gcgcgttgt gcaacctggg cgttccctcc gattggactg taaagcttcc     420
ggcattactt tctcaaattc cggcatgcat tgggtgaggc aagcccctgg aaaagggctc     480
gaatgggtgg ctgtgatttg gtacgatggc agcaaacggt actacgccga ttctgttaag     540
ggccgcttta ccatctcccg cgataactca aagaacacac tgtttctgca aatgaatagt     600
cttagagccg aggacaccgc cgtgtactac tgtgccacaa atgacgatta ttgggggcag     660
ggcacattgg tcacagtgtc ttccggagga tgtggcggtg gaaaagtggc cgcatgtaag     720
gagaaagttg ctgctttgaa agagaaggtc gccgcactta aggaaaaggt cgcagccctg     780
aaagag                                                                786

COVALENTLY BONDED DIABODIES HAVING IMMUNOREACTIVITY WITH PD-1 AND LAG-3, AND METHODS OF USE THEREOF

CROSS-REFERENCE TO RELATED APPLICATIONS

This application is a continuation of U.S. patent application Ser. No. 15/321,279 (filed Dec. 22, 2016), which application is a § 371 Application of PCT/US2015/036634 (filed Jun. 19, 2015), which application claims priority to U.S. Patent Application No. 62/017,467 (filed Jun. 26, 2014), each of which applications is herein incorporated by reference in its entirety

REFERENCE TO SEQUENCE LISTING

This application includes one or more Sequence Listings pursuant to 37 C.F.R. 1.821 et seq., which are disclosed in computer-readable media (file name: 1301_0115PCT_Sequence_Listing_ST25.txt, created on 2 Jun. 2015, and having a size of 50,015 bytes), which file is herein incorporated by reference in its entirety.

BACKGROUND OF THE INVENTION

Field of the Invention

The present invention is directed to bi-specific diabodies that comprise two or more polypeptide chains and which possess at least one Epitope-Binding Site that is immunospecific for an epitope of PD-1 and at least one Epitope-Binding Site that is immunospecific for an epitope of LAG-3 (i.e., a "PD-1×LAG-3 bi-specific diabody"). More preferably, the present invention is directed to bi-specific diabodies that comprise four polypeptide chains and which possess two Epitope-Binding Sites that are immunospecific for one (or two) epitope(s) of PD-1 and two Epitope-Binding Site that are immunospecific for one (or two) epitope(s) of LAG-3 (i.e., a "PD-1×LAG-3 bi-specific, tetra-valent diabody"). The present invention also is directed to such diabodies that additionally comprise an immunoglobulin Fc Domain ("bi-specific Fc diabodies" and "bi-specific, tetra-valent, Fc diabodies"). The diabodies of the present invention are capable of simultaneously binding to PD-1 and to LAG-3, particularly as such molecules are arrayed on the surfaces of human cells. The invention is directed to pharmaceutical compositions that contain such diabodies, and to methods involving the use of such diabodies in the treatment of cancer and other diseases and conditions.

Description of Related Art

I. Cell-Mediated Immune Responses

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, Natural Killer cells (NK), and antigen-specific cytotoxic T-lymphocytes by T-cells, and the release of various cytokines in response to the recognition of an antigen (Dong, C. et al. (2003) "*Immune Regulation by Novel Costimulatory Molecules,*" Immunolog. Res. 28(1): 39-48).

The ability of T-cells to optimally mediate an immune response against an antigen requires two distinct signaling interactions (Viglietta, V. et al. (2007) "*Modulating Co-Stimulation,*" Neurotherapeutics 4:666-675; Korman, A. J. et al. (2007) "*Checkpoint Blockade in Cancer Immunotherapy,*" Adv. Immunol. 90:297-339). First, antigen that has been arrayed on the surface of Antigen-Presenting Cells (APC) must be presented to an antigen-specific naive $CD4^+$ T-cell. Such presentation delivers a signal via the T-Cell Receptor (TCR) that directs the T-cell to initiate an immune response that will be specific to the presented antigen. Second, a series of co-stimulatory and inhibitory signals, mediated through interactions between the APC and distinct T-cell surface molecules, triggers first the activation and proliferation of the T-cells and ultimately their inhibition. Thus, the first signal confers specificity to the immune response whereas the second signal serves to determine the nature, magnitude and duration of the response.

The immune system is tightly controlled by costimulatory and co-inhibitory ligands and receptors. These molecules provide the second signal for T-cell activation and provide a balanced network of positive and negative signals to maximize immune responses against infection while limiting immunity to self (Wang, L. et al. (Mar. 7, 2011) "*VISTA, A Novel Mouse Ig Superfamily Ligand That Negatively Regulates T-Cell Responses,*" J. Exp. Med. 10.1084/jem.20100619:1-16; Lepenies, B. et al. (2008) "*The Role Of Negative Costimulators During Parasitic Infections,*" Endocrine, Metabolic & Immune Disorders—Drug Targets 8:279-288). Of particular importance is binding between the B7.1 (CD80) and B7.2 (CD86) ligands of the Antigen-Presenting Cell and the CD28 and CTLA-4 receptors of the $CD4^+$ T-lymphocyte (Sharpe, A. H. et al. (2002) "*The B7-CD28 Superfamily,*" Nature Rev. Immunol. 2:116-126; Dong, C. et al. (2003) "*Immune Regulation by Novel Costimulatory Molecules,*" Immunolog. Res. 28(1):39-48; Lindley, P. S. et al. (2009) "*The Clinical Utility Of Inhibiting CD28-Mediated Costimulation,*" Immunol. Rev. 229:307-321). Binding of B7.1 or of B7.2 to CD28 stimulates T-cell activation; binding of B7.1 or B7.2 to CTLA-4 inhibits such activation (Dong, C. et al. (2003) "*Immune Regulation by Novel Costimulatory Molecules,*" Immunolog. Res. 28(1): 39-48; Lindley, P. S. et al. (2009) "*The Clinical Utility Of Inhibiting CD28-Mediated Costimulation,*" Immunol. Rev. 229:307-321; Greenwald, R. J. et al. (2005) "*The B7 Family Revisited,*" Ann. Rev. Immunol. 23:515-548). CD28 is constitutively expressed on the surface of T-cells (Gross, J., et al. (1992) "*Identification And Distribution Of The Costimulatory Receptor CD28 In The Mouse,*" J. Immunol. 149: 380-388), whereas CTLA4 expression is rapidly up-regulated following T cell activation (Linsley, P. et al. (1996) "*Intracellular Trafficking Of CTLA4 And Focal Localization Towards Sites Of TCR Engagement,*" Immunity 4:535-543). Since CTLA4 is the higher affinity receptor (Sharpe, A.H. et al. (2002) "*The B7-CD28 Superfamily,*" Nature Rev. Immunol. 2:116-126), binding first initiates T-cell proliferation (via CD28) and then inhibits it (via nascent expression of CTLA4), thereby dampening the effect when proliferation is no longer needed.

Further investigations into the ligands of the CD28 receptor have led to the identification and characterization of a set of related B7 molecules (the "B7 Superfamily") (Coyle, A. J. et al. (2001) "*The Expanding B7 Superfamily: Increasing Complexity In Costimulatory Signals Regulating T-Cell*

Function," *Nature Immunol.* 2(3):203-209; Sharpe, A. H. et al. (2002) "*The B7-CD28 Superfamily,*" *Nature Rev. Immunol.* 2:116-126; Greenwald, R. J. et al. (2005) "*The B7 Family Revisited,*" *Ann. Rev. Immunol.* 23:515-548; Collins, M. et al. (2005) "*The B7 Family Of Immune-Regulatory Ligands,*" *Genome Biol.* 6:223.1-223.7; Loke, P. et al. (2004) "*Emerging Mechanisms Of Immune Regulation: The Extended B7 Family And Regulatory T-Cells.*" *Arthritis Res. Ther.* 6:208-214; Korman, A. J. et al. (2007) "*Checkpoint Blockade in Cancer Immunotherapy,*" *Adv. Immunol.* 90:297-339; Flies, D. B. et al. (2007) "*The New B7s: Playing a Pivotal Role in Tumor Immunity,*" *J. Immunother.* 30(3): 251-260; Agarwal, A. et al. (2008) "*The Role Of Positive Costimulatory Molecules In Transplantation And Tolerance,*" *Curr. Opin. Organ Transplant.* 13:366-372; Lenschow, D. J. et al. (1996) "*CD28/B7 System of T-Cell Costimulation,*" *Ann. Rev. Immunol.* 14:233-258; Wang, S. et al. (2004) "*Co-Signaling Molecules Of The B7-CD28 Family In Positive And Negative Regulation Of T Lymphocyte Responses,*" *Microbes Infect.* 6:759-766). There are currently several known members of the family: B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) "*The B7 Family Of Immune-Regulatory Ligands,*" *Genome Biol.* 6:223.1-223.7; Flajnik, M. F. et al. (2012) "*Evolution Of The B7 Family: Co-Evolution Of B7H6 And Nkp30, Identification Of A New B7 Family Member, B7H7, And Of B7's Historical Relationship With The MHC,*" *Immunogenetics* epub doi.org/10.1007/s00251-012-0616-2).

II. PD-1

Programmed Death-1 ("PD-1") is an approximately 31 kD type I membrane protein member of the extended CD28/CTLA4 family of T-cell regulators that broadly negatively regulates immune responses (Ishida, Y. et al. (1992) "*Induced Expression Of PD-1, A Novel Member Of The Immunoglobulin Gene Superfamily, Upon Programmed Cell Death,*" *EMBO J.* 11:3887-3895; United States Patent Application Publication No. 2007/0202100; 2008/0311117; 2009/00110667; U.S. Pat. Nos. 6,808,710; 7,101,550; 7,488, 802; 7,635,757; 7,722,868; PCT Publication No. WO 01/14557). Compared to CTLA4, PD-1 more.

PD-1 is expressed on activated T-cells, B cells, and monocytes (Agata, Y. et al. (1996) "*Expression Of The PD-1 Antigen On The Surface Of Stimulated Mouse T And B Lymphocytes,*" *Int. Immunol.* 8(5):765-772; Yamazaki, T. et al. (2002) "*Expression Of Programmed Death 1 Ligands By Murine T-Cells And APC,*" *J. Immunol.* 169:5538-5545) and at low levels in Natural Killer (NK) T-cells (Nishimura, H. et al. (2000) "*Facilitation Of Beta Selection And Modification Of Positive Selection In The Thymus Of PD-1-Deficient Mice,*" *J. Exp. Med.* 191:891-898; Martin-Orozco, N. et al. (2007) "*Inhibitory Costimulation And Anti-Tumor Immunity,*" *Semin. Cancer Biol.* 17(4):288-298).

The extracellular region of PD-1 consists of a single immunoglobulin (Ig)V domain with 23% identity to the equivalent domain in CTLA4 (Martin-Orozco, N. et al. (2007) "*Inhibitory Costimulation And Anti-Tumor Immunity,*" *Semin. Cancer Biol.* 17(4):288-298). The extracellular IgV domain is followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals (Ishida, Y. et al. (1992) "*Induced Expression Of PD-1, A Novel Member Of The Immunoglobulin Gene Superfamily, Upon Programmed Cell Death,*" *EMBO J.* 11:3887-3895; Blank, C. et al. (Epub 2006 Dec. 29) "*Contribution Of The PD-L1/PD-1Pathway To T-Cell Exhaustion: An Update On Implications For Chronic Infections And Tumor Evasion Cancer,*" *Immunol. Immunother.* 56(5):739-745).

PD-1 mediates its inhibition of the immune system by binding to B7-H1 and B7-DC (Flies, D.B. et al. (2007) "*The New B7s: Playing a Pivotal Role in Tumor Immunity,*" *J. Immunother.* 30(3):251-260; U.S. Pat. Nos. 6,803,192; 7,794,710; United States Patent Application Publication Nos. 2005/0059051; 2009/0055944; 2009/0274666; 2009/0313687; PCT Publication No. WO 01/39722; WO 02/086083).

B7-H1 and B7-DC are binding ligands that are broadly expressed on the surfaces of human and murine tissues, such as heart, placenta, muscle, fetal liver, spleen, lymph nodes, and thymus as well as murine liver, lung, kidney, islets cells of the pancreas and small intestine (Martin-Orozco, N. et al. (2007) "*Inhibitory Costimulation And Anti-Tumor Immunity,*" *Semin. Cancer Biol.* 17(4):288-298). In humans, B7-H1 protein expression has been found in human endothelial cells (Chen, Y. et al. (2005) "*Expression of B7-H1 in Inflammatory Renal Tubular Epithelial Cells,*" *Nephron. Exp. Nephrol.* 102:e81-e92; de Haij, S. et al. (2005) "*Renal Tubular Epithelial Cells Modulate T-Cell Responses Via ICOS-L And B7-H1*" *Kidney Int.* 68:2091-2102; Mazanet, M. M. et al. (2002) "*B7-H1 Is Expressed By Human Endothelial Cells And Suppresses T-Cell Cytokine Synthesis,*" *J. Immunol.* 169:3581-3588), myocardium (Brown, J. A. et al. (2003) "*Blockade Of Programmed Death-1 Ligands On Dendritic Cells Enhances T-Cell Activation And Cytokine Production,*" *J. Immunol.* 170:1257-1266), syncyciotrophoblasts (Petroff, M. G. et al. (2002) "*B7 Family Molecules: Novel Immunomodulators At The Maternal-Fetal Interface,*" *Placenta* 23:S95-S101). The molecules are also expressed by resident macrophages of some tissues, by macrophages that have been activated with interferon (IFN)-γ or tumor necrosis factor (TNF)-a (Latchman, Y. et al. (2001) "*PD-L2 Is A Second Ligand For PD-1 And Inhibits T-Cell Activation,*" *Nat. Immunol* 2:261-268), and in tumors (Dong, H. (2003) "*B7-H1 Pathway And Its Role In The Evasion Of Tumor Immunity,*" *J. Mol. Med.* 81:281-287).

The interaction between B7-H1 and PD-1 has been found to provide a crucial negative co-stimulatory signal to T and B cells (Martin-Orozco, N. et al. (2007) "*Inhibitory Costimulation And Anti-Tumor Immunity,*" *Semin. Cancer Biol.* 17(4):288-298) and functions as a cell death inducer (Ishida, Y. et al. (1992) "*Induced Expression Of PD-1, A Novel Member Of The Immunoglobulin Gene Superfamily, Upon Programmed Cell Death,*" *EMBO J.* 11:3887-3895; Subudhi, S. K. et al. (2005) "*The Balance Of Immune Responses: Costimulation Verse Coinhibition,*" *J. Molec. Med.* 83:193-202). More specifically, interaction between low concentrations of the PD-1 receptor and the B7-H1 ligand has been found to result in the transmission of an inhibitory signal that strongly inhibits the proliferation of antigen-specific $CD8^+$ T-cells; at higher concentrations the interactions with PD-1 do not inhibit T cell proliferation but markedly reduce the production of multiple cytokines (Sharpe, A. H. et al. (2002) "*The B7-CD28 Superfamily,*" *Nature Rev. Immunol.* 2:116-126). T cell proliferation and cytokine production by both resting and previously activated CD4 and CD8 T-cells, and even naive T-cells from umbilical-cord blood, have been found to be inhibited by soluble B7-H1-Fc fusion proteins (Freeman, G.J. et al. (2000)

"Engagement Of The PD-1 Immunoinhibitory Receptor By A Novel B7 Family Member Leads To Negative Regulation Of Lymphocyte Activation," J. Exp. Med. 192:1-9; Latchman, Y. et al. (2001) "PD-L2 Is A Second Ligand For PD-1 And Inhibits T-Cell Activation," Nature Immunol. 2:261-268; Carter, L. et al. (2002) "PD-1:PD-L inhibitory pathway affects both CD4(+) and CD8(+) T-cells and is overcome by IL-2," Eur. J. Immunol. 32(3):634-643; Sharpe, A. H. et al. (2002) "The B7-CD28 Superfamily," Nature Rev. Immunol. 2:116-126).

The role of B7-H1 and PD-1 in inhibiting T-cell activation and proliferation has suggested that these biomolecules might serve as therapeutic targets for treatments of inflammation and cancer. Thus, the use of anti-PD-1 antibodies to treat infections and tumors and up-modulate an adaptive immune response has been proposed (see, United States Patent Application Publication Nos. 2010/0040614; 2010/0028330; 2004/0241745; 2008/0311117; 2009/0217401; U.S. Pat. Nos. 7,521,051; 7,563,869; 7,595,048; PCT Publications Nos. WO 2004/056875; WO 2008/083174). Antibodies capable of immunospecifically binding to PD-1 have been reported by Agata, T. et al. (1996) "Expression Of The PD-1 Antigen On The Surface Of Stimulated Mouse T And B Lymphocytes," Int. Immunol. 8(5):765-772 and Berger, R. et al. (2008) "Phase I Safety And Pharmacokinetic Study Of CT-011, A Humanized Antibody Interacting With PD-1, In Patients With Advanced Hematologic Malignancies," Clin. Cancer Res. 14(10):3044-3051 (see, also, U.S. Pat. Nos. 8,008,449 and 8,552,154; US Patent Publications No. 2007/0166281; 2012/0114648; 2012/0114649; 2013/0017199; 2013/0230514 and 2014/0044738; and PCT Patent Publications WO 2003/099196; WO 2004/004771; WO 2004/056875; WO 2004/072286; WO 2006/121168; WO 2007/005874; WO 2008/083174; WO 2009/014708; WO 2009/073533; WO 2012/135408, WO 2012/145549 and WO 2013/014668).

III. LAG-3

Lymphocyte activation gene 3 (LAG-3, CD223) is a cell-surface receptor protein that is expressed by activated $CD4^+$ and $CD8^+$ T-cells and NK cells, and is constitutively expressed by plasmacytoid dendritic cells; LAG-3 is not expressed by B cells, monocytes or any other cell types tested (Workman, C.J. et al. (2009) "LAG-3 Regulates Plasmacytoid Dendritic Cell Homeostasis," J. Immunol. 182(4):1885-1891).

LAG-3 has been found to be closely related to the T-cell co-receptor CD4 (Grosso, J.F. et al. (2009) "Functionally Distinct LAG-3 and PD-1 Subsets on Activated and Chronically Stimulated CD8 T-Cells," J. Immunol. 182(11):6659-6669; Huang, C. T. et al. (2004) "Role Of LAG-3 In Regulatory T-Cells," Immunity 21:503-513; Workman, C. J. et al. (2009) "LAG-3 Regulates Plasmacytoid Dendritic Cell Homeostasis," J. Immunol. 182(4):1885-1891). Like CD4, LAG-3 also binds to MHC class II molecules but does so with significantly higher affinity (Workman, C. J. et al. (2002) "Phenotypic Analysis Of The Murine CD4-Related Glycoprotein, CD223 (LAG-3)," Eur. J. Immunol. 32:2255-2263; Huard, B. et al. (1995) "CD4/Major Histocompatibility Complex Class II Interaction Analyzed With CD4-And Lymphocyte Activation Gene-3 (LAG-3)-Ig Fusion Proteins," Eur. J. Immunol. 25:2718-2721; Huard, B. et al. (1994) "Cellular Expression And Tissue Distribution Of The Human LAG-3-Encoded Protein, An MHC Class II Ligand," Immunogenetics 39:213-217).

Studies have shown that LAG-3 plays an important role in negatively regulating T-cell proliferation, function and homeostasis (Workman, C. J. et al. (2009) "LAG-3 Regulates Plasmacytoid Dendritic Cell Homeostasis," J. Immunol. 182(4):1885-1891; Workman, C. J. et al. (2002) "Cutting Edge: Molecular Analysis Of The Negative Regulatory Function Of Lymphocyte Activation Gene-3," J. Immunol. 169:5392-5395; Workman, C. J. et al. (2003) "The CD4-Related Molecule, LAG-3 (CD223), Regulates The Expansion Of Activated T-Cells," Eur. J. Immunol. 33:970-979; Workman, C. J. (2005) "Negative Regulation Of T-Cell Homeostasis By Lymphocyte Activation Gene-3 (CD223)," J. Immunol. 174:688-695; Hannier, S. et al. (1998) "CD3/TCR Complex-Associated Lymphocyte Activation Gene-3 Molecules Inhibit CD3/TCR Signaling," J. Immunol. 161: 4058-4065; Huard, B. et al. (1994) "Lymphocyte-Activation Gene 3/Major Histocompatibility Complex Class II Interaction Modulates The Antigenic Response Of $CD4^+$ T Lymphocytes," Eur. J. Immunol. 24:3216-3221).

Studies have suggested that inhibiting LAG-3 function through antibody blockade can reverse LAG-3-mediated immune system inhibition and partially restore effector function (Grosso, J. F. et al. (2009) "Functionally Distinct LAG-3 and PD-1 Subsets on Activated and Chronically Stimulated CD8 T-Cells," J. Immunol. 182(11):6659-6669; Grosso, J. F. et al. (2007) "LAG-3 Regulates $CD8^+$ T-Cell Accumulation And Effector Function During Self And Tumor Tolerance," J. Clin. Invest. 117:3383-3392). LAG-3 has been found to negatively regulate T cell expansion via inhibition of T Cell Receptor (TCR) -induced calcium fluxes, and controls the size of the memory T cell pool (Matsuzaki, J. et al. (2010) "Tumor-Infiltrating NY-ESO-1-Specific CD8+ T-Cells Are Negatively Regulated By LAG-3 And PD-1 In Human Ovarian Cancer," Proc. Natl. Acad. Sci. (U.S.A.) 107(17):7875-7880; Workman C. J., et al. (2004) "Lymphocyte Activation Gene-3 (CD223) Regulates The Size Of The Expanding T-Cell Population Following Antigen Activation in vivo," J. Immunol. 172:5450-5455).

Despite prior advances, a need remains for improved compositions capable of more vigorously directing the body's immune system to attack cancer cells or pathogen-infected cells, especially at lower therapeutic concentrations. For although the adaptive immune system can be a potent defense mechanism against cancer and disease, it is often hampered by immune suppressive mechanisms in the tumor microenvironment, such as the expression of PD-1 and LAG-3. Coinhibitory molecules expressed by tumor cells, immune cells, and stromal cells in the tumor milieu can dominantly attenuate T-cell responses against cancer cells.

As described in detail below, the present invention addresses this need by providing PD-1×LAG-3 bi-specific, tetra-valent, diabodies. Such diabodies are capable of binding to PD-1 and LAG-3 cell-surface molecules that are present on the surfaces of exhausted and tolerant tumor-infiltrating lymphocytes, and of thereby impairing the ability of such cell-surface molecules to bind to their receptor ligands. As such, the PD-1×LAG-3 bi-specific diabodies of the present invention act to block PD-1 and LAG-3-mediated immune system inhibition, and thereby promote the continued activation of the immune system. This attribute permits such bi-specific diabodies to have utility in the treatment of cancer and pathogen-associated diseases and conditions. The invention is directed to such diabodies and to methods for their use.

BRIEF DESCRIPTION OF THE FIGURES

FIG. 9A shows the T-cell proliferative responses obtained using the preferred PD-1×LAG-3 bi-specific, tetra-valent diabodies of the present invention (PD-1×LAG-Fe-DART®-1 and PD-1×LAG-Fc-DART®-2), PD-1 mAb 1 (5C4; BMS-936558)), LAG-3 mAb 1 (25F7; BMS-986016, Medarex/BMS), soluble human LAG-3 (ShLAG-3), a control IgG, responder+stimulator cells (pan T cells and mature dendritic cells; R+S) and stimulator cells (mature dendritic cells; S). FIG. 9B shows the same data for PD-1×LAG-Fe-DART®-1 and PD-1×LAG-Fc-DART®-2, PD-1 mAb 1 (5C4; BMS-936558)), LAG-3 mAb 1(25F7; BMS-986016, Medarex/BMS), and PD-1 mAb 1(5C4; BMS-936558))+LAG-3 mAb 1 (25F7; BMS-986016, Medarex/BMS), using a different y-axis scale.

SUMMARY OF THE INVENTION

Figure 1:
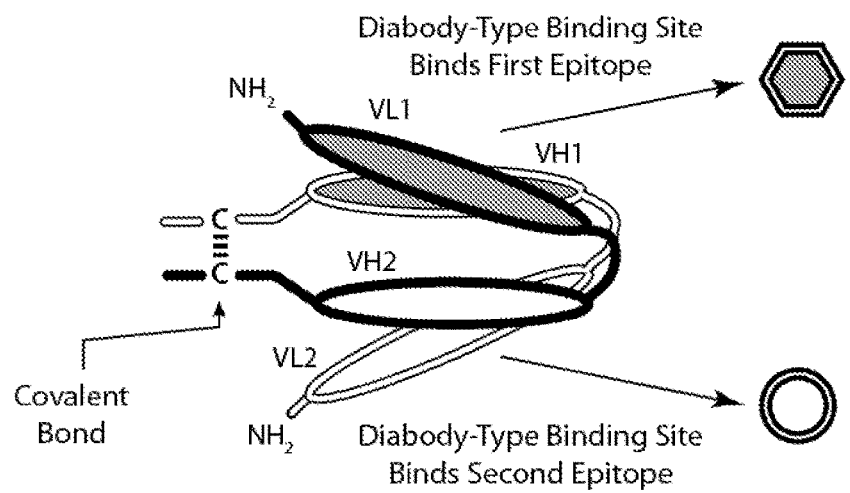
FIG. 1 shows a diagrammatic representation of the Domains of a basic DART®.

The present invention is directed to bi-specific diabodies that comprise two or more polypeptide chains and which possess at least one Epitope-Binding Site that is immunospecific for an epitope of PD-1 and at least one Epitope-Binding Site that is immunospecific for an epitope of LAG-3 (i.e., a "PD-1×LAG-3 bi-specific diabody"). More preferably, the present invention is directed to bi-specific diabodies that comprise four polypeptide chains and which possess two Epitope-Binding Sites that are immunospecific for one (or two) epitope(s) of PD-1 and two Epitope-Binding Site that are immunospecific for one (or two) epitope(s) of LAG-3 (i.e., a "PD-1×LAG-3 bi-specific, tetra-valent diabody"). The present invention also is directed to such diabodies that additionally comprise an immunoglobulin Fc Domain ("bi-specific Fc diabodies" and "bi-specific, tetra-valent, Fc diabodies"). The diabodies of the present invention are capable of simultaneously binding to PD-1 and to LAG-3, particularly as such molecules are arrayed on the surfaces of human cells. The invention is directed to pharmaceutical compositions that contain such diabodies, and to methods involving the use of such diabodies in the treatment of cancer and other diseases and conditions.

In detail, the invention provides a bi-specific Fc diabody capable of immunospecific binding to an epitope of PD-1 and to an epitope of LAG-3, wherein the diabody comprises four polypeptide chains, each having an amino terminus and a carboxy terminus, and wherein:

(A) the first and second polypeptide chains are covalently bonded to one another, the second and third polypeptide chains are covalently bonded to one another, and the third and fourth polypeptide chains are covalently bonded to one another;

(B) the first and third polypeptide chains of the diabody each comprise, in the N-terminal to C-terminal direction, a Light Chain Variable Domain of an antibody that is immunospecific for PD-1 or LAG-3, a Heavy Chain Variable Domain of an antibody that is immunospecific for LAG-3 or PD-1, a Heterodimer-Promoting Domain and a CH2—CH3 Domain, wherein the Light Chain Variable Domains and the Heavy Chain Variable Domains are incapable of associating to form an Epitope-Binding Site capable of binding an epitope of PD-1 or an epitope of LAG-3; and (C) the second and the fourth polypeptide chains of the diabody each comprise, in the N-terminal to C-terminal direction, a Light Chain Variable Domain of an antibody that is immunospecific for PD-1 or LAG-3, a Heavy Chain Variable Domain of an antibody that is immunospecific for LAG-3 or PD-1, and a Heterodimer-Promoting Domain, wherein the Light Chain Variable Domains and the Heavy Chain Variable Domains are incapable of associating to form an Epitope-Binding Site capable of binding an epitope of PD-1 or an epitope of LAG-3;

and wherein:

(I) (1) the Light Chain Variable Domain of the first polypeptide chain and the Heavy Chain Variable Domain of the second polypeptide chain associate to form a first Epitope-Binding Site and the Heavy Chain Variable Domain of the first polypeptide chain and the Light Chain Variable Domain of the second polypeptide chain associate to form a second Epitope-Binding Site; and (2) the Light Chain Variable Domain of the third polypeptide chain and the Heavy Chain Variable Domain of the fourth polypeptide chain associate to form a third Epitope-Binding Site and the Heavy Chain Variable Domain of the third polypeptide chain and the Light Chain Variable Domain of the fourth polypeptide chain associate to form a fourth Epitope-Binding Site;
wherein two of the formed Epitope-Binding Sites are capable of immunospecifically binding to an epitope of PD-1 and two of the formed Epitope-Binding Sites are capable of immunospecifically binding to an epitope of LAG-3;
II. the Heterodimer-Promoting Domains of the first and third polypeptide chains differ and have an amino acid sequence selected from the group consisting of: SEQ ID NO:16 and SEQ ID NO:17; and
III. the CH2—CH3 Domains of the first and third polypeptide chains associate to form an Fc Domain.

The invention also concerns the embodiment of such a bi-specific Fc diabody wherein the CH2—CH3 Domains of the first and third polypeptide chains each have the amino acid sequence of SEQ ID NO:24.

The invention also concerns the embodiment of such bi-specific Fc diabodies wherein the Heavy Chain Variable Domain of an antibody that is immunospecific for LAG-3 has the amino acid sequence of SEQ ID NO:11, and wherein the Light Chain Variable Domain of an antibody that is immunospecific for LAG-3 has the amino acid sequence of SEQ ID NO:12.

The invention also concerns the embodiment of such bi-specific Fc diabodies wherein the Heavy Chain Variable Domain of an antibody that is immunospecific for PD-1 has the amino acid sequence of SEQ ID NO:2, and wherein the Light Chain Variable Domain of an antibody that is immunospecific for PD-1 has the amino acid sequence of SEQ ID NO:3.

The invention also concerns a pharmaceutical composition that comprises an effective amount of any of the above-indicated Fc diabodies, and a pharmaceutically acceptable carrier.

The invention also concerns the embodiment of such a pharmaceutical composition wherein the effective amount of the bi-specific Fc diabody is an amount effective to treat cancer in a recipient individual in need of such treatment.

The invention also concerns the embodiment of such pharmaceutical compositions wherein the cancer is an adrenal gland cancer, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, or a uterine cancer.

The invention also concerns the embodiment of such pharmaceutical compositions wherein the effective amount of the bi-specific Fc diabody is an amount effective to treat a disease associated with the presence of a pathogen in a recipient individual in need of such treatment.

The invention also concerns the embodiment of such a pharmaceutical composition wherein the pathogen is a bacterium a fungus or a virus.

The invention also concerns a method of treating cancer which comprises administering an effective amount of such pharmaceutical compositions to an individual in need thereof.

The invention also concerns a method of treating a disease associated with the presence of a pathogen which comprises administering an effective amount of the pharmaceutical composition of any of claims 8-9 to an individual in need thereof.

DETAILED DESCRIPTION OF THE INVENTION

The present invention is directed to bi-specific diabodies that comprise two or more polypeptide chains and which possess at least one Epitope-Binding Site that is immunospecific for an epitope of PD-1 and at least one Epitope-Binding Site that is immunospecific for an epitope of LAG-3 (i.e., a "PD-1×LAG-3 bi-specific diabody"). More preferably, the present invention is directed to bi-specific diabodies that comprise four polypeptide chains and which possess two Epitope-Binding Sites that are immunospecific for one (or two) epitope(s) of PD-1 and two Epitope-Binding Site that are immunospecific for one (or two) epitope(s) of LAG-3 (i.e., a "PD-1×LAG-3 bi-specific, tetra-valent diabody"). The present invention also is directed to such diabodies that additionally comprise an immunoglobulin Fc Domain ("bi-specific Fc diabodies" and "bi-specific, tetravalent, Fc diabodies"). The diabodies of the present invention are capable of simultaneously binding to PD-1 and to LAG-3, particularly as such molecules are arrayed on the surfaces of human cells. The invention is directed to pharmaceutical compositions that contain such diabodies, and to methods involving the use of such diabodies in the treatment of cancer and other diseases and conditions.

The bi-specific diabodies of the present invention are capable of simultaneously binding to PD-1 and to LAG-3, particularly as such molecules are arrayed on the surfaces of human cells. The invention is directed to pharmaceutical compositions that contain such diabodies, and to methods involving the use of such diabodies in the treatment of cancer and other diseases and conditions. In particular, the PD-1×LAG-3 bi-specific diabodies of the present invention comprise polypeptide chains that are covalently complexed together.

As discussed above, T-cell activation requires two distinct signals. The first signal is provided by the T-Cell Receptor (TCR) expressed on the surface of a T-cell that has recognized a peptide antigen within the context of human leukocyte antigens (HLA) expressed on an Antigen-Presenting Cell (APCs). The second signal is provided by the interaction of cognate pairs of co-stimulatory ligands: B7-1 and B7-2 expressed on APCs and their corresponding receptors: CD28 and CTLA-4 expressed on T-cells.

Within this receptor-ligand axis, engagement of B7-co-stimulator molecules with the CD28 receptor can stimulate T-cell proliferation and subsequently induce the expression of CTLA-4, a negative-regulator and counter-receptor to CD28 that strongly competes for B7-1 and B7-2 ligands so as to "wind down" T-cell activation and proliferative responses. Agonist antibodies that bind CD28 have been shown to induce T-cell effector function and enhance the generation of tumor eradicating immunity and are co-stimulatory in nature. Conversely, antagonists that block CTLA-4 engagement can prevent T-cells from disengaging their effector function while maintaining sustained proliferation that can lead to autoimmunity.

In parallel with the CTLA-4:B7-1/B7-2 axis, which functions to activate the immune system during normal homeostasis and in the priming phase of an immune response against an antigen, a second receptor-ligand axis functions to inhibit the immune system, thereby serving as a counterpoint to CTLA-4 during the effector phase of an immune response. This second axis involves the binding of the programmed cell death-1 protein (PD-1) receptor, expressed on the surface of T-cells, to its corresponding ligands: PD-L1 and PD-L2, expressed on Antigen-Presenting Cells (APCs) and epithelial cells, respectively (Chen L. et al. (2013) "*Molecular Mechanisms Of T-Cell Co-Stimulation And Co-Inhibition,*" Nature Reviews Immunology 13(4):227-242). In contrast to agonist antibodies that bind to CD28 to stimulate T-cell responses, antibodies that bind to either PD-1 or PD-L1 antagonize or block PD-1/PD-L1 engagement are capable of maintaining T-cell responses by preventing the delivery of a negative signal toward T-cell. This augments or maintains T-cell proliferation, cytotoxicity, and cytokine secretion. Taken together agonist antibodies, such as anti-CD28, target positive signal pathways and are therefore co-stimulators, while antagonistic antibodies, such as anti-PD-1, target negative signal pathways and are called checkpoint inhibitors.

Although, CTLA-4 and PD-1 represent the canonical checkpoint inhibitors, there exists a growing family of immune modulating receptor-ligand pairs. Lymphocyte activation gene-3 (LAG-3), discussed above, is an additional checkpoint inhibitor target expressed on T-cells that binds to HLA-class II molecules expressed on APCs. LAG-3 is co-expressed with PD-1 on exhausted and tolerant tumor-infiltrating lymphocytes ("TILs") (Matsuzaki, J. et al. (2010) "*Tumor-Infiltrating NY-ESO-1-Specific CD8+ T-Cells Are Negatively Regulated by LAG-3 and PD-1 in Human Ovarian Cancer,*" Proc. Natl. Acad. Sci. (U.S.A.) 107(17):7875-7880; Okazaki, T. et al. (2011) "PD-1 and LAG-3 inhibitor Coreceptors Act Synergistically To Prevent Autoimmunity In Mice," J. Exp. Med. 208(2):395-407), and LAG-3 expression has been reported on T-regulatory cells implicating a role in both tumor immunology and autoimmunity. Animal models have demonstrated that anti-LAG-3 induces potent tumor eradicating immunity sufficient to slow tumor growth, and when given in combination with anti-PD-1 mAb can even trigger complete tumor regression (Woo, S. R. et al. (2012) "Immune Inhibitory Molecules LAG-3 And PD-1 Synergistically Regulate T-Cell Function To Promote Tumoral Immune Escape," Cancer Res. 72(4):917-927). Combination therapies involving anti-LAG-3 mAb BMS-986016 are currently under early-phase clinical investigation either alone or in combination with anti-PD-1 mAb (nivolumab/BMS-936558) (see, Creelan, B. C. (2014) "Update on Immune Checkpoint Inhibitors in Lung Cancer," Cancer Control 21(1):80-89).

The bi-specific diabodies of the present invention are capable of binding to PD-1 and LAG-3 cell-surface molecules that are present on the surfaces of exhausted and tolerant tumor-infiltrating lymphocytes, and of thereby impairing the ability of such cell-surface molecules to bind to their receptor ligands. As such, the PD-1×LAG-3 bi-specific diabodies of the present invention are able to attenuate PD-1 and LAG-3-mediated immune system inhibition, and promote continued immune system activation.

I. General Techniques and General Definitions

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, MOLECULAR CLONING: A LABORATORY MANUAL, Third Edition (Sambrook et al. Eds., 2001) Cold Spring Harbor Press, Cold Spring Harbor, N.Y.; OLIGONUCLEOTIDE SYNTHESIS: METHODS AND APPLICATIONS (Methods in Molecular Biology), Herdewijn, P., Ed., Humana Press, Totowa, N.J.; OLIGONUCLEOTIDE SYNTHESIS (Gait, M. J., Ed., 1984); METHODS IN MOLECULAR BIOLOGY, Humana Press, Totowa, N.J.; CELL BIOLOGY: A LABORATORY NOTEBOOK (Cellis, J. E., Ed., 1998) Academic Press, New York, N.Y.; ANIMAL CELL CULTURE (Freshney, R. I., Ed., 1987); INTRODUCTION TO CELL AND TISSUE CULTURE (Mather, J. P. and Roberts, P. E., Eds., 1998) Plenum Press, New York, N.Y.; CELL AND TISSUE CULTURE: LABORATORY PROCEDURES (Doyle, A. et al., Eds., 1993-8) John Wiley and Sons, Hoboken, N.J.; METHODS IN ENZYMOLOGY (Academic Press, Inc.) New York, N.Y.; WEIR'S HANDBOOK OF EXPERIMENTAL IMMUNOLOGY (Herzenberg, L. A. et al. Eds. 1997) Wiley-Blackwell Publishers, New York, N.Y.; GENE TRANSFER VECTORS FOR MAMMALIAN CELLS (Miller, J. M. et al. Eds., 1987) Cold Spring Harbor Press, Cold Spring Harbor, N.Y.; CURRENT PROTOCOLS IN MOLECULAR BIOLOGY (Ausubel, F. M. et al., Eds., 1987) Greene Pub. Associates, New York, N.Y.; PCR: THE POLYMERASE CHAIN REACTION, (Mullis, K. et al., Eds., 1994) Birkhäuser, Boston Mass.; CURRENT PROTOCOLS IN IMMUNOLOGY (Coligan, J. E. et al., eds., 1991) John Wiley and Sons, Hoboken, N.J.; SHORT PROTOCOLS IN MOLECULAR BIOLOGY (John Wiley and Sons, 1999) Hoboken, N.J.; IMMUNOBIOLOGY 7 (Janeway, C. A. et al. 2007) Garland Science, London, UK; Antibodies (P. Finch, 1997) Stride Publications, Devoran, UK; ANTIBODIES: A PRACTICAL APPROACH (D. Catty., ed., 1989) Oxford University Press, USA, New York N.Y.); MONOCLONAL ANTIBODIES: A PRACTICAL APPROACH (Shepherd, P. et al. Eds., 2000) Oxford University Press, USA, New York N.Y.; USING ANTIBODIES: A LABORATORY MANUAL (Harlow, E. et al. Eds., 1998) Cold Spring Harbor Laboratory Press, Cold Spring Harbor, N.Y.; THE ANTIBODIES (Zanetti, M. et al. Eds. 1995) Harwood Academic Publishers, London, UK); and DEVITA, HELLMAN, AND ROSENBERG'S CANCER: PRINCIPLES & PRACTICE OF ONCOLOGY, EIGHTH EDITION, DeVita, V. et al. Eds. 2008, Lippincott Williams & Wilkins, Philadelphia, Pa.

As used herein, "antibodies" are immunoglobulin molecules capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also mutants thereof, naturally occurring variants, fusion proteins comprising an antibody portion with an antigen recognition site of the required specificity, humanized antibodies, and chimeric antibodies, and any other modified configuration of the immunoglobulin molecule that comprises an antigen recognition site of the required specificity. Naturally occurring antibodies typically comprise two copies of a "heavy" ("H") polypeptide chain and two copies of a "light" ("L") polypeptide chain. Each light chain is comprised of a Light Chain Variable Region ("VL") and a light chain constant region ("CL"), Each heavy chain is comprised of a Heavy Chain Variable Region ("VH") and a heavy chain constant region, usually comprised of three domains (CH1, CH2 and CH3). The CH2 and CH3 Domains of the heavy chain polypeptides interact with one another to form an Fc region that is capable of binding to Fc receptors present on the surfaces of immune system cells.

The ability of an intact, unmodified antibody (e.g., an IgG) to bind an epitope of an antigen depends upon the presence of variable Domains on the immunoglobulin light and heavy chains (i.e., the VL and VH Domains, respectively). Interaction of an antibody light chain and an antibody heavy chain and, in particular, interaction of its VL and VH Domains forms one of the epitope-binding sites of the antibody. In contrast, an "scFv" fragment of an antibody comprises a VL and VH Domain of an antibody contained in a single polypeptide chain wherein the Domains are separated by a flexible linker of sufficient length to allow self-assembly of the two Domains into a functional Epitope-Binding Site.

Where self-assembly of the VL and VH Domains is rendered impossible due to a linker of insufficient length (less than about 12 amino acid residues), two of the scFv constructs interact with one another other to form a "diabody," which is a bi-valent molecule in which the VL of one chain associates with the VH of the other (reviewed in Marvin et al. (2005) "*Recombinant Approaches To IgG-Like Bispecific Antibodies,*" *Acta Pharmacol. Sin.* 26:649-658).

In addition to their known uses in diagnostics, antibodies have been shown to be useful as therapeutic agents. The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases,*" *Singapore Med. J.* 50(7):663-666). Nearly 200 antibody-based drugs have been approved for use or are under development.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term monoclonal antibody encompasses not only intact monoclonal antibodies and full-length monoclonal antibodies, but also fragments thereof (such as Fab, Fab', F(ab')$_2$ Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity,*" *Nature* 256:495-497 or a modification thereof.

Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi. In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the bi-specific molecules of the invention as well as a chimeric antibody, a humanized antibody, or a caninized antibody, to improve the affinity, or other characteristics of the antibody. The general principle in humanizing an antibody involves retaining the basic sequence of the epitope-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable Domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

Natural antibodies are capable of binding to only one epitope species (i.e., they are mono-specific), although they can bind multiple copies of that species (i.e., exhibiting bi-valency or multi-valency). A wide variety of recombinant bi-specific antibody formats have been developed (see, e.g., PCT Publication Nos. WO 2008/003116, WO 2009/132876, WO 2008/003103, WO 2007/146968), most of which use linker peptides either to fuse the antibody core (IgA, IgD, IgE, IgG or IgM) to a further binding protein (e.g. scFv) or to fuse e.g. two Fab fragments or scFv. Typically, such approaches involve compromises and trade-offs. For example, PCT Publications Nos. WO 2013/174873, WO 2011/133886 and WO 2010/136172 disclose that the use of linkers may cause problems in therapeutic settings, and teaches a tri-specific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publications Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publications Nos. WO 2010/028797, WO2010028796 and WO 2010/028795 disclose recombinant antibodies whose Fc Regions have been replaced with additional VL and VH Domains, so as to form tri-valent binding molecules. PCT Publications Nos. WO 2003/025018 and WO2003012069 disclose recombinant diabodies whose individual chains contain scFv domains. PCT Publications No. WO 2013/006544 discloses multi-valent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publications Nos. WO 2014/022540, WO 2013/003652, WO 2012/162583, WO 2012/156430, WO 2011/086091, WO 2007/075270, WO 1998/002463, WO 1992/022583 and WO 1991/003493 disclose adding additional Binding Domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

The art has additionally noted the ability to produce diabodies that differ from natural antibodies in being capable of binding two or more different epitope species (i.e., exhibiting bi-specificity or multispecificity in addition to bi-valency or multi-valency) (see, e.g., Holliger et al. (1993) "'Diabodies': Small Bivalent And Bispecific Antibody Fragments," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20): 19665-19672; WO 02/02781 (Mertens et al.); Olafsen, T. et al. (2004) "Covalent Disulfide-Linked Anti-CEA Diabody Allows Site-Specific Conjugation And Radiolabeling For Tumor Targeting Applications," Protein Eng Des Sel. 17(1): 21-27; Wu, A. et al. (2001) "Multimerization Of A Chimeric Anti-CD20 Single Chain Fv-Fv Fusion Protein Is Mediated Through Variable Domain Exchange," Protein Engineering 14(2):1025-1033; Asano et al. (2004) "A Diabody For Cancer Immunotherapy And Its Functional Enhancement By Fusion Of Human Fc Domain," Abstract 3P-683, J. Biochem. 76(8):992; Takemura, S. et al. (2000) "Construction Of A Diabody (Small Recombinant Bispecific Antibody) Using A Refolding System," Protein Eng. 13(8):583-588; Baeuerle, P.A. et al. (2009) "Bispecific T-Cell Engaging Antibodies For Cancer Therapy," Cancer Res. 69(12):4941-4944).

The design of a diabody is based on the single-chain variable region fragments (scFv). Such molecules are made by linking light and/or heavy chain variable regions by using a short linking peptide. Bird et al. (1988) ("Single-Chain Antigen-Binding Proteins," Science 242:423-426) describes example of linking peptides which bridge approximately 3.5 nm between the carboxy terminus of one variable region and the amino terminus of the other variable region. Linkers of other sequences have been designed and used (Bird et al. (1988) "Single-Chain Antigen-Binding Proteins," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

U.S. Pat. No. 7,585,952 and United States Patent Publication No. 2010-0173978 concern scFv molecules that are immunospecific for ErbB2. Bi-specific T-cell engagers ("BITES"), a type of scFv molecule has been described (WO 05/061547; Baeuerle, P et al. (2008) "BiTE: A New Class Of Antibodies That Recruit T-Cells," Drugs of the Future 33: 137-147; Bargou, et al. 2008) "Tumor Regression in Cancer Patients by Very Low Doses of a T-Cell-Engaging Antibody," Science 321: 974-977). Such molecules are composed of a single polypeptide chain molecule having two antigen-binding domains, one of which immunospecifically binds to a CD3 epitope and the second of which immunospecifically binds to an antigen present on the surface of a target cell.

The provision of non-mono-specific diabodies provides a significant advantage: the capacity to co-ligate and co-localize different epitopes. Bi-valent diabodies thus have wide-ranging applications including therapy and immuno-diagnosis. Bi-valency allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "Improved Tumour Targeting By Disulphide Stabilized Diabodies Expressed In Pichia pastoris," Protein Eng. 10:1221).

The bi-valency of diabodies has led to their use to co-ligate differing cells, for example, cross-linking cytotoxic T-cells to tumor cells (Staerz et al. (1985) "Hybrid Antibodies Can Target Sites For Attack By T-Cells," Nature 314: 628-631, and Holliger et al. (1996) "Specific Killing Of Lymphoma Cells By Cytotoxic T-Cells Mediated By A Bispecific Diabody," Protein Eng. 9:299-305). Thus, for example, diabody Epitope-Binding Domains may be directed to a surface determinant of any immune effector cell such as CD3, CD16, CD32, or CD64, which are expressed on T lymphocytes, Natural Killer (NK) cells or other mononuclear cells. In many studies, diabody binding to effector cell determinants, e.g., Fcγ receptors (FcγR), was also found to activate the effector cell (Holliger et al. (1996) "Specific Killing Of Lymphoma Cells By Cytotoxic T-Cells Mediated By A Bispecific Diabody," Protein Eng. 9:299-305; Holliger et al. (1999) "Carcinoembryonic Antigen (CEA)-Specific T-cell Activation In Colon Carcinoma Induced By Anti-CD3 ×Anti-CEA Bispecific Diabodies And B7 ×Anti-CEA Bispecific Fusion Proteins," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "Bispecific Antibody Conjugates In Therapeutics," Adv. Drug. Deliv. Rev. 55:171-197).

However, the above advantages come at salient cost. The formation of such non-mono-specific diabodies requires the successful assembly of two or more distinct and different polypeptides (i.e., such formation requires that the diabodies be formed through the heterodimerization of different polypeptide chain species). This fact is in contrast to mono-specific diabodies, which are formed through the homodimerization of identical polypeptide chains. Because at least two dissimilar polypeptides (i.e., two polypeptide species) must be provided in order to form a non-mono-specific diabody, and because homodimerization of such polypeptides leads to inactive molecules (Takemura, S. et al. (2000) "Construction Of A Diabody (Small Recombinant Bispecific Antibody) Using A Refolding System," Protein Eng. 13(8):583-588), the production of such polypeptides must be accomplished in such a way as to prevent covalent bonding between polypeptides of the same species (Takemura, S. et al. (2000) "Construction Of A Diabody (Small Recombinant Bispecific Antibody) Using A Refolding System," Protein Eng. 13(8):583-588).

The art has therefore taught the non-covalent association of such polypeptides (see, e.g., Olafsen et al. (2004) "Covalent Disulfide-Linked Anti-CEA Diabody Allows Site-Specific Conjugation And Radiolabeling For Tumor Targeting Applications," Prot. Engr. Des. Sel. 17:21-27; Asano et al. (2004) "A Diabody For Cancer Immunotherapy And Its Functional Enhancement By Fusion Of Human Fc Domain," Abstract 3P-683, J. Biochem. 76(8):992; Takemura, S. et al. (2000) "Construction Of A Diabody (Small Recombinant Bispecific Antibody) Using A Refolding System," Protein Eng. 13(8):583-588; Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672). However, the art has recognized that bi-specific diabodies composed of non-covalently associated polypeptides are unstable and readily dissociate into non-functional monomers (see, e.g., Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672).

In the face of this challenge, the art has succeeded in developing stable, covalently bonded heterodimeric non-mono-specific diabodies, termed DART®s (see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; and Moore, P. A. et al. (2011) "Application Of Dual Affinity Retargeting Molecules To Achieve Optimal Redirected T-Cell Killing Of B-Cell Lymphoma," Blood 117(17):4542-4551; Veri, M. C. et al. (2010) "Therapeutic Control Of B Cell Activation Via Recruitment Of Fcgamma Receptor lib (CD32B) Inhibitory Function With A Novel Bispecific Antibody Scaffold," Arthritis Rheum. 62(7):1933-1943; Johnson, S. et al. (2010) "Effector Cell Recruitment With Novel Fv-Based Dual-Affinity Re-Targeting Protein Leads To Potent Tumor Cytolysis And in vivo B-Cell Depletion," J. Mol. Biol. 399(3):436-449). Such diabodies comprise two or more covalently complexed polypeptides and involve engineering one or more cysteine residues into each of the employed polypeptide species. For example, the addition of a cysteine residue to the c-terminus of such constructs has been shown to allow disulfide bonding between the polypeptide chains, stabilizing the resulting heterodimer without interfering with the binding characteristics of the bi-valent molecule.

Each of the two polypeptides of the simplest DART® comprises three Domains (FIG. 1). The first polypeptide comprises: (i) a Domain that comprises a binding region of a Light Chain Variable Domain of the a first immunoglobulin (VL1), (ii) a second Domain that comprises a binding region of a Heavy Chain Variable Domain of a second immunoglobulin (VH2), and (iii) a third Domain that serves to promote heterodimerization with the second polypeptide and to covalently bond the first polypeptide to the second polypeptide of the diabody. The second polypeptide contains a complementary first Domain (a VL2 Domain), a complementary second Domain (a VH1 Domain) and a third Domain that complexes with the third Domain of the first polypeptide chain in order to promote heterodimerization and covalent bonding with the first polypeptide chain. Such molecules are stable, potent and have the ability to simultaneously bind two or more antigens.

Figure 2:
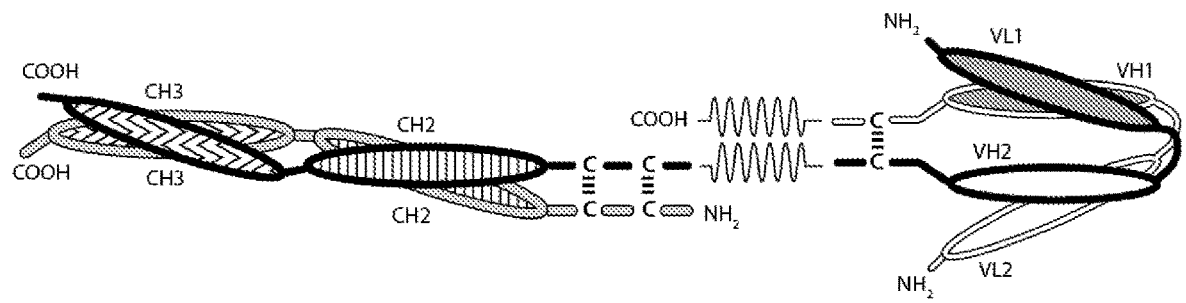
FIG. 2 shows a diagrammatic representation of the Domains of an Fc-bearing DART®.

In one embodiment, the third Domains of the first and second polypeptides each contain a cysteine residue, which serves to bind the polypeptides together via a disulfide bond. The third Domain of one or both of the polypeptides may additionally possesses the sequence of a CH2—CH3 Domain, such that complexing of the diabody polypeptides forms an Fc Domain that is capable of binding to the Fc receptor of cells (such as B lymphocytes, dendritic cells, Natural Killer cells, macrophages, neutrophils, eosinophils, basophils and mast cells) (FIG. 2). Many variations of such molecules have been described (see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538). These Fc-bearing DART®s may comprise three polypeptide chains. The first polypeptide of such a diabody contains three Domains: (i) a VL1-containing Domain, (ii) a VH2-containing Domain and (iii) a Domain containing a CH2—CH3 sequence. The second polypeptide of such DART® contains: (i) a VL2-containing Domain, (ii) a VH1-containing Domain and (iii) a Domain that promotes heterodimerization and covalent bonding with the diabody's first polypeptide chain. The third polypeptide of such DART® comprises a CH2—CH3 sequence. Thus, the first and second polypeptide chains of such DART® complex together to form a VL1/VH1 binding site that is capable of binding to the epitope, as well as a VL2/VH2 binding site that is capable of binding to the second epitope. The first and second polypeptides are bonded to one another through a disulfide bond involving cysteine residues in their respective third Domains. Notably, the first and third polypeptide chains complex with one another to form an Fc Domain that is stabilized via a disulfide bond. Such diabodies have enhanced potency. Such Fc-bearing DART®s may have either of two orientations (Table 1):

TABLE 1

| | | |
|---|---|---|
| First Orientation | 3rd Chain | NH2—CH2—CH3—COOH |
| | 1st Chain | NH2-VL1-VH2-Heterodimer-Promoting Domain-CH2—CH3—COOH |
| | 2nd Chain | NH2-VL2-VH1-Heterodimer-Promoting Domain-COOH |
| Second Orientation | 3rd Chain | NH2—CH2—CH3—COOH |
| | 1st Chain | NH2—CH2—CH3-VL1-VH2-Heterodimer-Promoting Domain-COOH |
| | 2nd Chain | NH2-VL2-VH1-Heterodimer-Promoting Domain-COOH |

Figure 3:
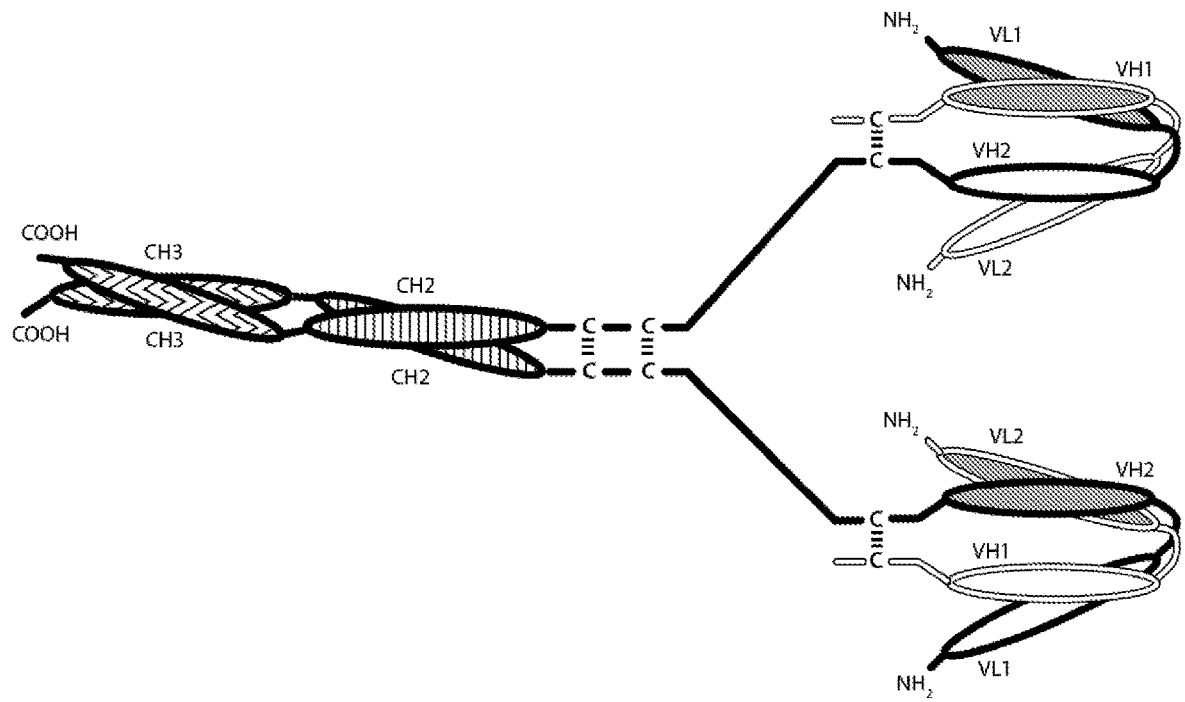
FIG. 3 shows a diagrammatic representation of the Domains of an Fc-DART®.

An even more complex DART® , termed an Fc-DART® (FIG. 3) has also been described (WO 2012/018687). Fc-DART®s have four polypeptide chains. The first and third polypeptide chains of such a diabody contain three Domains: (i) a VL1-containing Domain, (ii) a VH2-containing Domain and (iii) a Domain containing a CH2—CH3 sequence. The second and fourth polypeptide of the Fc-DART® contain: (i) a VL2-containing Domain, (ii) a VH1-containing Domain and (iii) a Domain that promotes heterodimerization and covalent bonding with the Fc-DART's™ first polypeptide chain. The VL and/or VH Domains of the third and fourth polypeptide chains, and VL and/or VH Domains of the first and second polypeptide chains may be the same or different so as to permit tetravalent binding that is either mono-specific, bi-specific or tetra-specific (Table 2).

TABLE 2

| | | |
|---|---|---|
| Bi-Specific | 2nd Chain | NH2-VL2-VH1-COOH |
| | 1st Chain | NH2-VL1-VH2-[CH2—CH3]—COOH |
| | 3rd Chain | NH2-VL1-VH2-[CH2—CH3]—COOH |
| | 4th Chain | NH2-VL2-VH1-COOH |
| Tetra-Specific | 2nd Chain | NH2-VL2-VH1-COOH |
| | 1st Chain | NH2-VL1-VH2-[CH2—CH3]—COOH |
| | 3rd Chain | NH2-VL3-VH4-[CH2—CH3]—COOH |
| | 4th Chain | NH2-VL4-VH3-COOH |

Throughout this application, the numbering of amino acid residues of the light and heavy chains of antibodies is according to the EU index as in Kabat et al. (1992) SEQUENCES OF PROTEINS OF IMMUNOLOGICAL INTEREST, National Institutes of Health Publication No. 91-3242.

The terms "polypeptide" and "peptide" are used interchangeably herein to refer to polymers of amino acids of any length, but especially lengths greater than 3, 5, 10, 15, 20 or 25 amino acid residues. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The polypeptides of this invention can occur as single chains or as complexed chains.

The terms "diabody" and "DART™" have been discussed above. A DART® is a type of diabody that comprises at least two polypeptide chains that preferably complex with one another through a covalent interaction to form at least two epitope-binding sites, which may recognize the same or different epitopes. Two of the polypeptide chains of a diabody or DART™ each comprise immunoglobulin Light Chain Variable Region and an immunoglobulin Heavy Chain Variable Region, but these regions do not interact to form an Epitope-Binding Site (i.e., they are not mutually "complementary"). Rather, the immunoglobulin Heavy Chain Variable Region of one (e.g., the first) of the diabody or DART™ polypeptide chains interacts with the immunoglobulin Light Chain Variable Region of a different (e.g., the second) diabody or DART™ polypeptide chain to form an Epitope-Binding Site. Similarly, the immunoglobulin Light Chain Variable Region of one (e.g., the first) of the diabody or DART™ polypeptide chains interacts with the immunoglobulin Heavy Chain Variable Region of a different (e.g., the second) diabody or DART™ polypeptide chain to form an Epitope-Binding Site. DART™ molecules are disclosed in United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; WO 2006/113665, WO 2008/157379 and Moore, P.A. et al. (2011) "Application Of Dual Affinity Retargeting Molecules To Achieve Optimal Redirected T-Cell Killing Of B-Cell Lymphoma," Blood 117(17):4542-4551; Veri, M.C. et al. (2010) "Therapeutic Control Of B Cell Activation Via Recruitment Of Fcgamma Receptor Iib (CD32B) Inhibitory Function With A Novel Bispecific Antibody Scaffold," Arthritis Rheum. 62(7):1933-1943; and Johnson, S. et al. (2010) "Effector Cell Recruitment With Novel Fv-Based Dual-Affinity Re-Targeting Protein Leads To Potent Tumor Cytolysis And in vivo B-Cell Depletion," J. Mol. Biol. 399(3):436-449.

As used herein, the terms "association" or "associating," with regard to polypeptides (e.g., one diabody polypeptide to another, an immunoglobulin light chain to an immunoglobulin heavy chain, one CH2—CH3 Domain to another CH2—CH3 Domain, etc.) is intended to denote a non-covalent combining of the polypeptides. The terms "complexes" or "complexing" are intended to denote a covalent combining of the polypeptides.

As used herein, the diabodies of the present invention are said to mediate "coordinated binding" if their Epitope-Binding Domains are capable of concurrently being bound to their respective recognized epitopes. Such binding may be simultaneous.

The Epitope-Binding Domains of the diabodies of the present invention bind to their recognized epitopes in an "immunospecific" manner. As used herein, an antibody, diabody or other epitope-binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind to a second target. As such, "specific binding" does not necessarily require (although it can include) exclusive binding. Generally, but not necessarily, reference to binding means "specific" binding.

The various immunoglobulin Domains of such molecules may be derived from immunoglobulins of any isotype or allotype including, but not limited to, IgA, IgD, IgG, IgE and IgM. In preferred embodiments, as discussed below such immunoglobulins are derived from IgG immunoglobulins.

In specific embodiments, the IgG isotype used is IgG1, however IgG of other isotypes (e.g., IgG2, IgG3 or IgG4 or an allotype thereof) may be employed.

II. Preferred PD-1×LAG-3 Bi-Specific Diabodies Of the Present Invention

The present invention relates to PD-1×LAG-3 bi-specific diabodies. The preferred PD-1×LAG-3 bi-specific diabodies of the present invention possess epitope-binding fragments of antibodies that enable them to be able to coordinately bind to two different epitopes: an epitope of PD-1 and an epitope of LAG-3, so as to attenuate the inhibitory activities of such molecules. As used herein, such attenuation refers to a decrease of at least 20%, a decrease of at least 50%, a decrease of at least 80%, or a decrease of at least 90% in detectable PD-1 and or LAG-3 inhibitory activity, or the complete elimination of detectable PD-1 and or LAG-3 inhibitory activity.

A. Anti-PD-1 Binding Capabilities

Antibodies that are immunospecific for PD-1 are known (see, e.g., U.S. Pat. Nos. 8,008,449; 8,552,154; PCT Patent Publications WO 2012/135408; WO 2012/145549; and WO 2013/014668). Additional desired antibodies may be made by isolating antibody-secreting hybridomas elicited using PD-1 or a peptide fragment thereof. Human PD-1 (including a 20 amino acid residue signal sequence (shown underlined) and the 268 amino acid residue mature protein) has the amino acid sequence (SEQ ID NO:1):

```
MQIPQAPWPV VWAVLQLGWR PGWFLDSPDR PWNPPTFSPA

LLVVTEGDNA TFTCSFSNTS ESFVLNWYRM SPSNQTDKLA

AFPEDRSQPG QDCRFRVTQL PNGRDFHMSV VRARRNDSGT

YLCGAISLAP KAQIKESLRA ELRVTERRAE VPTAHPSPSP

RPAGQFQTLV VGVVGGLLGS LVLLVWVLAV ICSRAARGTI

GARRTGQPLK EDPSAVPVFS VDYGELDFQW REKTPEPPVP

CVPEQTEYAT IVFPSGMGTS SPARRGSADG PRSAQPLRPE

DGHCSWPL
```

Preferred anti-PD-1 antibodies include: PD-1 mAb 1 (5C4; BMS-936558)), PD-1 mAb 2 (MK-3475; Merck, lambrolizumab), PD-1 mAb 3 (EH12.2H7; Dana Farber) and PD-1 mAb 4 (CT-011; CureTech, BAT-1).

The amino acid sequence of the Heavy Chain Variable Domain of PD-1 mAb 1 has the amino acid sequence (SEQ ID NO:2) (CDRs are shown underlined):

```
QVQLVESGGG VVQPGRSLRL DCKASGITFS NSGMHWVRQA

PGKGLEWVAV IWYDGSKRYY ADSVKGRFTI SRDNSKNTLF

LQMNSLRAED TAVYYCATND DYWGQGTLVT VSS
```

The amino acid sequence of the Light Chain Variable Domain of PD-1 mAb 1 has the amino acid sequence (SEQ ID NO:3) (CDRs are shown underlined):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIK
```

The amino acid sequence of the Heavy Chain Variable Domain of PD-1 mAb 2 has the amino acid sequence (SEQ ID NO:4) (CDRs are shown underlined):

```
QVQLVQSGVE VKKPGASVKV SCKASGYTFT NYYMYWVRQA

PGQGLEWMGG INPSNGGTNF NEKFKNRVTL TTDSSTTTAY

MELKSLQFDD TAVYYCARRD YRFDMGFDYW GQGTTVTVSS
```

The amino acid sequence of the Light Chain Variable Domain of PD-1 mAb 2 has the amino acid sequence (SEQ ID NO:5) (CDRs are shown underlined):

```
EIVLTQSPAT LSLSPGERAT LSCRASKGVS TSGYSYLHWY

QQKPGQAPRL LIYLASYLES GVPARFSGSG SGTDFTLTIS

SLEPEDFAVY YCQHSRDLPL TFGGGTKVEIK
```

The amino acid sequence of the Heavy Chain Variable Domain of PD-1 mAb 3 has the amino acid sequence (SEQ ID NO:6) (CDRs are shown underlined):

```
QVQLQQSGAE LAKPGASVQM SCKASGYSFT SSWIHWVKQR

PGQGLEWIGY IYPSTGFTEY NQKFKDKATL TADKSSSTAY

MQLSSLTSED SAVYYCARWR DSSGYHAMDY WGQGTSVTVSS
```

The amino acid sequence of the Light Chain Variable Domain of PD-1 mAb 3 has the amino acid sequence (SEQ ID NO:7) (CDRs are shown underlined):

```
DIVLTQSPAS LTVSLGQRAT ISCRASQSVS TSGYSYMHWY

QQKPGQPPKL LIKFGSNLES GIPARFSGSG SGTDFTLNIH

PVEEEDTATY YCQHSWEIPY TFGGGTKLEI K
```

The amino acid sequence of the Heavy Chain Variable Domain of PD-1 mAb 4 has the amino acid sequence (SEQ ID NO:8) (CDRs are shown underlined):

```
QVQLVQSGSE LKKPGASVKI SCKASGYTFT NYGMNWVRQA

PGQGLQWMGW INTDSGESTY AEEFKGRFVF SLDTSVNTAY

LQITSLTAED TGMYFCVRVG YDALDYWGQG TLVTVSS
```

The amino acid sequence of the Light Chain Variable Domain of PD-1 mAb 4 has the amino acid sequence (SEQ ID NO:9) (CDRs are shown underlined):

```
EIVLTQSPSS LSASVGDRVT ITCSARSSVS YMHWFQQKPG

KAPKLWIYRT SNLASGVPSR FSGSGSGTSY CLTINSLQPE

DFATYYCQQR SSFPLTFGGG TKLEIK
```

B. Anti-LAG-3 Binding Capabilities

Antibodies that are immunospecific for LAG-3 are also known (see, e.g., WO 2014/008218). Additional desired antibodies may be made by isolating antibody-secreting hybridomas elicited using LAG-3 or a peptide fragment thereof. Human LAG-3 (including a 28 amino acid residue signal sequence (shown underlined) and the 497 amino acid residue mature protein) has the amino acid sequence (SEQ ID NO:10):

```
MWEAQFLGLL FLQPLWVAPV KPLQPGAEVP VVWAQEGAPA

QLPCSPTIPL QDLSLLRRAG VTWQHQPDSG PPAAAPGHPL

APGPHPAAPS SWGPRPRRYT VLSVGPGGLR SGRLPLQPRV

QLDERGRQRG DFSLWLRPAR RADAGEYRAA VHLRDRALSC

RLRLRLGQAS MTASPPGSLR ASDWVILNCS FSRPDRPASV

HWFRNRGQGR VPVRESPHHH LAESFLFLPQ VSPMDSGPWG

CILTYRDGFN VSIMYNLTVL GLEPPTPLTV YAGAGSRVGL

PCRLPAGVGT RSFLTAKWTP PGGGPDLLVT GDNGDFTLRL

EDVSQAQAGT YTCHIHLQEQ QLNATVTLAI ITVTPKSFGS

PGSLGKLLCE VTPVSGQERF VWSSLDTPSQ RSFSGPWLEA

QEAQLLSQPW QCQLYQGERL LGAAVYFTEL SSPGAQRSGR

APGALPAGHL LLFLILGVLS LLLLVTGAFG FHLWRRQWRP

RRFSALEQGI HPPQAQSKIE ELEQEPEPEP EPEPEPEPEP

EPEQL
```

A preferred anti-LAG-3 antibody is LAG-3 mAb 1 (25F7; BMS-986016, Medarex/BMS). The amino acid sequence of the Heavy Chain Variable Domain of LAG-3 mAb 1 has the amino acid sequence (SEQ ID NO:11) (CDRs are shown underlined):

```
QVQLQQWGAG LLKPSETLSL TCAVYGGSFS DYYWNWIRQP

PGKGLEWIGE INHNGNTNSN PSLKSRVTLS LDTSKNQFSL

KLRSVTAADT AVYYCAFGYS DYEYNWFDPW GQGTLVTVSS
```

The amino acid sequence of the Light Chain Variable Domain of LAG-3 mAb 1 has the amino acid sequence (SEQ ID NO:12) (CDRs are shown underlined):

```
EIVLTQSPAT LSLSPGERAT LSCRASQSIS SYLAWYQQKP

GQAPRLLIYD ASNRATGIPA RFSGSGSGTD FTLTISSLEP

EDFAVYYCQQ RSNWPLTFGQ GTNLEIK
```

As used herein, the term "epitope-binding fragment of an antibody" means a fragment of an antibody capable of immunospecifically binding to an epitope. An epitope-binding fragment may contain 1, 2, 3, 4, 5 or all 6 of the CDR Domains of such antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino terminus and a carboxyl terminus (e.g., a diabody, an Fab fragment, an Fab2 fragment, etc.).

C. Preferred DART® Diabodies Of The Present Invention

1. General Considerations

The preferred diabodies of the present invention are bi-specific, tetra-valent, Fc-DART® diabodies (FIG. 3) that are composed of four total polypeptide chains. The four polypeptide chains comprise two CH2—CH3-containing polypeptides (i.e., the "first" and "third" polypeptide chains of the diabody) that complex together to form an Fc Domain and two identical non-CH3-containing polypeptides (i.e., the "second" and "fourth" polypeptide chains of the diabody), each of which complex with a CH2—CH3-containing polypeptide of the diabody to form an Epitope-Binding Domain that is immunospecific for PD-1 or LAG-3. Thus, for example, the first polypeptide chain will contain an anti-PD-1 (or anti-LAG-3) Variable Light Chain (VL) Domain and an anti-LAG-3 (or anti-PD-1) Variable Heavy Chain (VH) Domain, and will complex with a second polypeptide chain that possesses a complementary anti-PD-1 (or anti-LAG-3) VH Domain and a complementary anti-LAG-3 (or anti-PD-1) VL Domain, so as to form a first pair of PD-1 and LAG-3 Epitope-Binding Domains. Likewise, the third polypeptide chain will contain an anti-PD-1 (or an anti-LAG-3) Variable Light Chain (VL) Domain and an anti-LAG-3 (or an anti-PD-1) Variable Heavy Chain (VH) Domain, and will complex with a fourth polypeptide chain that possesses a complementary anti-PD-1 (or anti-LAG-3) VH Domain and a complementary anti-LAG-3 (or anti-PD-1) VL Domain, so as to form a second pair of PD-1 and LAG-3 Epitope-Binding Domains.

Since the Variable Light Chain and Variable Heavy Chain Domains of the same polypeptide are directed toward different epitopes, they cannot complex together to form an Epitope-Binding Domain that is able to bind either PD-1 or LAG-3. The Variable Light Chain and Variable Heavy Chain Domains of the first polypeptide are preferably spaced apart from one another by an intervening linker peptide that is sufficiently short as to substantially prevent the complexing of these Domains. An exemplary linker, has the sequence (SEQ ID NO:13: GGGSGGGG. Other linkers of similar length (so as to prevent the VL and VH Domains of the same polypeptide chain from interacting with each other) may alternatively be employed.

Figure 4:
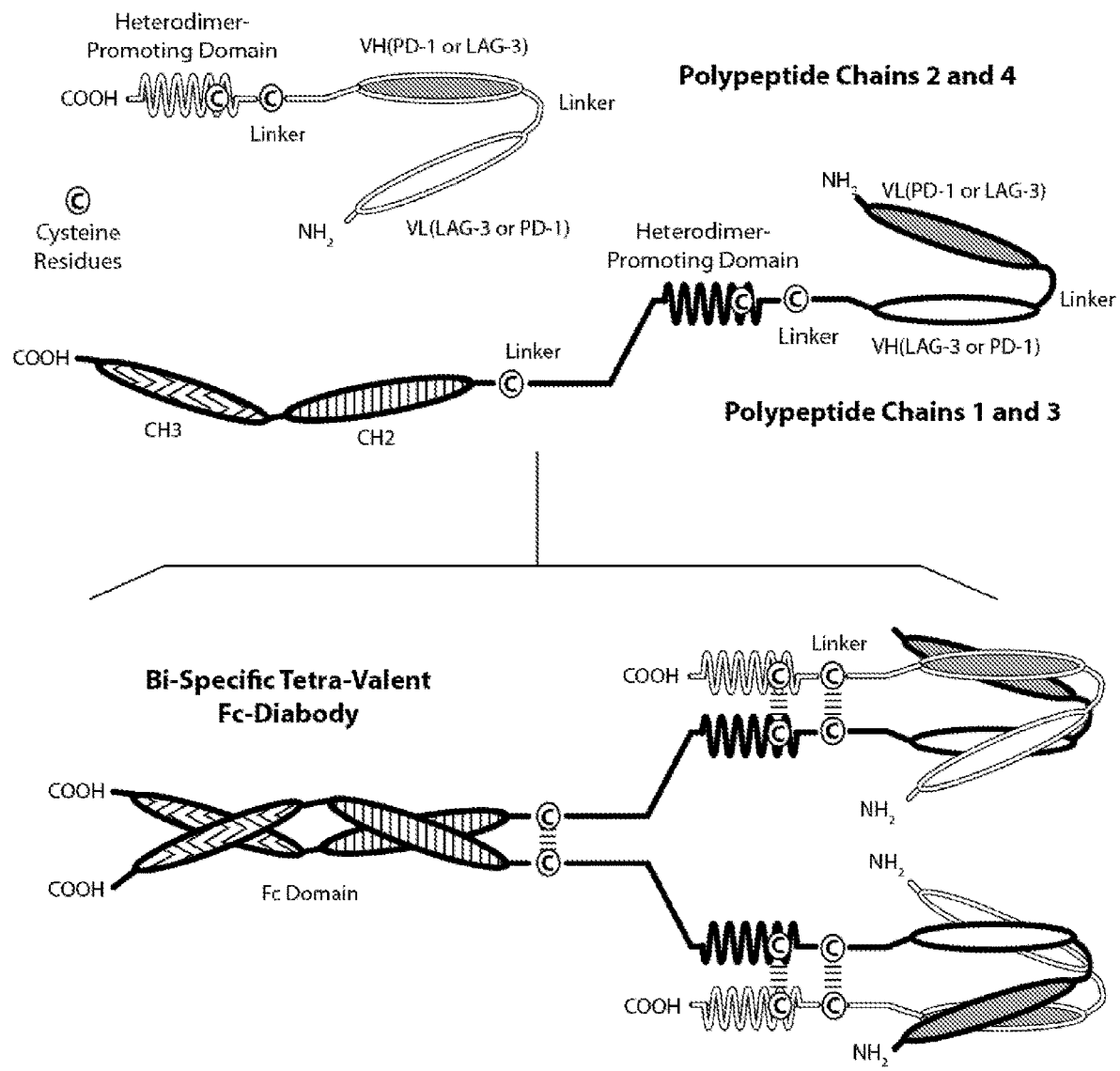
FIG. 4 shows a diagrammatic representation of the Domains of a preferred PD-1×LAG-3 bi-specific, tetra-valent, diabody of the present invention. Four polypeptide chains, two of which have the Domains of polypeptide chains 1 and 3, and two of which have the Domains of polypeptide chains 2 and 4, complex together to form the diabody. Disulfide bonds (shown as striped lines) covalently link polypeptide chains 1 and 2, polypeptide chains 1 and 3 and polypeptide chains 3 and 4. The Variable Light Chain Domains and Variable Heavy Chain Domains of the same polypeptide chain are directed to different epitopes (either PD-1 or LAG-3), such that the resulting diabody has two Epitope-Binding Domains that are immunospecific for PD-1 and two Epitope-Binding Domains that are immunospecific for LAG-3.

As shown in FIG. 4, the most preferred bi-specific, tetra-valent, Fc-DART® diabodies of the present invention are Fc-DART® diabodies that have been modified to contain Heterodimer-Promoting Domains. The inclusion of such Domains fosters heterodimer formation between the polypeptide chains of the diabody. The inclusion of such Domains is not essential, and the present invention includes PD-1×LAG-3 bi-specific diabodies that do not possess such Domains. Preferred Heterodimer-Promoting Domains include "E-coil" Domains (SEQ ID NO:14): EVAALEK EVAALEKEVAALEKEVAALEK, and "K-coil" Domains (SEQ ID NO:15): KVAALKEKVAALKEKVAALKE KVAALKE. More specifically, a pair of polypeptide chains that are desired to complex together are each engineered to contain one (or more) such Heterodimer-Promoting Domains, with the employed Domain(s) of one polypeptide chain being complementary to the employed Domain(s) of the other polypeptide chain (e.g., one polypeptide chain will contain an E-coil Domain and the other will contain a K-coil Domain). Where the two polypeptide chains are engineered to contain more than one such Heterodimer-Promoting Domains, they can be of the same charge, or more preferably of opposite charge.

Particularly preferred are Heterodimer-Promoting Domains that comprise modifications of the above-described E-coil and K-coil sequences so as to include one or more cysteine residues. The presence of such cysteine residues permits the coil present on one polypeptide chain to become covalently bonded to a complementary coil present on another polypeptide chain, thereby covalently bonding the polypeptide chains to one another and increasing the stability of the diabody. Examples of such particularly preferred are Heterodimer-Promoting Domains include a Modified E-Coil having the amino acid sequence (SEQ ID NO:16): EVAA$\underline{C}$EKEVAALEKEVAALEKEVAALEK, wherein a leucine residue of SEQ ID NO:14 has been replaced with a cysteine residue (shown underlined), and a Modified K-Coil having the amino acid sequence (SEQ ID NO:17): KVAA$\underline{C}$KEKVAALKEKVAALKEKVAALKE, wherein a leucine residue of SEQ ID NO:15 has been replaced with a cysteine residue (shown underlined).

The Variable Heavy Chain Domain of the first polypeptide and the Heterodimer-Promoting Domain of that polypeptide are preferably spaced apart from one another by an intervening linker peptide that contains 1, 2, 3 or more cysteine residues. A preferred cysteine-containing spacer peptide has the sequence is SEQ ID NO:18: GGCGGG. Other linkers of similar length (so as to include a cysteine residue that can covalently bond with a cysteine residue of another polypeptide chain) may be employed.

Preferably, the employed Heterodimer-Promoting Domain and the CH2—CH3 Domain of the first polypeptide chain are spaced apart from one another by an intervening cysteine-containing linker peptide that provides improved stabilization to the Heterodimer-Promoting Domain. A suitable cysteine-containing linker peptide has the amino acid sequence (SEQ ID NO:19): DKTHTCPPCP, however, a more preferred linker has the amino acid sequence (SEQ ID NO:20): LEPKSADKTHTCPPC. Other linkers of similar length (so as to include a cysteine residue that can covalently bond with a cysteine residue of another polypeptide chain) may alternatively be employed.

The amino acid sequence of a wild-type CH2—CH3 Domain is as follows (positioning is as in the EU index as in Kabat et al. (1992) SEQUENCES OF PROTEINS OF IMMUNOLOGICAL INTEREST, National Institutes of Health Publication No. 91-3242) (SEQ ID NO:21):

hole' (e.g., a substitution with glycine). Such sets of mutations can be engineered into any pair of polypeptides comprising the diabody molecule, and further, engineered into any portion of the polypeptides chains of said pair. Methods of protein engineering to favor heterodimerization over homodimerization are well-known in the art, in particular with respect to the engineering of immunoglobulin-like molecules, and are encompassed herein (see e.g., U.S. Pat. No. 7,695,936 and Patent Publication 2007/ 0196363, Ridgway et al. (1996) "'Knobs-Into-Holes' Engineering Of Antibody CH3 Domains For Heavy Chain Heterodimerization," Protein Engr. 9:617-621, Atwell et al. (1997) "Stable Heterodimers From Remodeling The Domain Interface Of A Homodimer Using A Phage Display Library," J. Mol. Biol. 270: 26-35, and Xie et al. (2005) "A New Format Of Bispecific Antibody: Highly Efficient Heterodimerization, Expression And Tumor Cell Lysis," J. Immunol. Methods 296:95-101; each of which is hereby incorporated herein by reference in its entirety. A preferred knob is created by modifying a native IgG Fc Domain to contain the modification T366W. A preferred hole is created by modifying a native IgG Fc Domain to contain the modification T366S, L368A and Y407V. To aid in purifying the diabodies of the present invention, the polypeptide chain containing the hole mutations additionally comprises a substitution at position 435 (H435R) to remove the Protein A binding site. Thus, homodimers of polypeptides containing the hole mutations will not bind to protein A, whereas the diabodies that form as a result of knob and hole containing heterodimers will retain its ability to bind protein A via the protein A binding site on the polypeptide chain containing the knob mutation.

The invention also encompasses molecules comprising variant Fc Domains comprising one or more amino acid substitutions, insertions, or deletions relative to a comparable wild-type Fc Domain. Molecules comprising variant

```
|CH2 →
PAPELLGGPS  VFLFPPKPKD  TLMISRTPEV  TCVVVDVSHE  DPEVKFNWYV  DGVEVHNAKT
230         240         250         260         270         280

←CH2|CH3→
KPREEQYNST  YRVVSVLTVL  HQDWLNGKEY  KCKVSNKALP  APIEKTISKA  K GQPREPQVY
290         300         310         320         330          340

TLPPSREEMT  KNQVSLTCLV  KGFYPSDIAV  EWESNGQPEN  NYKTTPPVLD  SDGSFFLYSK
350         360         370         380         390         400

←CH3|
LTVDKSRWQQ  GNVFSCSVMH  EALHNHYTQK  SLSLSPGK
410         420         430         440
```

For tri-specific or tetra-specific diabodies (i.e., for diabodies whose first and third polypeptide chains are not identical), it is desirable to reduce or prevent homodimerization from occurring between the CH2—CH3 Domains of two first polypeptide chains or between the CH2—CH3 Domains of two third polypeptide chains. In order to promote heterodimerization between the first and third polypeptide chains, the CH2—CH3 Domain of these chains are preferably modified so as to promote such heterodimerization. For example, an amino acid substitution (preferably a substitution with an amino acid comprising a bulky side group forming a 'knob', e.g., tryptophan) can be introduced into the CH2 or CH3 Domain of the first polypeptide chain such that steric interference will prevent interaction with a similarly mutated Domain and will obligate the mutated Domain to pair with a Domain into which a complementary, or accommodating mutation has been engineered, i.e., 'the Fc Domains normally have altered phenotypes relative to molecules comprising wild-type Fc Domains The variant phenotype may be expressed as altered serum half-life, altered stability, altered susceptibility to cellular enzymes or altered effector function as assayed in an NK dependent or macrophage dependent assay. Fc Domain modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) "Fc Optimization Of Therapeutic Antibodies Enhances Their Ability To Kill Tumor Cells In Vitro And Controls Tumor Expansion In Vivo Via Low-Affinity Activating Fcgamma Receptors," Cancer Res. 57(18):8882-8890). Exemplary variants of human IgG1 Fc Domains with reduced binding to CD32B and/or increased binding to CD16A contain F243L, R929P, Y300L, V305I or P296L substitutions. These amino acid substitutions may be present in a human IgG1 Fc Domain in any combination. In one embodiment, the human IgG1 Fc Domain variant contains a F243L, R929P and Y300L substitution. In another embodiment, the human IgG1 Fc Domain variant contains a F243L, R929P, Y300L, V3051 and P296L substitution. In another embodiment, the human IgG1 Fc Domain variant contains an N297Q substitution, L234A and L235A substitutions or a D265A substitution, as these mutations abolish FcR binding. The CH2—CH3 Domain of the first polypeptide chain of such molecules will have the "knob-bearing" sequence (SEQ ID NO:22):

```
PAPEAAGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSREEMT KNQVSLWCLV KGFYPSDIAV EWESNGQPEN

NYKTTPPVLD SDGSFFLYSK LTVDKSRWQQ GNVFSCSVMH

EALHNHYTQK SLSLSPGK
``` or the "hole-bearing" sequence with an H435R substitution to abrogate Protein A binding (SEQ ID NO:23):

```
PAPEAAGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSREEMT KNQVSLSCAV KGFYPSDIAV EWESNGQPEN

NYKTTPPVLD SDGSFFLVSK LTVDKSRWQQ GNVFSCSVMH

EALHNRYTQK SLSLSPGK
```

As will be recognized, a "hole-bearing" CH2—CH3 Domain (e.g., SEQ ID NO:22) could be employed in the first polypeptide chain, in which case, a "knob-bearing" CH2—CH3 Domain (e.g., SEQ ID NO:22) would be employed in the third polypeptide chain.

For bi-specific, tetra-valent, diabodies of the present invention whose first and third polypeptide chains are not different, a preferred CH2—CH3 Domain is a Modified CH2—CH3 Domain having the amino acid sequence (SEQ ID NO:24):

```
PAPEAAGGPS VFLFPPKPKD TLYITREPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSREEMT KNQVSLTCLV KGFYPSDIAV EWESNGQPEN

NYKTTPPVLD SDGSFFLYSK LTVDKSRWQQ GNVFSCSVMH

EALHNHYTQK SLSLSPG
```

Thus, in sum, the preferred first and third polypeptide chains of a preferred PD-1×LAG-3 bi-specific, tetra-valent, diabody Fc-DART® diabody of the present invention have identical sequences, and the second and fourth polypeptide chains of such preferred PD-1×LAG-3 bi-specific, tetra-valent, Fe-DART® diabodies have identical sequences, as shown in Table 3:

TABLE 3

| Variation | Domains of the First and Third Polypeptide Chains | Domains of the Second and Fourth Polypeptide Chains |
| --- | --- | --- |
| I | (VL of anti-PD-1 Epitope-Binding Domain)-(Linker)-(VH of anti-LAG-3 Epitope-Binding Domain)-(Linker)-(Modified E-Coil Heterodimer-Promoting Domain)-(Linker)-(Modified CH2—CH3 Domain) | (VL of anti-LAG-3 Epitope Binding Domain)-(Linker)-(VH of an anti-PD-1 Epitope Binding Domain)-(Linker)-(Modified K-Coil Heterodimer-Promoting Domain) |
| II | (VL of anti-PD-1 Epitope Binding Domain)-(Linker)-(VH of anti-LAG-3 Epitope Binding Domain)-(Linker)-(Modified K-Coil Heterodimer-Promoting Domain)-(Linker)-(Modified CH2—CH3 Domain) | (VL of anti-LAG-3 Epitope Binding Domain)-(Linker)-(VH of an anti-PD-1 Epitope Binding Domain)-(Linker)-(Modified E-Coil Heterodimer-Promoting Domain) |
| III | (VL of anti-LAG-3 Epitope Binding Domain)-(Linker)-(VH of anti-PD-1 Epitope Binding Domain)-(Linker)-(Modified E-Coil Heterodimer-Promoting Domain)-(Linker)-(Modified CH2—CH3 Domain) | (VL of anti-PD-1 Epitope Binding Domain)-(Linker)-(VH of an anti-LAG-3 Epitope Binding Domain)-(Linker)-(Modified K-Coil Heterodimer-Promoting Domain) |
| IV | (VL of anti-LAG-3 Epitope Binding Domain)-(Linker)-(VH of anti-PD-1 Epitope Binding Domain)-(Linker)-(Modified K-Coil Heterodimer-Promoting Domain)-(Linker)-(Modified CH2—CH3 Domain) | (VL of anti-PD-1 Epitope Binding Domain)-(Linker)-(VH of an anti-LAG-3 Epitope Binding Domain)-(Linker)-(Modified E-Coil Heterodimer-Promoting Domain) |

2. First Exemplary PD-1×LAG-3 Bi-Specific Fc-DART® Diabody
(PD-1×LAG-3 Fc-DART®-1)

A first particularly preferred PD-1×LAG-3 bi-specific, tetra-valent, Fc-DART® diabody of the present invention ("PD-1×LAG-3 Fc-DART®-1") has first and third polypeptide chains of identical sequence. Such first/third polypeptide chain has the amino acid sequence (SEQ ID NO:25):

```
EIVLTQSPAT LSLSPGERAT LSCRASQSIS SYLAWYQQKP
GQAPRLLIYD ASNRATGIPA RFSGSGSGTD FTLTISSLEP
EDFAVYYCQQ RSNWPLTFGQ GTNLEIKGGG SGGGGQVQLV
ESGGGVVQPG RSLRLDCKAS GITFSNSGMH WVRQAPGKGL
EWVAVIWYDG SKRYYADSVK GRFTISRDNS KNTLFLQMNS
LRAEDTAVYY CATNDDYWGQ GTLVTVSSGG CGGGEVAACE
KEVAALEKEV AALEKEVAAL EKLEPKSADK THTCPPCPAP
EAAGGPSVFL FPPKPKDTLY ITREPEVTCV VVDVSHEDPE
VKFNWYVDGV EVHNAKTKPR EEQYNSTYRV VSVLTVLHQD
WLNGKEYKCK VSNKALPAPI EKTISKAKGQ PREPQVYTLP
PSREEMTKNQ VSLTCLVKGF YPSDIAVEWE SNGQPENNYK
TTPPVLDSDG SFFLYSKLTV DKSRWQQGNV FSCSVMHEAL
HNHYTQKSLS LSPG
``` wherein, amino acid residues 1-107 are the amino acid residues of the Light Chain Variable Domain of LAG-3 mAb 1 (SEQ ID NO:12), amino acid residues 108-115 are the amino acid residues of the linker GGGSGGGG (SEQ ID NO:13), amino acid residues 116-228 are the amino acid residues of the Heavy Chain Variable Domain of PD-1 mAb 1 (SEQ ID NO:2), amino acid residues 229-234 are the amino acid residues of the cysteine-containing spacer peptide GGCGGG (SEQ ID NO:18), amino acid residues 235-262 are the amino acid residues of the Modified E-Coil (SEQ ID NO:16), amino acid residues 263-277 are the amino acid residues of the cysteine-containing linker peptide LEPKSADKTHTCPPC (SEQ ID NO:20) and amino acid residues 278-494 are the amino acid residues of the Modified CH2—CH3 Domain (SEQ ID NO:24).

A nucleic acid molecule that encodes such a first/third polypeptide chain is (SEQ ID NO:26):

```
gaaattgtcc tgacacagtc tcccgcaacc ctgagtttga
gtcctgggga gcgagcaact ctctcctgcc gagcctccca
gagtatctcc tcctacctcg cctggtacca acagaagcca
gggcaggctc caaggctgct tatctatgac gcctctaacc
gcgcaactgg gattcccgca cgcttctccg gctctggttc
cggcacagac tttacactta ctatctctag cctggagcca
gaagactttg ccgtgtacta ttgtcagcaa cgttccaatt
ggccccttac ctttgggcag ggcactaact tggaaatcaa
aggtgccgga tccggcggcg gaggccaggt tcagctggtc
gagagtggtg gcggcgttgt gcaacctggg cgttccctcc
gattggactg taaagcttcc ggcattactt tctcaaattc
cggcatgcat tgggtgaggc aagcccctgg aaaagggctc
gaatgggtgg ctgtgatttg gtacgatggc agcaaacggt
actacgccga ttctgttaag ggccgcttta ccatctcccg
cgataactca aagaacacac tgtttctgca aatgaatagt
cttagagccg aggacaccgc cgtgtactac tgtgccacaa
atgacgatta ttgggggcag ggcacattgg tcacagtgtc
ttccggagga tgtggcggtg gagaagtggc cgcatgtgag
aaagaggttg ctgctttgga gaaggaggtc gctgcacttg
aaaaggaggt cgcagccctg gagaaactgg agcccaaatc
tgctgacaaa actcacacat gcccaccgtg cccagcacct
gaagccgcgg ggggaccgtc agtcttcctc ttccccccaa
aacccaagga caccctctat catcacccgg agcctgaggt
cacatgcgtg gtggtggacg tgagccacga agaccctgag
gtcaagttca actggtacgt ggacggcgtg gaggtgcata
atgccaagac aaagccgcgg gaggagcagt acaacagcac
gtaccgtgtg gtcagcgtcc tcaccgtcct gcaccaggac
tggctgaatg gcaaggagta caagtgcaag gtctccaaca
aagccctccc agcccccatc gagaaaacca tctccaaagc
caaagggcag ccccgagaac acaggtgta cacctgccc
ccatcccggg aggagatgac caagaaccag gtcagcctga
cctgcctggt caaaggcttc tatcccagcg acatcgccgt
ggagtgggag agcaatgggc agccggagaa caactacaag
accacgcctc ccgtgctgga ctccgacggc tccttcttcc
tctacagcaa gctcaccgtg gacaagagca ggtggcagca
ggggaacgtc ttctcatgct ccgtgatgca tgaggctctg
cacaaccact acacgcagaa gagcctctcc ctgtctccgg
gt
```

The second and fourth polypeptide chain of such PD-1×LAG-3 Fc-DART®-1 have identical sequences. Such second/fourth polypeptide chain has the amino acid sequence (SEQ ID NO:27):

```
EIVLTQSPAT LSLSPGERAT LSCRASQSVS SYLAWYQQKP
GQAPRLLIYD ASNRATGIPA RFSGSGSGTD FTLTISSLEP
EDFAVYYCQQ SSNWPRTFGQ GTKVEIKGGG SGGGGQVQLQ
QWGAGLLKPS ETLSLTCAVY GGSFSDYYWN WIRQPPGKGL
EWIGEINHNG NTNSNPSLKS RVTLSLDTSK NQFSLKLRSV
TAADTAVYYC AFGYSDYEYN WFDPWGQGTL VTVSSGGCGG
GKVAACKEKV AALKEKVAAL KEKVAALKE
``` wherein, amino acid residues 1-107 are the amino acid residues of the Light Chain Variable Domain of PD-1 mAb 1 (SEQ ID NO:3), amino acid residues 108-115 are the amino acid residues of the linker GGGSGGGG (SEQ ID NO:13), amino acid residues 116-235 are the amino acid residues of the Heavy Chain Variable Domain of LAG-3 mAb 1 (SEQ ID NO:11), amino acid residues 236-241 are the amino acid residues of the cysteine-containing spacer peptide GGCGGG (SEQ ID NO:18), and amino acid residues 242-269 are the amino acid residues of the Modified K-Coil (SEQ ID NO:17).

A nucleic acid molecule that encodes such a second/fourth polypeptide chain is (SEQ ID NO:28):

```
gagatcgtac ttacccagtc tcccgccacc ctttccctga gtcctggtga gcgggccact ctttcctgtc gcgcaagcca atcagtttct agctacctcg catggtatca gcagaagcca gggcaggcac ccaggcttct catctatgac gccagtaacc gcgcaaccgg gatacctgct agattttccg gcagtggatc tgggaccgat ttcacactga caatttcatc cttggaacca gaagatttcg cagtctacta ctgccagcaa tcttccaact ggccaagaac tttcggacag gggaccaaag tggaaattaa aggtggcgga tccggcggcg gaggccaggt ccagctccag caatggggag ccgggctgct gaaaccctct gaaacactga gtctcacatg tgccgtttat ggaggttcct tctccgatta ttactggaac tggattcgtc agcctcccgg caagggcctg gagtggatcg gtgagattaa ccacaatggc aataccaata gcaatcctag tttgaaatct cgcgtcactc tttccctcga tacaagcaaa aaccagtttt ctttgaaatt gcgatctgta actgctgctg atactgccgt gtattactgc gcattcggct actccgacta tgaatataat tggttcgatc cttggggaca gggaacattg gtaaccgtgt catccggagg atgtggcggt ggaaaagtgg ccgcatgtaa ggagaaagtt gctgctttga aagagaaggt cgccgcactt aaggaaaagg tcgcagccct gaaagag
```

3. Second Exemplary PD-1×LAG-3 Bi-Specific Fc-DART® Diabody (PD-1×LAG-3 Fc-DART®-2)

A second particularly preferred PD-1×LAG-3 bi-specific, tetra-valent, Fc-DART® diabody of the present invention (PD-1×LAG-3 Fc-DART®-2) has first and third polypeptide chains of identical sequence. Such first/third polypeptide chain has the amino acid sequence (SEQ ID NO:29):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIKGGG SGGGGQVQLQ

QWGAGLLKPS ETLSLTCAVY GGSFSDYYWN WIRQPPGKGL

EWIGEINHNG NTNSNPSLKS RVTLSLDTSK NQFSLKLRSV

TAADTAVYYC AFGYSDYEYN WFDPWGQGTL VTVSSGGCGG

GEVAACEKEV AALEKEVAAL EKEVAALEKL EPKSADKTHT

CPPCPAPEAA GGPSVFLFPP KPKDTLYITR EPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP G
``` wherein, amino acid residues 1-107 are the amino acid residues of the Light Chain Variable Domain of PD-1 mAb 1 (SEQ ID NO:3), amino acid residues 108-115 are the amino acid residues of the linker GGGSGGGG (SEQ ID NO:13), amino acid residues 116-235 are the amino acid residues of the Heavy Chain Variable Domain of LAG-3 mAb 1 (SEQ ID NO:11), amino acid residues 236-241 are the amino acid residues of the cysteine-containing spacer peptide GGCGGG (SEQ ID NO:18), amino acid residues 242-269 are the amino acid residues of the Modified E-Coil (SEQ ID NO:16), amino acid residues 270-284 are the amino acid residues of the cysteine-containing linker peptide LEPKSADKTHTCPPC (SEQ ID NO:20) and amino acid residues 285-501 are the amino acid residues of the Modified CH2—CH3 Domain (SEQ ID NO:24).

A nucleic acid molecule that encodes such a first/third polypeptide chain is (SEQ ID NO:30):

```
gagatcgtac ttacccagtc tcccgccacc ctttccctga gtcctggtga gcgggccact ctttcctgtc gcgcaagcca atcagtttct agctacctcg catggtatca gcagaagcca gggcaggcac ccaggcttct catctatgac gccagtaacc gcgcaaccgg gatacctgct agattttccg gcagtggatc tgggaccgat ttcacactga caatttcatc cttggaacca gaagatttcg cagtctacta ctgccagcaa tcttccaact ggccaagaac tttcggacag gggaccaaag tggaaattaa aggtggcgga tccggcggcg gaggccaggt ccagctccag caatggggag ccgggctgct gaaaccctct gaaacactga gtctcacatg tgccgtttat ggaggttcct tctccgatta ttactggaac tggattcgtc agcctcccgg caagggcctg gagtggatcg gtgagattaa ccacaatggc aataccaata gcaatcctag tttgaaatct cgcgtcactc tttccctcga tacaagcaaa aaccagtttt ctttgaaatt gcgatctgta actgctgctg atactgccgt gtattactgc gcattcggct actccgacta tgaatataat tggttcgatc cttggggaca gggaacattg gtaaccgtgt catccggagg atgtggcggt ggagaagtgg ccgcatgtga gaaagaggtt gctgctttgg agaaggaggt cgctgcactt gaaaaggagg tcgcagccct ggagaaactg gagcccaaat ctgctgacaa aactcacaca tgcccaccgt gcccagcacc tgaagccgcg ggggaccgt cagtcttcct cttccccca aaacccaagg acaccctcta
```

```
tatcacccgg gagcctgagg tcacatgcgt ggtggtggac gtgagccacg aagacc ctga ggtcaagttc aactggtacg tggacggcgt ggaggtgcat aatgccaaga caaagccgcg ggaggagcag tacaacagca cgtaccgtgt ggtcagcgtc ctcaccgtcc tgcaccagga ctggctgaat ggcaaggagt acaagtgcaa ggtctccaac aaagccctcc cagccccat cgagaaaacc atctccaaag ccaaagggca gccccgagaa ccacaggtgt acaccctgcc cccatcccgg gaggagatga ccaagaacca ggtcagcctg acctgcctgg tcaaaggctt ctatcccagc gacatcgccg tggagtggga gagcaatggg cagccggaga caactacaa gaccacgcct cccgtgctgg actccgacgg ctccttcttc ctctacagca agctcaccgt ggacaagagc aggtggcagc aggggaacgt cttctcatgc tccgtgatgc atgaggctct gcacaaccac tacacgcaga agagcctctc cctgtctccg ggt
```

The second and fourth polypeptide chain of PD-1×LAG-3 Fc-DART®-2 have identical sequences. Such second/fourth polypeptide chain has the amino acid sequence (SEQ ID NO:31):

```
EIVLTQSPAT LSLSPGERAT LSCRASQSIS SYLAWYQQKP

GQAPRLLIYD ASNRATGIPA RFSGSGSGTD FTLTISSLEP

EDFAVYYCQQ RSNWPLTFGQ GTNLEIKGGG SGGGGQVQLV

ESGGGVVQPG RSLRLDCKAS GITFSNSGMH WVRQAPGKGL

EWVAVIWYDG SKRYYADSVK GRFTISRDNS KNTLFLQMNS

LRAEDTAVYY CATNDDYWGQ GTLVTVSSGG CGGGKVAACK

EKVAALKEKV AALKEKVAAL KE
``` wherein, amino acid residues 1-107 are the amino acid residues of the Light Chain Variable Domain of LAG-1 mAb 1 (SEQ ID NO:12), amino acid residues 108-115 are the amino acid residues of the linker GGGSGGGG (SEQ ID NO:13), amino acid residues 116-228 are the amino acid residues of the Heavy Chain Variable Domain of PD-1 mAb 1 (SEQ ID NO:2), amino acid residues 229-234 are the amino acid residues of the cysteine-containing spacer peptide GGCGGG (SEQ ID NO:18), and amino acid residues 235-262 are the amino acid residues of the Modified K-Coil (SEQ ID NO:17).

A nucleic acid molecule that encodes such a second/fourth polypeptide chain is (SEQ ID NO:32):

```
gaaattgtcc tgacacagtc tcccgcaacc ctgagtttga gtcctgggga gcgagcaact ctctcctgcc gagcctccca gagtatctcc tcctacctcg cctggtacca acagaagcca gggcaggctc caaggctgct tatctatgac gcctctaacc gcgcaactgg gattcccgca cgcttctccg gctctggttc cggcacagac tttacactta ctatctctag cctggagcca gaagactttg ccgtgtacta ttgtcagcaa cgttccaatt ggcccttac ctttgggcag ggcactaact tggaaatcaa aggtggcgga tccggcggcg gaggccaggt tcagctggtc gagagtggtg gcggcgttgt gcaacctggg cgttccctcc gattggactg taaagcttcc ggcattactt tctcaaattc cggcatgcat tgggtgaggc aagcccctgg aaaagggctc gaatgggtgg ctgtgatttg gtacgatggc agcaaacggt actacgccga ttctgttaag ggccgcttta ccatctcccg cgataactca aagaacacac tgtttctgca aatgaatagt cttagagccg aggacaccgc cgtgtactac tgtgccacaa atgacgatta ttgggggcag ggcacattgg tcacagtgtc ttccggagga tgtggcggtg gaaaagtggc cgcatgtaag gagaaagttg ctgctttgaa agagaaggtc gccgcactta aggaaaaggt cgcagccctg aaagag
```

III. Pharmaceutical Compositions

The present invention includes pharmaceutical compositions for the treatment of a cancer or a disease associated with the presence of a pathogen. Such compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a modified PD-1×LAG-3 bi-specific diabody of the present invention, (and especially a PD-1×LAG-3 bi-specific, tetra-valent, Fc-DART® diabody of the present invention) and a pharmaceutically acceptable carrier. Preferably, compositions of the invention comprise a prophylactically or therapeutically effective amount of one or more molecules of the invention and a pharmaceutically acceptable carrier. The invention also encompasses pharmaceutical compositions comprising such modified diabodies and a second therapeutic antibody that is specific for a particular pathogen-associated antigen, and a pharmaceutically acceptable carrier.

As used herein, the term "cancer" refers to a disease characterized by the presence of a malignant tumor. Such cancers include an adrenal gland cancer, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, or a uterine cancer.

As used herein, the term "disease associated with the presence of a pathogen" refers to a disease associated with an infection by a bacterium (e.g., *E. coli, C. difficile, Salmonella thyphimurium, Pseudomonas aeruginosa, Vibrio cholerae, Neisseria gonorrhoeae, Helicobacter pylori, Hemophilus influenzae, Shigella dysenteriae, Staphylococcus aureus, Mycobacterium tuberculosis* and *Streptococcus pneumonia*, etc.), a fungus (e.g., Candida, Aspergillus, Cryptococcus, Coccidioides, Histoplasma, Pneumocystis, Stachybotrys, etc.), a protozoan (Amoebozoa, Excavata, Chromalveolata, Entamoeba, Plasmodium, Giardia, Trypanosoma, Coccidia, Besnoitia, Dicrocoelium, Leishmania, etc.) or a virus (and especially an adenovirus, an adeno-associated virus, a B virus (macacine herpesvirus I), a BK virus, a bunyavirus, a chikungunya virus, a cocksackie virus, a coronavirus, a cytomegalovirus, an eastern equine encephalitis virus, an ebola virus, an enterovirus, an Epstein-Barr virus, a hantavirus, a hepatitis A virus, a hepatitis B virus, a hepatitis C virus, a hepatitis D virus, a hepatitis E virus, a herpes simplex virus 1, a herpes simplex virus 2, a human foamy virus, a human herpes virus 3, a human herpes virus 5, a human herpes virus 6, a human herpes virus 7, a human immunodeficiency virus, a human papillomavirus, a human β-lymphotropic virus, a human T-cell leukemia virus I, a human T-cell leukemia virus II, an influenza virus, a JC virus, a JEV, a Kaposi's sarcoma-associated herpesvirus, a Lassa virus, a lymphocytic choriomenengitis virus, a Marburg virus, a measles virus, a mumps virus, a Nipah virus, a norovirus, a Norwalk virus, an orthoreovirus, a parainfluenza virus, a parvovirus, a poliovirus, a rabies virus, a reovirus, a respiratory syncytial virus, rhinovirus, a Rift Valley fever virus, a rotavirus, rubella virus, a smallpox virus, a St Louis encephalitis virus, a variola major virus, a variola minor virus, a vericella-zoster virus, a West Nile virus, a western equine encephalitis virus, or a yellow fever virus).

As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) infected cells or other diseased cells, decreasing symptoms resulting from the disease, increasing the quality of life of those suffering from the disease, decreasing the dose of other medications required to treat the disease, delaying the progression of the disease, and/or prolonging survival of companion animal recipients.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers containing a PD-1×LAG-3 bi-specific diabody of the present invention, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more molecules of the invention. In another embodiment, a kit further comprises one or more other prophylactic or therapeutic agents useful for the treatment of cancer or a disease characterized by the presence of a pathogen-associated antigen, in one or more containers. In another embodiment, a kit further comprises one or more antibodies or diabodies that bind one or more pathogen-associated antigens. In certain embodiments, the other prophylactic or therapeutic agent is a chemotherapeutic. In other embodiments, the prophylactic or therapeutic agent is a biological or hormonal therapeutic.

IV. Methods of Producing the PD-1×LAG-3 Bi-Specific Diabodies Of The Present Invention The PD-1×LAG-3 bi-specific diabodies of the present invention are most preferably produced through the recombinant expression of nucleic acid molecules that encode such polypeptides, as is well-known in the art.

Polypeptides of the invention may be conveniently prepared using solid phase peptide synthesis (Merrifield, B. (1986) "Solid Phase Synthesis," Science 232(4748):341-347; Houghten, R.A. (1985) "General Method For The Rapid Solid-Phase Synthesis Of Large Numbers Of Peptides: Specificity Of Antigen-Antibody Interaction At The Level Of Individual Amino Acids," Proc. Natl. Acad. Sci. (U.S.A.) 82(15):5131-5135; Ganesan, A. (2006) "Solid-Phase Synthesis In The Twenty-First Century," Mini Rev. Med. Chem. 6(1):3-10).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) "Production Of Antibodies And Antibody Fragments In Plants," Vaccine 19:2756; Lonberg, N. et al. (1995) "Human Antibodies From Transgenic Mice," Int. Rev. Immunol 13:65-93; and Pollock et al. (1999) "Transgenic Milk As A Method For The Production Of Recombinant Antibodies," J. Immunol Methods 231:147-157). Suitable methods for making derivatives of antibodies, e.g., chimeric, humanized, single-chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "Making Antibodies By Phage Display Technology," Annu. Rev. Immunol. 12.433-455).

The antibodies or protein of interest may be subjected to sequencing by Edman degradation, which is well-known to those of skill in the art. The peptide information generated from mass spectrometry or Edman degradation can be used to design probes or primers that are used to clone the protein of interest.

An alternative method of cloning the protein of interest is by "panning" using purified proteins or portions thereof for cells expressing the antibody or protein of interest. The "panning" procedure may be conducted by obtaining a cDNA library from tissues or cells that express or overexpress the desired cDNAs in a second cell type, and screening the transfected cells of the second cell type for a specific binding to the desired protein. Detailed descriptions of the methods used in cloning mammalian genes coding for cell-surface proteins by "panning" can be found in the art (see, for example, Aruffo, A. et al. (1987) "Molecular Cloning Of A CD28 cDNA By A High-Efficiency COS Cell Expression System," Proc. Natl. Acad. Sci. (U.S.A.) 84:8573-8577 and Stephan, J. et al. (1999) "Selective Cloning Of Cell Surface Proteins Involved In Organ Development: Epithelial Glycoprotein Is Involved In Normal Epithelial Differentiation," Endocrinol. 140:5841-5854).

cDNAs encoding antibodies, and other peptide agonists, antagonists and modulators can be obtained by reverse transcribing the mRNAs from a particular cell type according to standard methods in the art. Specifically, mRNA can be isolated using various lytic enzymes or chemical solutions according to the procedures set forth in Sambrook et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, more preferably 20-fold higher, more preferably 50-fold higher, more preferably 100-fold higher than that of the corresponding endogenous antibody or protein of interest, if present, in the host cells. Screening the host cells for a specific binding to a desired protein is preferably effected by an immunoassay or FACS. A cell over-expressing the antibody or protein of interest can be identified in this way.

Various techniques are also available which may now be employed to produce mutant peptide agonists, antagonists, and modulators which encodes for additions, deletions, or changes in amino acid sequence of the resultant protein relative to the parent peptide agonist, antagonist or modulator molecule.

The invention includes modifications to the PD-1×LAG-3 bi-specific diabody of the invention that do not significantly affect their properties and variants that have enhanced or decreased activity. Modification of polypeptides is routine practice in the art. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. These polypeptides also include glycosylated and non-glycosylated polypeptides, as well as polypeptides with other post translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation.

Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more fragments or regions from the polypeptides and antibodies of this invention. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a Light Chain Variable Region and a Heavy Chain Variable Region of an antibody produced from a publicly-deposited hybridoma. For purposes of this invention, an antibody fusion protein contains one or more polypeptide Domains that specifically bind to a desired viral epitope or a desired activating receptor of an immune effector cell or a protein present on the surface of an immune effector cell that expresses such an activating receptor and another amino acid sequence to which it is not attached in the native molecule, for example, a heterologous sequence or a homologous sequence from another region.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, such a polypeptide could be produced by an automated polypeptide synthesizer employing the solid phase method.

V. Uses of the Compositions of the Invention

The present invention encompasses compositions, including pharmaceutical compositions, comprising the PD-1×LAG-3 bi-specific diabodies of the present invention, polypeptides derived from such molecules, polynucleotides comprising sequences encoding such molecules or polypeptides, and other agents as described herein.

In that the PD-1×LAG-3 bi-specific diabodies of the present invention have the ability attenuate the inhibition of the immune system mediated by PD-1 and LAG-3, the PD-1×LAG-3 bi-specific diabodies of the present invention may be used to treat any disease or condition associated with an undesirably suppressed immune system, including cancer and diseases that are associated with the presence of a pathogen (e.g., a bacterial, fungal, viral or protozoan infection).

VI. Methods of Administration

The compositions of the present invention may be provided for the treatment, prophylaxis, and amelioration of one or more symptoms associated with a disease, disorder or infection by administering to a subject an effective amount of a pharmaceutical composition of the invention. In a preferred aspect, such compositions are substantially purified (i.e., substantially free from substances that limit its effect or produce undesired side-effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "Receptor-Mediated In Vitro Gene Transformation By A Soluble DNA Carrier System," J. Biol. Chem. 262: 4429-4432), construction of a nucleic acid as part of a retroviral or other vector, etc.

Methods of administering the PD-1×LAG-3 bi-specific diabodies of the present invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the PD-1×LAG-3 bi-specific diabodies of the present invention may be packaged in a hermetically sealed container such as an ampoule or sachette indicating the quantity of such molecules. In one embodiment, the PD-1×LAG-3 bi-specific diabodies of the present invention are supplied as a dry sterilized lyophilized powder or water free concentrate in a hermetically sealed container and can be reconstituted, e.g., with water or saline to the appropriate concentration for administration to a subject. Preferably, the PD-1×LAG-3 bi-specific diabodies of the present invention are supplied as a dry sterile lyophilized powder in a hermetically sealed container at a unit dosage of at least 5 µg, more preferably at least 10 µg, at least 15 µg, at least 25 µg, at least 50 µg, at least 100 µg, or at least 200 µg.

The lyophilized PD-1×LAG-3 bi-specific diabodies of the present invention should be stored at between 2 and 8° C. in their original container and the molecules should be administered within 12 hours, preferably within 6 hours, within 5 hours, within 3 hours, or within 1 hour after being reconstituted. In an alternative embodiment, the PD-1×LAG-3 bi-specific diabodies of the present invention are supplied in liquid form in a hermetically sealed container indicating the quantity and concentration of the molecule, fusion protein, or conjugated molecule. Preferably, the liquid form of the PD-1×LAG-3 bi-specific diabodies of the present invention is supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

As used herein, an "effective amount" of a pharmaceutical composition, in one embodiment, is an amount sufficient to effect beneficial or desired results including, without limitation, clinical results such as decreasing symptoms resulting from the disease attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/ or prolonging survival of individuals.

An effective amount can be administered in one or more administrations. For purposes of this invention, an effective amount of drug, compound, or pharmaceutical composition is an amount sufficient to reduce the proliferation of (or the effect of) viral presence and to reduce and/or delay the development of the viral disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages for antibody administration comprise one or more unit doses between 0.1-to 100 mg/kg/body weight.

The amount of the PD-1×LAG-3 bi-specific diabodies of the present invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For the PD-1×LAG-3 bi-specific diabodies of the present invention, the dosage administered to a patient is typically at least about 0.01 µg/kg, at least about 0.05 µg/kg, at least about 0.1 µg/kg, at least about 0.2 µg/kg, at least about 0.5 µg/kg, at least about 1 µg/kg, at least about 2 µg/kg, at least about 5 µg/kg, at least about 10 µg/kg, at least about 20 µg/kg, at least about 50 µg/kg, at least about 0.1 mg/kg, at least about 1 mg/kg, at least about 5 mg/kg, at least about 10 mg/kg, at least about 30 mg/kg, at least about 50 mg/kg, at least about 75 mg/kg, at least about 100 mg/kg, at least about 125 mg/kg, at least about 150 mg/kg or more of the subject's body weight.

In another embodiment, the patient is administered a treatment regimen comprising one or more doses of such prophylactically or therapeutically effective amount of the PD-1×LAG-3 bi-specific diabodies of the present invention, wherein the treatment regimen is administered over 2 days, 3 days, 4 days, 5 days, 6 days or 7 days. In certain embodiments, the treatment regimen comprises intermittently administering doses of the prophylactically or therapeutically effective amount of the PD-1×LAG-3 bi-specific diabodies of the present invention (for example, administering a dose on day 1, day 2, day 3 and day 4 of a given week and not administering doses of the prophylactically or therapeutically effective amount of the PD-1×LAG-3 bi-specific diabodies of the present invention on day 5, day 6 and day 7 of the same week). Typically, there are 1, 2, 3, 4, 5, or more courses of treatment. Each course may be the same regimen or a different regimen.

In another embodiment, the administered dose escalates over the first quarter, first half or first two-thirds or three-quarters of the regimen(s) (e.g., over the first, second, or third regimens of a 4 course treatment) until the daily prophylactically or therapeutically effective amount of the PD-1×LAG-3 bi-specific diabodies encompassed by the invention is achieved.

In one embodiment, the dosage of the PD-1×LAG-3 bi-specific diabodies of the present invention administered to a patient may be calculated for use as a single agent therapy. In another embodiment the PD-1×LAG-3 bi-specific diabodies of the present invention are used in combination with other therapeutic compositions and the dosage administered to a patient are lower than when such diabodies are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

In another embodiment, the compositions can be delivered in a vesicle, in particular a liposome (See Langer (1990) "New Methods Of Drug Delivery," Science 249:1527-1533); Treat et al., in Liposomes in the Therapy of Infectious Disease and Cancer, Lopez-Berestein and Fidler (eds.), Liss, New York, pp. 353- 365 (1989); Lopez-Berestein, ibid., pp. 3 17-327; see generally ibid.).

In yet another embodiment, the compositions can be delivered in a controlled release or sustained release system. Any technique known to one of skill in the art can be used to produce sustained release formulations comprising one or more molecules of the invention. See, e.g., U.S. Pat. No. 4,526,938; PCT publication WO 91/05548; PCT publication WO 96/20698; Ning et al. (1996) "Intratumoral Radioimmunotheraphy Of A Human Colon Cancer Xenograft Using A Sustained-Release Gel," Radiotherapy & Oncology 39:179-189, Song et al. (1995) "Antibody Mediated Lung Targeting Of Long-Circulating Emulsions," PDA Journal of Pharmaceutical Science & Technology 50:372-397; Cleek et al. (1997) "Biodegradable Polymeric Carriers For A bFGF Antibody For Cardiovascular Application," Pro. Int'l. Symp. Control. Rel. Bioact. Mater. 24:853-854; and Lam et al. (1997) "Microencapsulation Of Recombinant Humanized Monoclonal Antibody For Local Delivery," Proc. Int'l. Symp. Control Rel. Bioact. Mater. 24:759-760, each of which is incorporated herein by reference in its entirety. In one embodiment, a pump may be used in a controlled release system (See Langer, supra; Sefton, (1987) "Implantable Pumps," CRC Crit. Rev. Biomed. Eng. 14:201-240; Buchwald et al. (1980) "Long-Term, Continuous Intravenous Heparin Administration By An Implantable Infusion Pump In Ambulatory Patients With Recurrent Venous Thrombosis," Surgery 88:507-516; and Saudek et al. (1989) "A Preliminary Trial Of The Programmable Implantable Medication System For Insulin Delivery," N. Engl. J. Med. 321:574-579). In another embodiment, polymeric materials can be used to achieve controlled release of antibodies (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, N.Y. (1984); Levy et al. (1985) "Inhibition Of Calcification Of Bioprosthetic Heart Valves By Local Controlled-Release Diphosphonate," Science 228:190-192; During et al. (1989) "Controlled Release Of Dopamine From A Polymeric Brain Implant: In Vivo Characterization," Ann. Neurol. 25:351-356; Howard et al. (1989) "Intracerebral Drug Delivery In Rats With Lesion-Induced Memory Deficits," J. Neurosurg. 7(1):105-112); U.S. Patent No. 5,679,377; U.S. Patent No. 5,916,597; U.S. Patent No. 5,912,015; U.S. Patent No. 5,989,463; U.S. Patent No. 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, "New Methods Of Drug Delivery," Science 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al. (1996) "Intratumoral Radioimmunotheraphy Of A Human Colon Cancer Xenograft Using A Sustained-Release Gel," Radiotherapy & Oncology 39:179-189, Song et al. (1995) "Antibody Mediated Lung Targeting Of Long-Circulating Emulsions," PDA Journal of Pharmaceutical Science & Technology 50:372-397; Cleek et al. (1997) "Biodegradable Polymeric Carriers For A bFGF Antibody For Cardiovascular Application," Pro. Int'l. Symp. Control. Rel. Bioact. Mater. 24:853-854; and Lam et al. (1997) "Microencapsulation Of Recombinant Humanized Monoclonal Antibody For Local Delivery," Proc. Int'l. Symp. Control Rel. Bioact. Mater. 24:759-760, each of which is incorporated herein by reference in its entirety.

In a specific embodiment where the composition of the invention is a nucleic acid encoding one or more of the polypeptide chains of a PD-1×LAG-3 bi-specific diabody of the present invention, the nucleic acid can be administered in vivo to promote expression of its encoded diabody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al. (1991) "Antennapedia Homeobox Peptide Regulates Neural Morphogenesis," Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of the PD-1×LAG-3 bi-specific diabodies of the present invention can include a single treatment or, preferably, can include a series of treatments. In a preferred example, a subject is treated with molecules of the invention one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the molecules used for treatment may increase or decrease over the course of a particular treatment.

Having now generally described the invention, the same will be more readily understood through reference to the following Examples. Such Examples are provided by way of illustration and are not intended to be limiting of the present invention unless specified.

Example 1

Production and Properties of PD-1×LAG-3 Bi-Specific Diabodies

Figure 5:
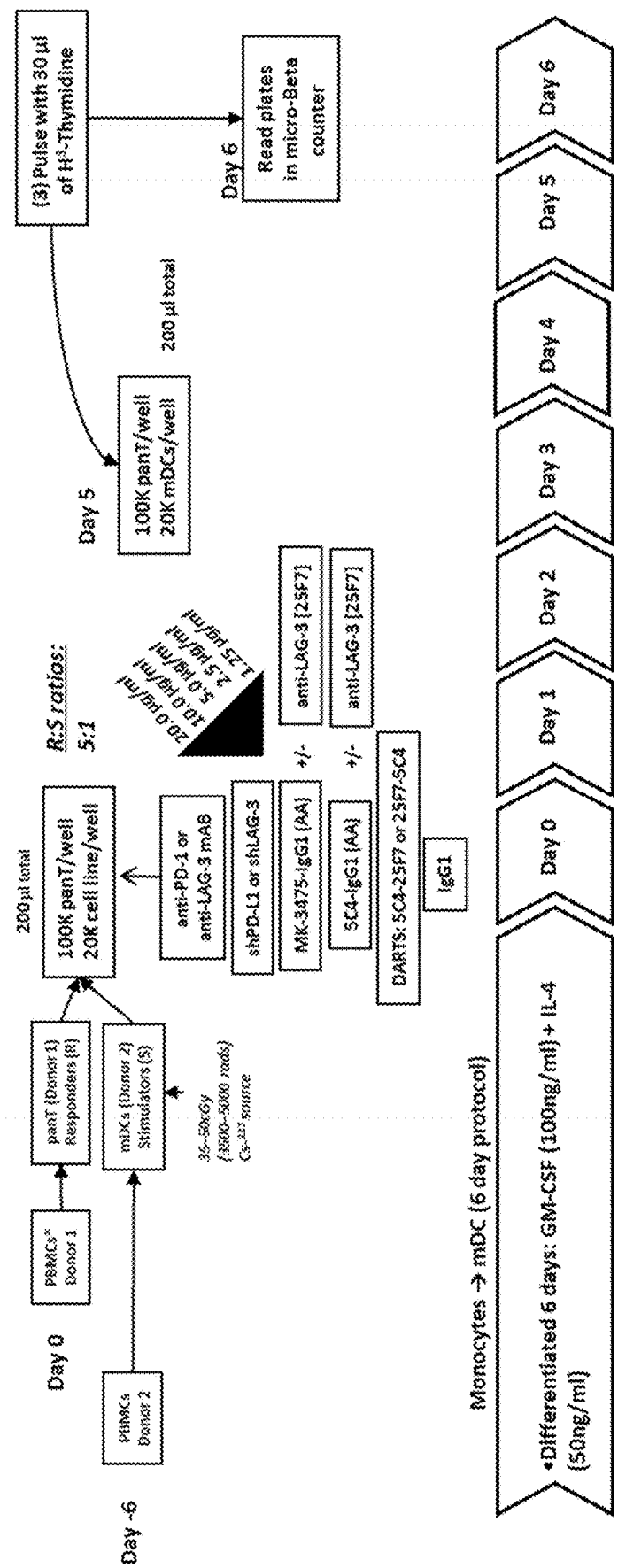
FIG. 5 shows a diagram of the protocol for assessing the ability of anti-PD-1 and anti-LAG-3 antibodies to enhance the proliferation of T-cells.
Figure 6:
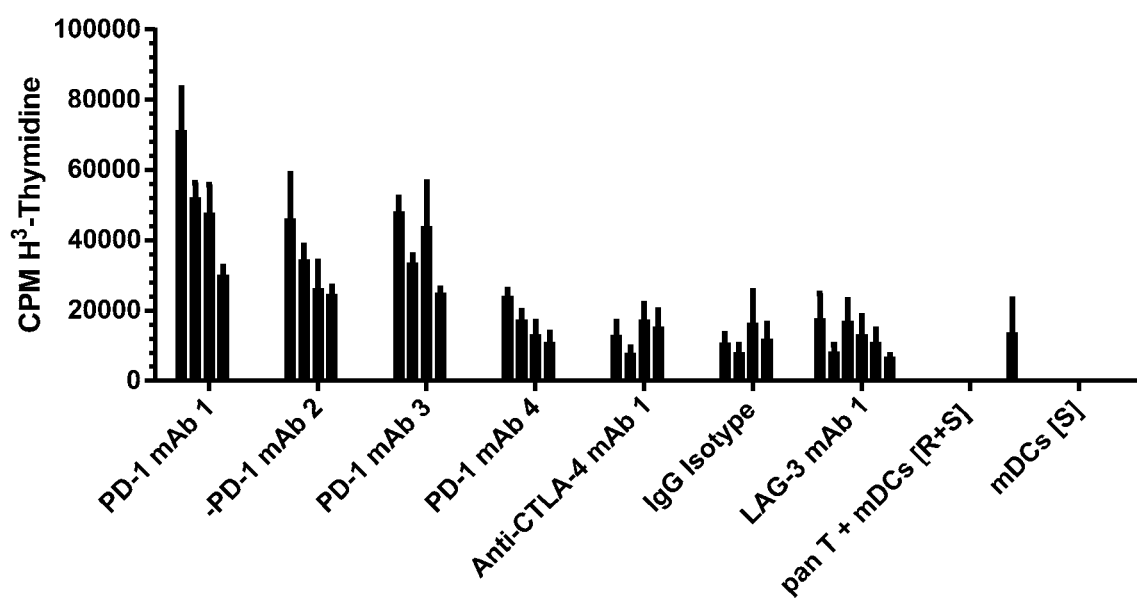
FIG. 6 shows that the addition of PD-1 mAb 1 (5C4; BMS-936558), PD-1 mAb 2 (MK-3475; Merck, lambrolizumab) and PD-1 mAb 3 (EH12.2H7; Dana Farber) at the start of the allo-MLR assay, induced a strong T-cell proliferation response compared to IgG1 isotype control antibody. Also shown are the proliferative responses obtained with PD-1 mAb 4 (CT-011; CureTech, BAT-1), an anti-CTLA mAb and LAG-3 mAb 1 (25F7; BMS-986016, Medarex/BMS). Responder (R) cells are pan T cells; stimulator (S)cells are mature dendritic cells (mDCs).

Within the context of the allo-MLR assay, T-cells are induced to proliferate in response to HLA-mismatching (Latchman, Y.E. et al. (2004) "PD-L1-Deficient Mice Show That PD-L1 On T-Cells, Antigen-Presenting Cells, And Host Tissues Negatively Regulates T-Cells." Proc. Natl. Acad. Sci. (U.S.A.) 101(29):10691-10696; Wang, W. et al. (2008) "PD-L1/PD-1 Signal Deficiency Promotes Allogeneic Immune Responses And Accelerates Heart Allograft Rejection," Transplantation 86(6):836-44) or mitogenic/ pharmacological stimulation. Agonist antibodies that target costimulatory molecules are known to induce proliferative responses by re-enforcing T-cell signaling and stabilizing transcription factors that promote or drive T-cell effector function (Melero, I. et al. (2013) "Agonist Antibodies to TNFR Molecules That Costimulate T and NK Cells," Clin. Cancer Res. 19(5):1044-1053). Similarly, antagonist antibodies that target key checkpoint molecules that negatively regulate T-cell responses can induce proliferative responses by maintaining T-cell signaling and effector function and thereby improving antitumor immunity (Capece, D. et al. (2012) "Targeting Costimulatory Molecules to Improve Antitumor Immunity," J. Biomed. Biotech. 2012:926321). The effect of monoclonal antibodies against co-stimulatory or checkpoint targets on proliferation in response to alloantigen can be easily measure in short-term mixed lymphocyte (allo-MLR) reactions by following the incorporation of $^3$H-thymidine. To address ability of antibodies against checkpoint inhibitors to enhance proliferation, benchmark anti-PD-1 or anti-LAG-3 mAbs were generated, purified, and exogenously added at the initiation of allo-MLR assay at 20, 10, 5, 2.5, and 1.25 µg/ml (FIG. 5). At the end of 5-6 days, the 96-well plated was pulse with $^3$H-thymidine and cultured for 18 hrs to measure proliferation. Several benchmark antibodies against human PD-1, LAG-3, and CTLA-4 were evaluated in their capacity to enhance T-cell proliferation in response to allo-antigen stimulation. As shown in FIG. 6, the addition of PD-1 mAb 1 (5C4 (BMS-936558), PD-1 mAb 2 (MK-3475; Merck, lambrolizumab), or PD-1 mAb 3 (EH12.2H7; Dana Farber) at the start of the allo-MLR assay, induced strong T-cell proliferation compared to IgG1 isotype control antibody or the control wells containing responders and stimulators. Wells containing irradiated stimulator cells alone demonstrated no proliferation. Although a dose dependent proliferative response was observed, PD-1 mAb 4 (CT-011; CureTech, BAT-1) showed minimal proliferation compared to PD-1 mAb 1(5C4 (BMS-936558), PD-1 mAb 2 (MK-3475; Merck, lambrolizumab), or PD-1 mAb 3 (EH12.2H7; Dana Farber). A slight dose dependent proliferative response was also observed with LAG-3 mAb 1 (25F7; BMS-986016, Medarex/BMS), which compared similarly to Yervoy® ipilimumab, an anti-CTLA-4 mAb (Bristol Myers-Squib).

Figure 7:
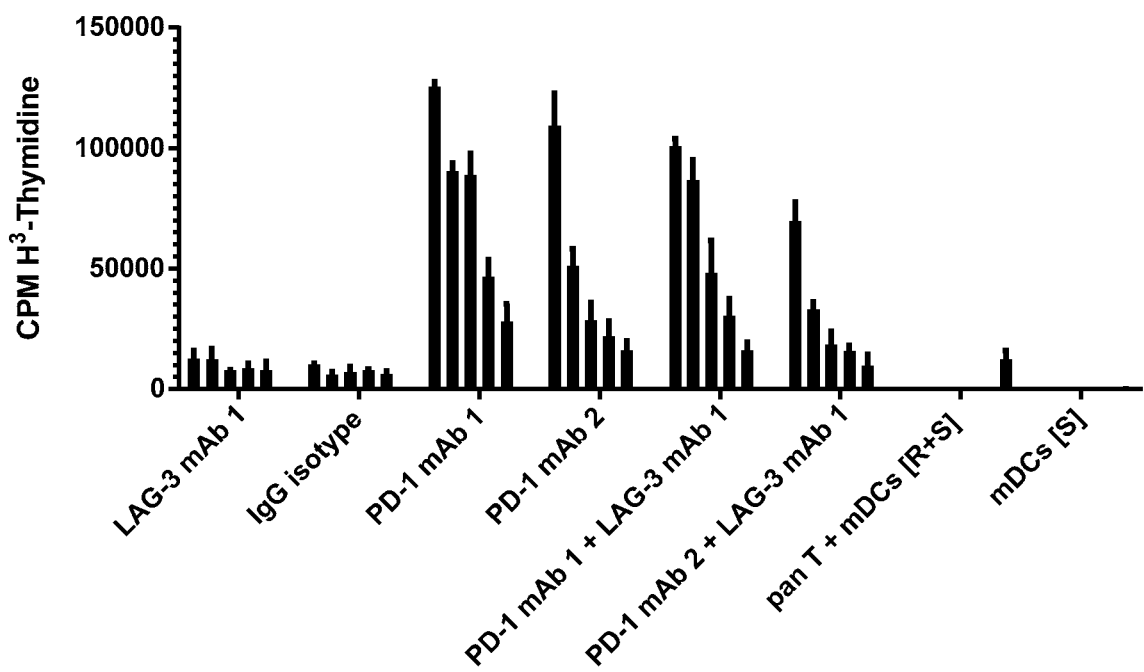
FIG. 7 shows the results of an evaluation of LAG-3 mAb 1 (25F7; BMS-986016, Medarex/BMS), for T-cell proliferative potential either alone or in combination with PD-1 mAb 1 (5C4; BMS-936558)), PD-1 mAb 2 (MK-3475; Merck, lambrolizumab). Responder (R) cells are pan T cells; stimulator (S)cells are mature dendritic cells (mDCs).

The striking effectiveness of PD-1 mAb 1 (5C4 (BMS-936558), given concurrently with LAG-3 mAb 1 (25F7; BMS-986016, Medarex/BMS) in eliciting potent anti-tumor immunity in animal models when compared to either antibody given alone (Woo, S. R. et al. (2012) "Immune Inhibitory Molecules LAG-3 And PD-1 Synergistically Regulate T-Cell Function To Promote Tumoral Immune Escape," Cancer Res. 72(4):917-927), suggested that benchmark mAbs given in combination may potentiate allo-induced T-cell proliferation greater than either antibody alone. As shown in FIG. 7, anti-LAG-3 mAb (25F7) was evaluated for its proliferative potential either alone or in combination with the anti-PD-1 mAbs (PD-1 mAb 1 (5C4 (BMS-936558) or PD-1 mAb 2 (MK-3475; Merck, lambrolizumab)). As observed previously, both anti-PD-1 mAbs induced potent proliferation in a dose dependent manner. In contrast, provision of anti-LAG-3 mAb with either anti-PD-1 mAb did not induce enhanced proliferation beyond that observed with anti-PD-1 mAbs alone. Anti-LAG-3 mAb alone exhibited only slight T-cell proliferation in comparison to isotype IgG1 control or responder plus stimulator control wells.

Figure 8:
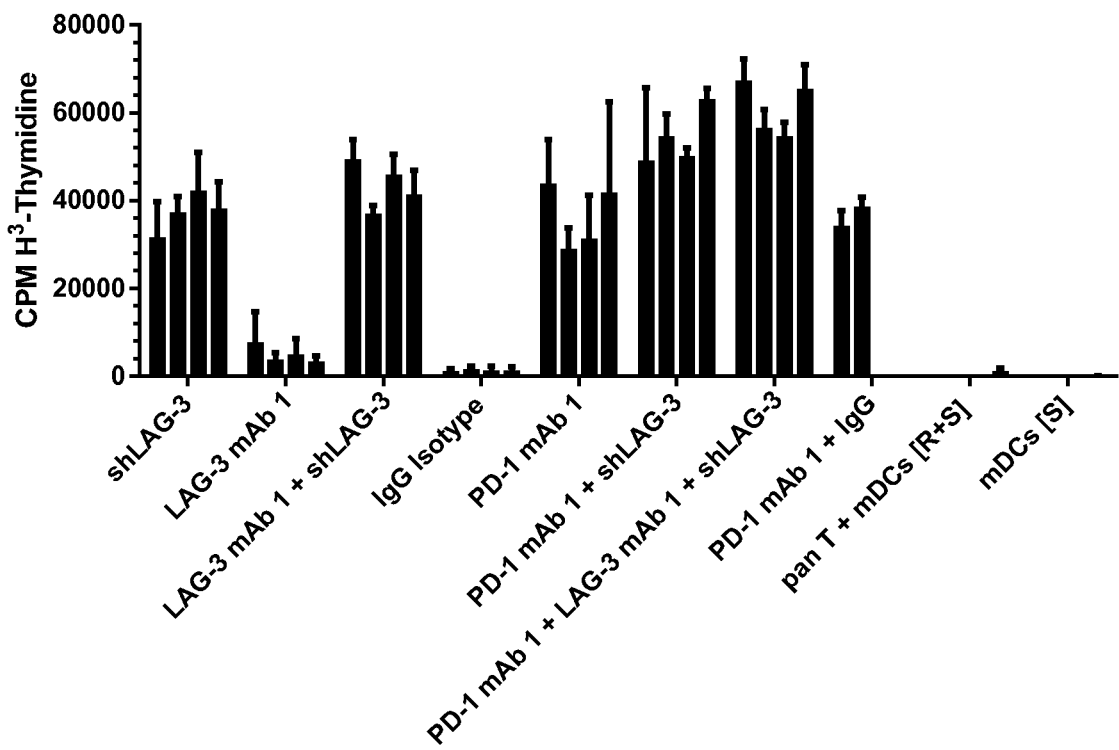
FIG. 8 shows that soluble human LAG-3 (shLAG-3), which binds to human HLA-class II molecules expressed on both APCs and CD4 T-cells, induced a robust proliferative response compared to IgG isotype or responder (R) (pan T cells) plus stimulator (S) (mature dendritic cells (mDCs) control wells.

The inability of anti-LAG-3 mAbs to induce proliferation alone or in combination beyond that observed with anti-PD-1 mAbs suggested that either LAG-3 expression is absent on T-cells during the allo-MLR assay or that anti-LAG-3 mAb does not bind to LAG-3 to block a negative signal cascade. In order to assay the potential to induce LAG-3 signal transduction, soluble human LAG-3 protein ("shLAG-3") was added to the allo-MLR and compared against anti-LAG-3 mAb and/or anti-PD-1 mAbs. As shown in FIG. 8, soluble human LAG-3, which binds to human HLA-class II molecules expressed on both APCs and CD4 T-cells, induced a robust proliferative response compared to IgG isotype or responder plus stimulator control wells. Addition of LAG-3 mAb 1(25F7; BMS-986016, Medarex/BMS), did not seem to block the proliferative effect of soluble human LAG-3 protein and may have slightly enhanced T-cell proliferation, as a slight dose dependent proliferative response was observed. Consistent with previous observations, anti-PD-1 mAb induced potent T-cell proliferation that was further enhanced by the addition of both soluble human LAG-3 protein and/or LAG-3 mAb 1 (25F7; BMS-986016, Medarex/BMS). Addition of isotype IgG1 control to anti-PD-1 antibodies did not enhance T-cell proliferation beyond that observed with PD-1 mAb 1 (5C4 (BMS-936558) alone. The ability of soluble LAG-3 to induce potent T-cell proliferation even in the presence of anti-LAG-3 mAbs is unclear. One possibility is that anti-LAG-3 mAb is simply unable to block the strong proliferative signal induced by soluble LAG-3 mAb. An alternative—but not necessarily non-mutually exclusive possibility—is that soluble human LAG-3 protein together with anti-LAG-3 forms immune cross-linking complexes that can further potentiate proliferative responses.

The ability of soluble LAG-3 to potentiate T-cell proliferation suggested that introduction of both anti-PD-1 and anti-LAG-3 mAbs in close proximity might enhance T-cell proliferative responses within the allo-MLR assay. To address this possibility, benchmark anti-PD-1 and anti-LAG-3 mAbs were constructed within the dual affinity retargeting (DART®)-bi-specific format in two orientations: a LAG-3 mAb 1 (25F7; BMS-986016, Medarex/BMS)—PD-1 mAb 1 (5C4 (BMS-936558) bi-specific, tetra-valent Fc-DART® diabody (PD-1×LAG-3 Fe-DART®-1) and a PD-1 mAb 1 (5C4 (BMS-936558)—LAG-3 mAb 1 (25F7; BMS-986016, Medarex/BMS) bi-specific, tetra-valent Fc-DART® diabody (PD-1×LAG-3 Fe-DART®-1). Both Fc-DART® formats were exogenously added (in the dose-dependent manner described above) at the beginning of the allo-MLR and evaluated for their T-cell proliferative potential.

Figure 9A:
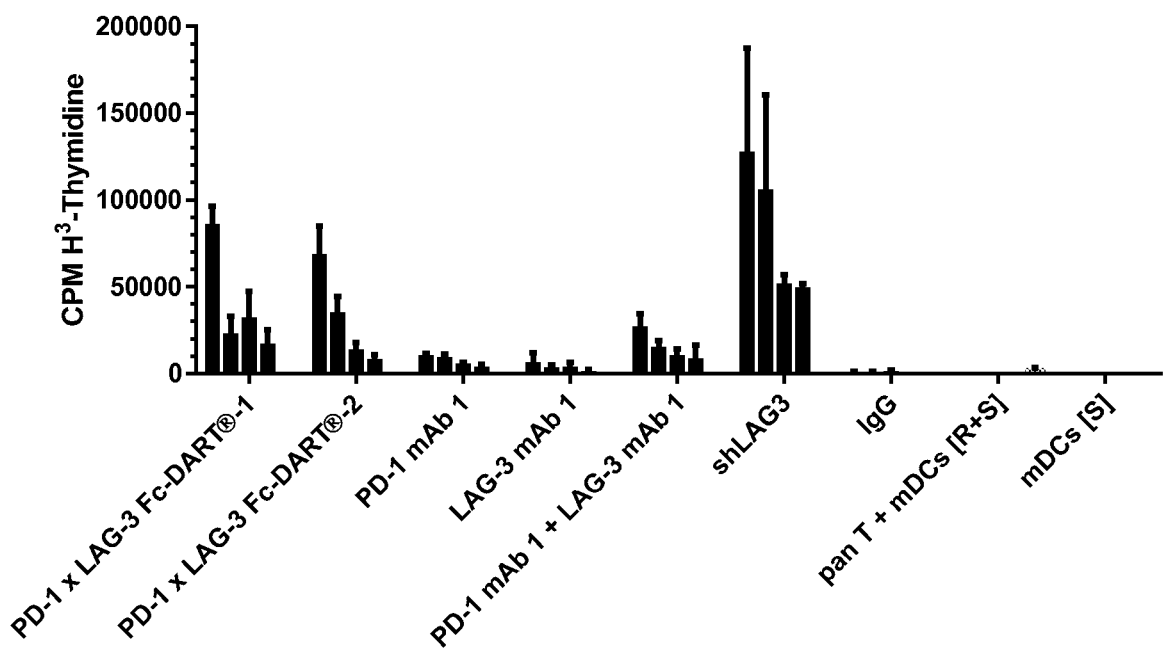
FIGS. 9A-9B show that the PD-1×LAG-3 bi-specific diabodies of the present invention induced potent T-cell proliferative responses when compared against anti-PD-1 mAb (5C4) or anti-LAG-3 mAb (25F7).
Figure 9B:
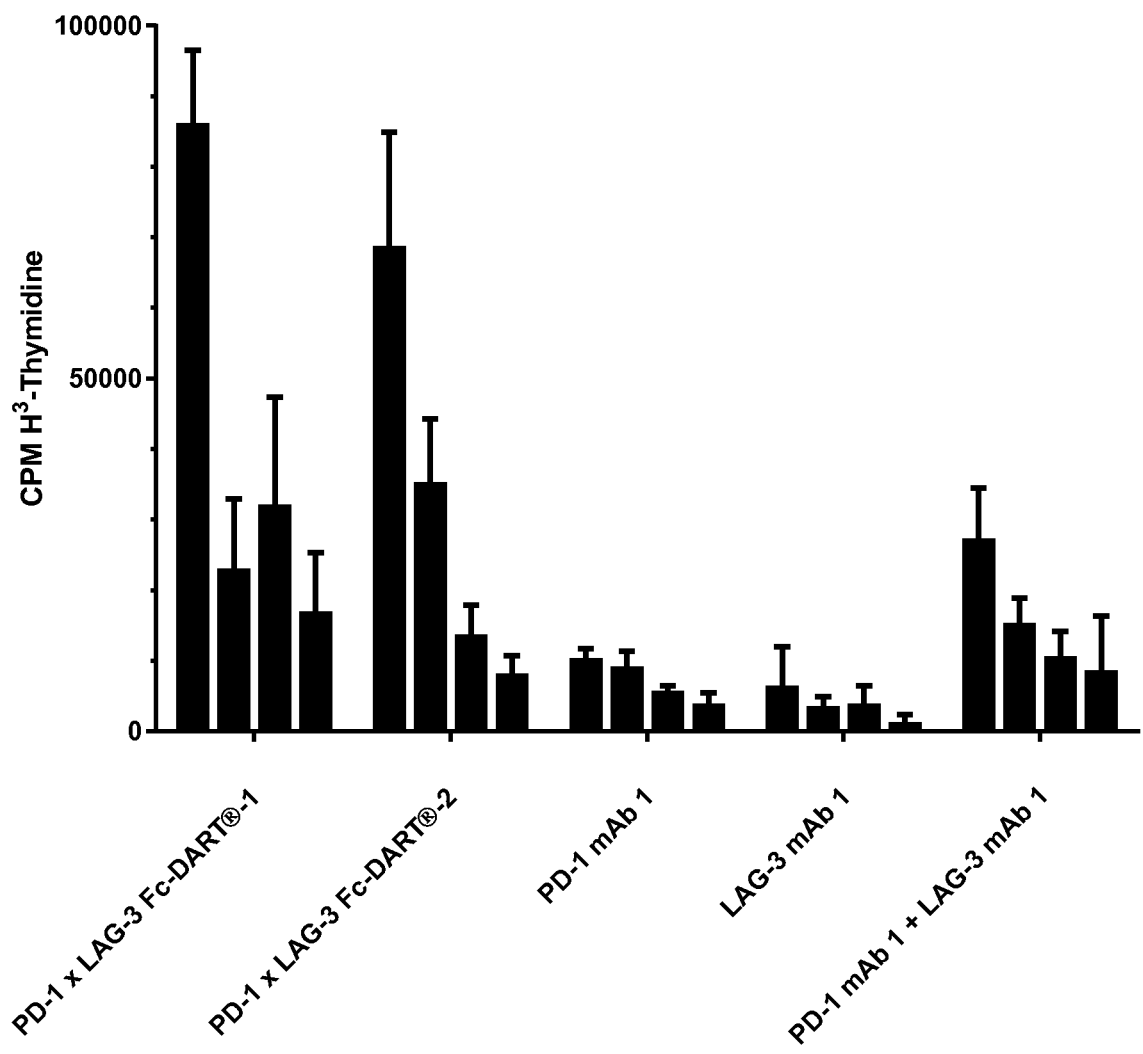

As shown in FIGS. 9A-9B, both -DART® diabodies induced surprisingly more potent T-cell proliferative responses than those obtained with PD-1 mAb 1 (5C4 (BMS-936558) and/or LAG-3 mAb 1 (25F7; BMS-986016, Medarex/BMS). Soluble human LAG-3 ("shLAG-3") again demonstrated strong T-cell proliferation within the allo-MLR assay. The strong proliferative signal induced by both DART®s and soluble human LAG-3 protein, minimized the contribution of anti-PD-1 mAb or anti-LAG-3 mAb alone. While both anti-PD-1 and LAG-3 mAbs induced T-cell proliferation in a dose dependent manner beyond that observed with IgG1 isotype control or responder plus stimulator wells alone, the combination of anti-PD-1 with anti-LAG-3 demonstrated enhanced proliferation then either antibody alone, suggesting as previous reports in the literature have demonstrated a functional synergy (Wang, W. et al. (2008) "PD-L1/PD-1 Signal Deficiency Promotes Allogeneic Immune Responses And Accelerates Heart Allograft Rejection," Transplantation 86(6):836-44; Melero, I. et al. (2013) "Agonist Antibodies to TNFR Molecules That Costimulate T and NK Cells," Clin. Cancer Res. 19(5):1044-1053; Capece, D. et al. (2012) "Targeting Costimulatory Molecules to Improve Antitumor Immunity," J. Biomed. Biotech. 2012:926321).

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of attenuating PD-1 and LAG-3-mediated immune system inhibition in a subject in need thereof, said method comprising administering to said subject a bi-specific Fc diabody capable of immunospecific binding to an epitope of PD-1 and to an epitope of LAG-3, wherein said diabody comprises first, second, third and fourth polypeptide chains, each having an amino terminus and a carboxy terminus, and wherein:
(A) said first and second polypeptide chains are covalently bonded to one another, said first and third polypeptide chains are covalently bonded to one another, and said third and fourth polypeptide chains are covalently bonded to one another;
(B) said first and third polypeptide chains of said diabody each comprise, in the N-terminal to C-terminal direction, a Light Chain Variable Domain of an antibody that is immunospecific for PD-1 or LAG-3, a Heavy Chain Variable Domain of an antibody that is immunospecific for LAG-3 or PD-1, a Heterodimer-Promoting Domain and a CH2-CH3 Domain, wherein said Light Chain Variable Domains and said Heavy Chain Variable Domains are incapable of associating to form an Epitope-Binding Site capable of binding an epitope of PD-1 or an epitope of LAG-3; and
(C) said second and said fourth polypeptide chains of said diabody each comprise, in the N-terminal to C-terminal direction, a Light Chain Variable Domain of an antibody that is immunospecific for PD-1 or LAG-3, a Heavy Chain Variable Domain of an antibody that is immunospecific for LAG-3 or PD-1, and a Heterodimer-Promoting Domain, wherein said Light Chain Variable Domains and said Heavy Chain Variable Domains are incapable of associating to form an Epitope-Binding Site capable of binding an epitope of PD-1 or an epitope of LAG-3;
and wherein:
I. (2) said Light Chain Variable Domain of said first polypeptide chain and said Heavy Chain Variable Domain of said second polypeptide chain associate to form a first Epitope-Binding Site and said Heavy Chain Variable Domain of said first polypeptide chain and said Light Chain Variable Domain of said second polypeptide chain associate to form a second Epitope-Binding Site; and
(2) said Light Chain Variable Domain of said third polypeptide chain and said Heavy Chain Variable Domain of said fourth polypeptide chain associate to form a third Epitope-Binding Site and said Heavy Chain Variable Domain of said third polypeptide chain and said Light Chain Variable Domain of said fourth polypeptide chain associate to form a fourth Epitope-Binding Site;
wherein:
(i) said first and third Epitope-Binding Sites are capable of immunospecifically binding to an epitope of PD-1 and said second and fourth Epitope-Binding Sites are capable of immunospecifically binding to an epitope of LAG-3; or (ii) said first and third Epitope-Binding Sites are capable of immunospecifically binding to an epitope of LAG-3 and said second and fourth Epitope-Binding Sites are capable of immunospecifically binding to an epitope of PD-1; and II. (1) said Heterodimer-Promoting Domain of said first and third polypeptide chains each comprises an amino acid sequence of SEQ ID NO:16 and said Heterodimer-Promoting Domain of said second and fourth polypeptide chains each comprises an amino acid sequence of SEQ ID NO:17; or (2) said Heterodimer-Promoting Domain of said first and third polypeptide chains each comprises the amino acid sequence of SEQ ID NO:17 and said Heterodimer-Promoting Domain of said second and fourth polypeptide chains each comprises the amino acid sequence of SEQ ID NO:16; and III. said $CH_2$—$CH_3$ Domains of said first and third polypeptide chains associate to form an Fc Domain.

2. The method of claim 1, wherein said $CH_2$—$CH_3$ Domains of said first and third polypeptide chains each comprises the amino acid sequence of SEQ ID NO:24.

3. The method of claim 1, wherein:
(a) said Heavy Chain Variable Domain of an antibody that is immunospecific for LAG-3 comprises the amino acid sequence of SEQ ID NO:11, and wherein said Light Chain Variable Domain of an antibody that is immunospecific for LAG-3 comprises the amino acid sequence of SEQ ID NO:12; and/or
(b) said Heavy Chain Variable Domain of an antibody that is immunospecific for PD-1 comprises the amino acid sequence of SEQ ID NO:2, and wherein said Light Chain Variable Domain of an antibody that is immunospecific for PD-1 comprises the amino acid sequence of SEQ ID NO:3.

4. The method of claim 2, wherein:
(a) said Heavy Chain Variable Domain of an antibody that is immunospecific for LAG-3 comprises the amino acid sequence of SEQ ID NO:11, and wherein said Light Chain Variable Domain of an antibody that is immunospecific for LAG-3 comprises the amino acid sequence of SEQ ID NO:12; and/or
(b) said Heavy Chain Variable Domain of an antibody that is immunospecific for PD-1 comprises the amino acid sequence of SEQ ID NO:2, and wherein said Light Chain Variable Domain of an antibody that is immunospecific for PD-1 comprises the amino acid sequence of SEQ ID NO:3.

5. The method of claim 1, wherein:
(A) said first and third polypeptide chains each comprise a Light Chain Variable Domain of an antibody that is immunospecific for PD-1 and a Heavy Chain Variable Domain of an antibody that is immunospecific for LAG-3; and
(B) said second and fourth polypeptide chains each comprise a Light Chain Variable Domain of an antibody that is immunospecific for LAG-3 and a Heavy Chain Variable Domain of an antibody that is immunospecific for PD-1.

6. The method of claim 2, wherein:
(A) said first and third polypeptide chains each comprise a Light Chain Variable Domain of an antibody that is immunospecific for PD-1 and a Heavy Chain Variable Domain of an antibody that is immunospecific for LAG-3; and
(B) said second and fourth polypeptide chains each comprise a Light Chain Variable Domain of an antibody that is immunospecific for LAG-3 and a Heavy Chain Variable Domain of an antibody that is immunospecific for PD-1.

7. The method of claim 1, wherein:
(A) said first and third polypeptide chains each comprise a Light Chain Variable Domain of an antibody that is immunospecific for LAG-3 and a Heavy Chain Variable Domain of an antibody that is immunospecific for PD-1; and
(B) said second and fourth polypeptide chains each comprise a Light Chain Variable Domain of an antibody that is immunospecific for PD-1 and a Heavy Chain Variable Domain of an antibody that is immunospecific for LAG-3.

8. The method of claim 2, wherein:
(A) said first and third polypeptide chains each comprise a Light Chain Variable Domain of an antibody that is immunospecific for LAG-3 and a Heavy Chain Variable Domain of an antibody that is immunospecific for PD-1; and
(B) said second and fourth polypeptide chains each comprise a Light Chain Variable Domain of an antibody that is immunospecific for PD-1 and a Heavy Chain Variable Domain of an antibody that is immunospecific for LAG-3.

9. The method of claim 1, wherein said Heavy Chain Variable Domain is separated from said Heterodimer-Promoting Domain in each of said first, second, third and fourth polypeptide chains by a linker comprising the amino acid sequence of SEQ ID NO:18.

10. The method of claim 2, wherein said Heavy Chain Variable Domain is separated from said Heterodimer-Promoting Domain in each of said first, second, third and fourth polypeptide chains by a linker comprising the amino acid sequence of SEQ ID NO:18.

11. The method of claim 5, wherein said Heavy Chain Variable Domain is separated from said Heterodimer-Promoting Domain in each of said first, second, third and fourth polypeptide chains by a linker comprising the amino acid sequence of SEQ ID NO:18.

12. The method of claim 6, wherein said Heavy Chain Variable Domain is separated from said Heterodimer-Promoting Domain in each of said first, second, third and fourth polypeptide chains by a linker comprising the amino acid sequence of SEQ ID NO:18.

13. The method of claim 7, wherein said Heavy Chain Variable Domain is separated from said Heterodimer-Promoting Domain in each of said first, second, third and fourth polypeptide chains by a linker comprising the amino acid sequence of SEQ ID NO:18.

14. The method of claim 8, wherein said Heavy Chain Variable Domain is separated from said Heterodimer-Promoting Domain in each of said first, second, third and fourth polypeptide chains by a linker comprising the amino acid sequence of SEQ ID NO:18.

* * * * *